(12) United States Patent
Benowitz

(10) Patent No.: US 8,912,144 B2
(45) Date of Patent: Dec. 16, 2014

(54) METHOD FOR TREATING STROKE VIA ADMINISTRATION OF NEP1-40 AND INOSINE

(75) Inventor: Larry I. Benowitz, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 517 days.

(21) Appl. No.: 12/790,515

(22) Filed: May 28, 2010

(65) Prior Publication Data
US 2011/0071088 A1    Mar. 24, 2011

Related U.S. Application Data

(63) Continuation-in-part of application No. 10/580,364, filed as application No. PCT/US2004/042255 on Dec. 16, 2004, now abandoned.

(60) Provisional application No. 60/529,833, filed on Dec. 16, 2003.

(51) Int. Cl.
| A61K 38/00 | (2006.01) |
| A61K 31/7076 | (2006.01) |
| A61K 38/17 | (2006.01) |
| C12N 15/86 | (2006.01) |
| A61K 48/00 | (2006.01) |

(52) U.S. Cl.
CPC .............. *A61K 38/1709* (2013.01); *A61K 48/00* (2013.01); *C12N 2750/14145* (2013.01); *C12N 2750/14143* (2013.01); *A61K 31/7076* (2013.01); *A61K 48/005* (2013.01); *C12N 15/86* (2013.01)
USPC ........................................................ 514/17.8

(58) Field of Classification Search
CPC ........... A61K 2300/00; A61K 31/7076; A61K 38/1709; A61K 38/00; A61K 48/00; A61K 48/005; C12N 15/86; C12N 2750/14143; C12N 2750/14145
USPC ............... 514/17.7, 17.8, 18.2, 21.3; 435/375
See application file for complete search history.

(56) References Cited

U.S. PATENT DOCUMENTS

| 4,341,868 | A | 7/1982 | Nakanishi et al. |
| 4,883,666 | A | 11/1989 | Sabel et al. |
| 5,187,162 | A | 2/1993 | Marangos et al. |
| 5,250,414 | A | 10/1993 | Schwab et al. |
| 5,422,343 | A | 6/1995 | Yamamoto et al. |
| 5,438,130 | A | 8/1995 | Goldin et al. |
| 5,447,939 | A | 9/1995 | Glasky et al. |
| 5,587,384 | A | 12/1996 | Zhang et al. |
| 5,707,649 | A | 1/1998 | Inokuchi et al. |
| RE36,397 | E | 11/1999 | Zhang et al. |
| 6,440,455 | B1 | 8/2002 | Benowitz |
| 6,551,612 | B2 | 4/2003 | Benowitz |
| 6,855,690 | B2 | 2/2005 | Benowitz |
| 7,338,666 | B2 | 3/2008 | Benowitz |
| 7,935,680 | B2 | 5/2011 | Benowitz |
| 2002/0012965 | A1 | 1/2002 | Strittmatter |
| 2002/0055484 | A1 | 5/2002 | Benowitz |
| 2002/0077295 | A1 | 6/2002 | Strittmatter |
| 2003/0049254 | A1 | 3/2003 | Kaufman et al. |
| 2003/0113325 | A1 | 6/2003 | He et al. |
| 2003/0113891 | A1 | 6/2003 | Blatt et al. |
| 2003/0124704 | A1 | 7/2003 | Strittmatter et al. |
| 2003/0203870 | A1 | 10/2003 | Blatt et al. |
| 2004/0014710 | A1 | 1/2004 | Benowitz |

FOREIGN PATENT DOCUMENTS

| JP | 74015765 | 4/1974 |
| JP | H07-509002 | 10/1995 |
| RU | 2063753 C1 | 4/1993 |
| RU | 2063753 C1 | 7/1996 |
| WO | WO 88/09335 A1 | 12/1988 |
| WO | WO 94/00132 A1 | 1/1994 |
| WO | 94/17831 | 8/1994 |
| WO | WO 97/03652 A1 | 2/1997 |
| WO | 03/031462 A2 | 4/2003 |
| WO | 2004/014311 A2 | 2/2004 |
| WO | 2004/090103 A2 | 10/2004 |

OTHER PUBLICATIONS

Chen et al. Inosine induces axonal rewiring and improves behavioral outcome after stroke. Proc Natl Acad Sci U S A. Jun. 25, 2002;99(13):9031-6.*
Purves, Dale, et al (Eds.), Neuroscience, 2001, Sinauer Associates, Inc., 2nd Edition, pp. 403, 554, 555, and 678.*
Chen et al., "Nogo-A is myelin-associated neurite outgrowth inhibitor and an antigen form monoclonal antibody IN-I" Nature (2000) vol. 403, pp. 434-439.
Cui et al., "Intraocular elevation of cyclic AMP potentiates ciliary neurotrophic factor-induced regeneration of adult rat retinal ganglion cell axons" Molecular and Cellular Neuroscience (2003) vol. 22, pp. 49-61.
Cui et al., "Synergistic Effect of Nogo-Neutralizing Antibody IN-I and Ciliary Neurotrophic Factor on Axonal Regeneration in Adult Rodent Visual Systems" Journal of Neurotrauma (2004) vol. 21 No. 5, pp. 617-625.
Dergham et al. Rho signaling pathway targeted to promote spinal cord repair. J Neurosci. Aug. 1, 2002;22(15):6570-7.

(Continued)

*Primary Examiner* — Gregory S Emch
(74) *Attorney, Agent, or Firm* — David S. Resnick; Shayne Y. Huff; Nixon Peabody LLP

(57) ABSTRACT

Disclosed herein is a method for stimulating axonal outgrowth of central nervous system (CNS) neurons comprising contacting the CNS neurons with an effective amount of NEP1-40 and inosine, to thereby stimulate axonal outgrowth. The method may further comprise contacting the CNS neurons with a cAMP modulator that increases the concentration of intracellular cAMP. Also disclosed is a method for treating a neurological disorder selected from the group consisting of traumatic brain injury, stroke, spinal cord injury, optic neuropathy, retinal nerve damage and optic nerve damage, in a patient in need thereof comprising administering an effective amount of NEP1-40 and inosine to the patient.

6 Claims, 30 Drawing Sheets

(56) References Cited

OTHER PUBLICATIONS

Fischer et al., "Axon Regeneration in the Rat Optic Nerve: Essential Role of the Nogo Receptor" Society for Neuroscience Abstract Viewer and Itinerary Planner (2003) vol. 2003, Abstract No. 678.6.
Fischer et al., "Counteracting the Nogo Receptor Enhances Optic Nerve Regeneration if Retinal Ganglion Cells are in an Active Growth State" The Journal of Neuroscience (2004) vol. 27 No. 7, pp. 1646-1651.
Fischer, et al., Switching Mature Retinal Ganglion Cells to a Robust Growth State in Vivo, The Journal of Neuroscience, Oct. 6, 2004, pp. 8726-8740, vol. 24, No. 40.
Grandpre, et al., Nogo-66 Receptor Antagonist Peptide Promotes Axonal Regeneration, Nature, May 30, 2002, pp. 547-552, vol. 417.
Li et al., "Axon Regeneration in Goldfish and Rat Retinal Ganglion Cells: Differential Responsiveness to Carbohydrates and CAMP" The Journal of Neuroscience (2003) vol. 23 No. 21, pp. 7830-7838.
Lu et al., "Combinatorial Therapy with Neurotrophins and CAMP Promotes Axonal Regeneration beyond Sites of Spinal Cord Injury" The Journal of Neuroscience (2004) vol. 24 No. 28, pp. 6402-6409.
Neumann et al. Regeneration of sensory axons within the injured spinal cord induced by intraganglionic CAMP elevation. Neuron 2002, Jun. 13; 34(6): 885-893.
Ng, Cherry Ee Lin and Bor Luen Tang, "Nogos and the Nogo-66 Receptor: Factors Inhibiting CNS Neuron Regeneration" Journal of Neuroscience Research (2002) vol. 67, pp. 559-565.
Peel et al. Adeno-associated virus vectors: activity and applications in the CNS. J Neurosci Methods. Jun. 1, 2000;98 (2):95-104.
Schnell et al., "Neurotrophin-3 enhances sprouting of corticospinal tract during development and after adult spinal cord lesion" Nature (1994) vol. 367 pp. 170-173.
Yin et al., "Macrophage-Derived Factors Stimulate Optic Nerve Regeneration" The Journal of Neuroscience (2003) vol. 23 No. 6, pp. 2284-2293.
Zai et al., "Inosine Alters Gene Expression and Axonal Projections in Neurons Contralateral to a Cortical Infarct and Improves Skilled Use of the Impaired Limb" The Journal of Neuroscience (2009) vol. 29, No. 25, pp. 8187-8197.
Benowitz, L.I., et al.; Dept. of Neuroscience Abstracts; 23(1-2) (1997).
Bold, J.M., et al.; Br. J. Pharmac.; 84:689-696 (1985).
Braumann, T., et al.; J. of Neurochem.; 912-919 (1986).
Christjanson, L.J., et al.; GLIA; 7:176-182 (1993).
Greene, L.A., et al.; J. of Neuroscience; 10(5):1479-1485 (1990).
Gysbers, J.W., et al.; NeuroReport; 3(11):997-1000 (1992).
Gysbers, J.W., et al.; Int. J. Dev. Neuroscience; 14(1):19-34 (1996).
Hayashi, E., et al.; Euro. J. of Pharmac.; 48:297-307 (1978).
Huffaker, T., et al.; J. of Cellular Physiology; 120:188-196 (1984).
Juhasz-Nagy, A., et al.; J. of Pahrac. and Experimental Therapeutics; 202(3):683-695 (1977).
Matz, H., et al.; J. of Neuroscience Research; 24:260-267 (1989).
Nagasawa, H., et al.; Neuroscience Letters; 133:129-132 (1991).
Rathbone, M.P., et al.; Medical Hypotheses; 37:232-240 (1992).
Rolls, E.T., et al.; Physiology & Behavior; 59(4/5):991-1000 (1996).
Satoh, T., et al.; Mol. Cell Biol.; 7(12):4553-4556 (1987).
Schwalb, J.M., et al.; Neuroscience; 72(4):901-910 (1996).
Schwalb, J.M., et al.; J. of Neuroscience; 15(8):5514-5525 (1995).
Standaert, F.G., et al.; J. of Pharmac. and Experimental Therapeutics; 199(3):544-552 (1976).
Svensson, B., et al.; Euro. J. of Neuroscience; 5:1017-1023 (1993).
Volonte, C., et al.; The J. of Cell Bio.; 109:2395-2403 (1989).
Wakade, T.D., et al.; J. of Physiology; 488(1):123-138 (1995).
Zarbin, M.A., et al.; Exp. Brain Res.; 81:267-278 (1990).
Zurn, A.D., et al.; Proc. Natl. Acad. Sci. USA; 85:8301-8305 (1998).
Takeo et al.; J. Mol. Cell. Cardiol.; 20(3):187-199 (1998).
Cui, L et al., Effect of Nucleoside Analogs on Neurite Regeneration and Mitochondrial DNA Synthesis in PC-12 Cells, J. Pharmacol. Exp. ther., 280(3):1228-1234 (1997).
Glasky, A.J. et al., Effect of AIT-082, A Purine Analog, on Working Memory in Normal and Aged Mice, Pharmacol. Biochem. and Behavior, 47:325-329 (1994).
Kadota, T. et al., Expression of Dopamine Transporter at the Tips of Growth Neurite of PC12 Cells, J. Histochem. Cytochem., 44(9):989-996 (1996).
Middlemiss, P.J. et al., AIT-082, a unique purine derivative, enhances nerve growth factor mediated neurite outgrowth from PC12 cells, Neuroscience Letters 199:131-134 (1995).
Sidtis, J.J. et al., Stable Neurological Function in Subjects Treated with 2'3'-dideoxyinosine, J. Neurovirol 3:233-240 (1997).
SIGMA Chemical Company Catalog, p. 565 (1992).
Yamaguchi, H. et al., Effect of Aniracetam on NGF-Induced Neurite Outgrowth Ratio in PC12 Cells, Jpn. Pharmacol. Ther., 25(7):1801-1805 (1997). English abstract.
Bareyre FM, Kerschensteiner M, Raineteau O, Mettenleiter TC, Weinmann O, Schwab ME (2004) The injured spinal cord spontaneously forms a new intraspinal circuit in adult rats. Nat Neurosci 7:269-277.
Benowitz LI, Jing Y, Tabibiazar R, Jo SA, Petrausch B, Stuermer CA, Rosenberg PA, Irwin N (1998) Axon outgrowth is regulated by an intracellular purine-sensitive mechanism in retinal ganglion cells. J Biol Chem 273:29626-29634.
Cafferty WB, Strittmatter SM (2006) The Nogo-Nogo receptor pathway limits a spectrum of adult CNS axonal growth. J Neurosci 26:12242-12250.
Carmichael ST (2006) Cellular and molecular mechanisms of neural repair after stroke: making waves. Ann Neurol 59:735-742.
Carmichael ST, Wei L, Rovainen CM, Woolsey TA (2001) New patterns of intracortical projections after focal cortical stroke. Neurobiol Dis 8:910-922.
Carmichael ST, Archibeque I, Luke L, Nolan T, Momiy J, Li S (2005) Growth-associated gene expression after stroke: evidence for a growth-promoting region in peri-infarct cortex. Exp Neurol 193:291-311.
Chen P, Goldberg DE, Kolb B, Lanser M, Benowitz LI (2002) Inosine induces axonal rewiring and improves behavioral outcome after stroke. Proc Natl Acad Sci U S A 99:9031-9036.
Dancause N, Barbay S, Frost SB, Plautz EJ, Chen D, Zoubina EV, Stowe AM, Nudo RJ (2005) Extensive cortical rewiring after brain injury. J Neurosci 25:10167-10179.
Emerick AJ, Neafsey EJ, Schwab ME, Kartje GL (2003) Functional reorganization of the motor cortex in adult rats after cortical lesion and treatment with monoclonal antibody IN-1. J Neurosci 23:4826-4830.
Hasko G, Sitkovsky MV, Szabo C (2004) Immunomodulatory and neuroprotective effects of inosine. Trends Pharmacol Sci 25:152-157.
Hasko G, Kuhel DG, Nemeth ZH, Mabley JG, Stachlewitz RF, Virag L, Lohinai Z, Southan GJ, Salzman AL, Szabo C (2000) Inosine inhibits inflammatory cytokine production by a post-transcriptional mechanism and protects against endotoxin-induced shock. J Immunol 164:1013-1019.
Haun SE, Segeleon JE, Trapp VL, Clotz MA, Horrocks LA (1996) Inosine mediates the protective effect of adenosine in rat astrocyte cultures subjected to combined glucose-oxygen deprivation. Journal of Neurochemistry 67:2051-2059.
Havton L, Kellerth JO (1987) Regeneration by supernumerary axons with synaptic terminals in spinal motoneurons of cats. Nature 325:711-714.
Irwin N, Li Ym, O'Toole JE, Benowitz LI (2006) Mst3b, a purine-sensitive Ste20-like protein kinase, regulates axon outgrowth. Proc Natl Acad Sci U S A 103:18320-18325.
Jurkowitz MS, Litsky ML, Browning MJ, Hohl CM (1998) Adenosine, inosine, and guanosine protect glial cells during glucose deprivation and mitochondrial inhibition: correlation between protection and ATP preservation. J Neurochem 71:535-548.
Lagerback PA, Ronnevi LO, Cullheim S, Kellerth JO (1981) An ultrastructural study of the synaptic contacts of alpha-motoneurone axon collaterals. I. Contacts in lamina IX and with identified alpha-motoneurone dendrites in lamina VII. Brain Res 207:247-266.

(56) References Cited

OTHER PUBLICATIONS

Lee JK, Kim JE, Sivula M, Strittmatter SM (2004) Nogo receptor antagonism promotes stroke recovery by enhancing axonal plasticity. J Neurosci 24:6209-6217.

Liu F, You SW, Yao LP, Liu HL, Jiao XY, Shi M, Zhao QB, Ju G (2006b) Secondary degeneration reduced by inosine after spinal cord injury in rats. Spinal Cord 44:421-426.

Lorber B, Howe Ml, Benowitz LI, Irwin N (2008) Mst3b, an Ste20-like kinase, regulates axon regeneration in the mature CNS and PNS. (submitted).

Marangos PJ, Trams E, Clark-Rosenberg RL, Paul SM, Skolnick P (1981) Anticonvulsant doses of inosine result in brain levels sufficient to inhibit [3H] diazepam binding. Psychopharmacology (Berl) 75:175-178.

Nudo RJ (2006) Mechanisms for recovery of motor function following cortical damage. Curr Opin Neurobiol 16:638-644.

Papadopoulos CM, Tsai SY, Alsbiei T, O'Brien TE, Schwab ME, Kartje GL (2002) Functional recovery and neuroanatomical plasticity following middle cerebral artery occlusion and IN-1 antibody treatment in the adult rat. Ann Neurol 51:433-441.

Scott GS, Cuzzocrea S, Genovese T, Koprowski H, Hooper DC (2005) Uric acid protects against secondary damage after spinal cord injury. Proc Natl Acad Sci U S A 102:3483-3488.

Scott GS, Spitsin SV, Kean RB, Mikheeva T, Koprowski H, Hooper DC (2002) Therapeutic intervention in experimental allergic encephalomyelitis by administration of uric acid precursors. Proc Natl Acad Sci U S A 99:16303-16308.

Shen H, Chen GJ, Harvey BK, Bickford PC, Wang Y (2005) Inosine reduces ischemic brain injury in rats. Stroke 36:654-659.

Smith JM, Lunga P, Story D, Harris N, Le Belle J, James MF, Pickard JD, Fawcett JW (2007) Inosine promotes recovery of skilled motor function in a model of focal brain injury. Brain 130:915-925.

Stevens B, Allen NJ, Vazquez LE, Howell GR, Christopherson KS, Nouri N, Micheva KD, Mehalow AK, Huberman AD, Stafford B, Sher A, Litke AM, Lambris JD, Smith SJ, John SW, Barres BA (2007) The classical complement cascade mediates CNS synapse elimination. Cell 131:1164-1178.

Weidner N, Ner A, Salimi N, Tuszynski MH (2001) Spontaneous corticospinal axonal plasticity and functional recovery after adult central nervous system injury. Proc Natl Acad Sci U S A 98:3513-3518.

Zurn A, Do K (1988) Purine metabolite inosine is an adrenergic neurotrophic substance for cultured chicken sympathetic neurons. Proc Natl Acad Sci USA 85:8301-8305.

* cited by examiner

FIG. 5

```
Arg Ile Tyr Lys Gly Val Ile Gln Ala Ile Gln Lys Ser Asp Glu Gly
 1               5                  10                      15
His Pro Phe Arg Ala Tyr Leu Glu Ser Glu Val Ala Ile Ser Glu Glu
            20                  25                  30
Leu Val Gln Lys Tyr Ser Asn Ser     SEQ ID NO:1
        35              40

Ile Gln Lys Ser Asp Glu Gly His Pro Phe Arg Ala Tyr Leu Glu Ser
 1               5                  10                      15
Glu Val Ala Ile Ser Glu Glu Leu Val     SEQ ID NO:2
            20                  25

Arg Ala Tyr Leu Glu Ser Glu Val Ala Ile Ser Glu Glu Leu Val Gln
 1               5                  10                      15
Lys Tyr Ser Asn Ser Ala Leu Gly His     SEQ ID NO:3
            20                  25

Ser Glu Glu Leu Val Gln Lys Tyr Ser Asn Ser Ala Leu Gly His Val
 1               5                  10                      15
Asn Cys Thr Ile Lys Glu Leu Arg Arg     SEQ ID NO:4
            20                  25

Ala Leu Gly His Val Asn Cys Thr Ile Lys Glu Leu Arg Arg Leu Phe
 1               5                  10                      15
Leu Val Asp Asp Leu Val Asp Ser Leu     SEQ ID NO:5
            20                  25

Arg Ile Tyr Lys Gly Val Ile Gln Ala Ile Gln Lys Ser Asp Glu Gly
 1               5                  10                      15
His Pro Phe Arg Ala Tyr Leu Glu Ser Glu Val Ala Ile Ser Glu Glu
            20                  25                  30
Leu Val Gln Lys Tyr Ser Asn Ser     SEQ ID NO:6
        35              40

Phe Arg Ile Tyr Lys Gly Val Ile Gln Ala Ile Gln Lys Ser Asp Glu
 1               5                  10                      15
Gly His Pro Phe Arg Ala Tyr Leu Glu Ser Glu Val Ala Ile Ser Glu
            20                  25                  30
Glu Leu Val Gln Lys Tyr Ser Asn Ser Ala Leu Gly His Val Asn Cys
            35                  40                  45
Thr Ile Lys Glu Leu Arg Arg Leu Phe Leu Val Asp Asp Leu Val Asp
    50                  55                  60
Ser Leu     SEQ ID NO:7
 65
```

FIG. 6

```
Met Lys Arg Ala Ser Ala Gly Gly Ser Arg Leu Leu Ala Trp Val Leu
 1               5                  10                    15
Trp Leu Gln Ala Trp Gln Val Ala Ala Pro Cys Pro Gly Ala Cys Val
            20                  25                  30
Cys Tyr Asn Glu Pro Lys Val Thr Thr Ser Cys Pro Gln Gly Leu
        35                  40                  45
Gln Ala Val Pro Val Gly Ile Pro Ala Ala Ser Gln Arg Ile Phe Leu
    50                  55                  60
His Gly Asn Arg Ile Ser His Val Pro Ala Ala Ser Phe Arg Ala Cys
 65              70                  75                    80
Arg Asn Leu Thr Ile Leu Trp Leu His Ser Asn Val Leu Ala Arg Ile
                85                  90                  95
Asp Ala Ala Ala Phe Thr Gly Leu Ala Leu Leu Glu Gln Leu Asp Leu
            100                 105                 110
Ser Asp Asn Ala Gln Leu Arg Ser Val Asp Pro Ala Thr Phe His Gly
        115                 120                 125
Leu Gly Arg Leu His Thr Leu His Leu Asp Arg Cys Gly Leu Gln Glu
    130                 135                 140
Leu Gly Pro Gly Leu Phe Arg Gly Leu Ala Ala Leu Gln Tyr Leu Tyr
145                 150                 155                 160
Leu Gln Asp Asn Ala Leu Gln Ala Leu Pro Asp Asp Thr Phe Arg Asp
                165                 170                 175
Leu Gly Asn Leu Thr His Leu Phe Leu His Gly Asn Arg Ile Ser Ser
            180                 185                 190
Val Pro Glu Arg Ala Phe Arg Gly Leu His Ser Leu Asp Arg Leu Leu
        195                 200                 205
Leu His Gln Asn Arg Val Ala His Val His Pro His Ala Phe Arg Asp
    210                 215                 220
Leu Gly Arg Leu Met Thr Leu Tyr Leu Phe Ala Asn Asn Leu Ser Ala
225                 230                 235                 240
Leu Pro Thr Glu Ala Leu Ala Pro Leu Arg Ala Leu Gln Tyr Leu Arg
                245                 250                 255
Leu Asn Asp Asn Pro Trp Val Cys Asp Cys Arg Ala Arg Pro Leu Trp
            260                 265                 270
Ala Trp Leu Gln Lys Phe Arg Gly Ser Ser Ser Glu Val Pro Cys Ser
        275                 280                 285
Leu Pro Gln Arg Leu Ala Gly Arg Asp Leu Lys Arg Leu Ala Ala Asn
    290                 295                 300
Asp Leu Gln Gly Cys Ala Val Ala Thr Gly Pro Tyr His Pro Ile Trp
305                 310                 315                 320
Thr Gly Arg Ala Thr Asp Glu Glu Pro Leu Gly Leu Pro Lys Cys Cys
                325                 330                 335
Gln Pro Asp Ala Ala Asp Lys Ala Ser Val Leu Glu Pro Gly Arg Pro
            340                 345                 350
Ala Ser Ala Gly Asn Ala Leu Lys Gly Arg Val Pro Gly Gly Asp Ser
        355                 360                 365
Pro Pro Gly Asn Gly Ser Gly Pro Arg His Ile Asn Asp Ser Pro Phe
    370                 375                 380
Gly Thr Leu Pro Gly Ser Ala Glu Pro Pro Leu Thr Ala Val Arg Pro
385                 390                 395                 400
Glu Gly Ser Glu Pro Pro Gly Phe Pro Thr Ser Gly Pro Arg Arg Arg
                405                 410                 415
Pro Gly Cys Ser Arg Lys Asn Arg Thr Arg Ser His Cys Arg Leu Gly
            420                 425                 430
Gln Ala Gly Ser Gly Gly Gly Gly Thr Gly Asp Ser Glu Gly Ser Gly
        435                 440                 445
Ala Leu Pro Ser Leu Thr Cys Ser Leu Thr Pro Leu Gly Leu Ala Leu
    450                 455                 460
Val Leu Trp Thr Val Leu Gly Pro Cys           SEQ ID NO:8
465                 470
```

FIG. 7

```
Met Lys Arg Ala Ser Ser Gly Gly Ser Arg Leu Leu Ala Trp Val Leu
 1           5               10                  15
Trp Leu Gln Ala Trp Arg Val Ala Thr Pro Cys Pro Gly Ala Cys Val
         20              25              30
Cys Tyr Asn Glu Pro Lys Val Thr Thr Ser Cys Pro Gln Gly Leu
         35              40              45
Gln Ala Val Pro Thr Gly Ile Pro Ala Ser Ser Gln Arg Ile Phe Leu
     50              55              60
His Gly Asn Arg Ile Ser His Val Pro Ala Ala Ser Phe Gln Ser Cys
 65              70              75              80
Arg Asn Leu Thr Ile Leu Trp Leu His Ser Asn Ala Leu Ala Arg Ile
             85              90              95
Asp Ala Ala Ala Phe Thr Gly Leu Thr Leu Leu Glu Gln Leu Asp Leu
         100             105             110
Ser Asp Asn Ala Gln Leu His Val Val Asp Pro Thr Thr Phe His Gly
     115             120             125
Leu Gly His Leu His Thr Leu His Leu Asp Arg Cys Gly Leu Arg Glu
 130             135             140
Leu Gly Pro Gly Leu Phe Arg Gly Leu Ala Ala Leu Gln Tyr Leu Tyr
145             150             155             160
Leu Gln Asp Asn Asn Leu Gln Ala Leu Pro Asp Asn Thr Phe Arg Asp
             165             170             175
Leu Gly Asn Leu Thr His Leu Phe Leu His Gly Asn Arg Ile Pro Ser
         180             185             190
Val Pro Glu His Ala Phe Arg Gly Leu His Ser Leu Asp Arg Leu Leu
         195             200             205
Leu His Gln Asn His Val Ala Arg Val His Pro His Ala Phe Arg Asp
     210             215             220
Leu Gly Arg Leu Met Thr Leu Tyr Leu Phe Ala Asn Asn Leu Ser Met
225             230             235             240
Leu Pro Ala Glu Val Leu Met Pro Leu Arg Ser Leu Gln Tyr Leu Arg
             245             250             255
Leu Asn Asp Asn Pro Trp Val Cys Asp Cys Arg Ala Arg Pro Leu Trp
         260             265             270
Ala Trp Leu Gln Lys Phe Arg Gly Ser Ser Ser Glu Val Pro Cys Asn
         275             280             285
Leu Pro Gln Arg Leu Ala Asp Arg Asp Leu Lys Arg Leu Ala Ala Ser
     290             295             300
Asp Leu Glu Gly Cys Ala Val Ala Ser Gly Pro Phe Arg Pro Ile Gln
305             310             315             320
Thr Ser Gln Leu Thr Asp Glu Leu Leu Ser Leu Pro Lys Cys Cys
             325             330             335
Gln Pro Asp Ala Ala Asp Lys Ala Ser Val Leu Glu Pro Gly Arg Pro
         340             345             350
Ala Ser Ala Gly Asn Ala Leu Lys Gly Arg Val Pro Pro Gly Asp Thr
     355             360             365
Pro Pro Gly Asn Gly Ser Gly Pro Arg His Ile Asn Asp Ser Pro Phe
370             375             380
Gly Thr Leu Pro Ser Ser Ala Glu Pro Pro Leu Thr Ala Leu Arg Pro
385             390             395             400
Gly Gly Ser Glu Pro Pro Gly Leu Pro Thr Thr Gly Pro Arg Arg Arg
             405             410             415
Pro Gly Cys Ser Arg Lys Asn Arg Thr Arg Ser His Cys Arg Leu Gly
         420             425             430
Gln Ala Gly Ser Gly Ala Ser Gly Thr Gly Asp Ala Glu Gly Ser Gly
     435             440             445
Ala Leu Pro Ala Leu Ala Cys Ser Leu Ala Pro Leu Gly Leu Ala Leu
450             455             460
Val Leu Trp Thr Val Leu Gly Pro Cys       SEQ ID NO:9
465             470
```

FIG. 8

```
Met Lys Arg Ala Ser Ala Gly Gly Ser Arg Leu Leu Ala Trp Val Leu
 1           5                    10                   15
Trp Leu Gln Ala Trp Gln Val Ala Ala Pro Cys Pro Gly Ala Cys Val
            20                   25                   30
Cys Tyr Asn Glu Pro Lys Val Thr Thr Ser Cys Pro Gln Gln Gly Leu
            35                   40                   45
Gln Ala Val Pro Val Gly Ile Pro Ala Ala Ser Gln Arg Ile Phe Leu
        50                   55                   60
His Gly Asn Arg Ile Ser His Val Pro Ala Ala Ser Phe Arg Ala Cys
 65                   70                   75                   80
Arg Asn Leu Thr Ile Leu Trp Leu His Ser Asn Val Leu Ala Arg Ile
                 85                   90                   95
Asp Ala Ala Ala Phe Thr Gly Leu Ala Leu Leu Glu Gln Leu Asp Leu
            100                  105                  110
Ser Asp Asn Ala Gln Leu Arg Ser Val Asp Pro Ala Thr Phe His Gly
        115                  120                  125
Leu Gly Arg Leu His Thr Leu His Leu Asp Arg Cys Gly Leu Gln Glu
    130                  135                  140
Leu Gly Pro Gly Leu Phe Arg Gly Leu Ala Ala Leu Gln Tyr Leu Tyr
145                  150                  155                  160
Leu Gln Asp Asn Ala Leu Gln Ala Leu Pro Asp Asp Thr Phe Arg Asp
            165                  170                  175
Leu Gly Asn Leu Thr His Leu Phe Leu His Gly Asn Arg Ile Ser Ser
        180                  185                  190
Val Pro Glu Arg Ala Phe Arg Gly Leu His Ser Leu Asp Arg Leu Leu
    195                  200                  205
Leu His Gln Asn Arg Val Ala His Val His Pro His Ala Phe Arg Asp
210                  215                  220
Leu Gly Arg Leu Met Thr Leu Tyr Leu Phe Ala Asn Asn Leu Ser Ala
225                  230                  235                  240
Leu Pro Thr Glu Ala Leu Ala Pro Leu Arg Ala Leu Gln Tyr Leu Arg
            245                  250                  255
Leu Asn Asp Asn Pro Trp Val Cys Asp Cys Arg Ala Arg Pro Leu Trp
        260                  265                  270
Ala Trp Leu Gln Lys Phe Arg Gly Ser Ser Ser Glu Val Pro Cys Ser
    275                  280                  285
Leu Pro Gln Arg Leu Ala Gly Arg Asp Leu Lys Arg Leu Ala Ala Asn
290                  295                  300
Asp Leu Gln Gly Cys Ala Val Ala Thr Gly Pro Tyr His Pro Ile Trp
305                  310                  315                  320
Thr Gly Arg Ala Thr Asp Glu Glu Pro Leu Gly Leu Pro Lys Cys Cys
            325                  330                  335
Gln Pro Asp Ala Ala Asp Lys Ala     SEQ ID NO: 10 (Human 1-344)
            340
```

FIG. 8 (CONT.)

```
Met Lys Arg Ala Ser Ala Gly Gly Ser Arg Leu Leu Ala Trp Val Leu
 1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
 65                 70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
            165                 170                 175

Leu Gly Asn Leu Thr His Leu Phe Leu His Gly Asn Arg Ile Ser Ser
        180                 185                 190

Val Pro Glu Arg Ala Phe Arg Gly Leu His Ser Leu Asp Arg Leu Leu
    195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
            245                 250                 255

Leu Asn Asp Asn Pro Trp Val Cys Asp Cys Arg Ala Arg Pro Leu Trp
        260                 265                 270

Ala Trp Leu Gln Lys Phe Arg Gly Ser Ser Ser Glu Val Pro Cys Ser
    275                 280                 285

Leu Pro Gln Arg Leu Ala Gly Arg Asp Leu Lys Arg Leu Ala Ala Asn
    290                 295                 300

Asp Leu Gln Gly Cys Ala       SEQ ID NO: 11 (Human 1-310)
305                 310
```

FIG. 8 (CONT.)

```
Met Lys Arg Ala Ser Ser Gly Gly Ser Arg Leu Pro Thr Trp Val Leu
 1           5               10                  15
Trp Leu Gln Ala Trp Arg Val Ala Thr Pro Cys Pro Gly Ala Cys Val
             20              25                  30
Cys Tyr Asn Glu Pro Lys Val Thr Thr Ser Arg Pro Gln Gln Gly Leu
         35              40                  45
Gln Ala Val Pro Ala Gly Ile Pro Ala Ser Ser Gln Arg Ile Phe Leu
     50              55                  60
His Gly Asn Arg Ile Ser Tyr Val Pro Ala Ala Ser Phe Gln Ser Cys
 65              70                  75              80
Arg Asn Leu Thr Ile Leu Trp Leu His Ser Asn Ala Leu Ala Gly Ile
             85                  90                  95
Asp Ala Ala Ala Phe Thr Gly Leu Thr Leu Leu Glu Gln Leu Asp Leu
            100                 105                 110
Ser Asp Asn Ala Gln Leu Arg Val Val Asp Pro Thr Thr Phe Arg Gly
            115             120                 125
Leu Gly His Leu His Thr Leu His Leu Asp Arg Cys Gly Leu Gln Glu
    130                 135                 140
Leu Gly Pro Gly Leu Phe Arg Gly Leu Ala Ala Leu Gln Tyr Leu Tyr
145                 150                 155                 160
Leu Gln Asp Asn Asn Leu Gln Ala Leu Pro Asp Asn Thr Phe Arg Asp
                165                 170                 175
Leu Gly Asn Leu Thr His Leu Phe Leu His Gly Asn Arg Ile Pro Ser
            180                 185                 190
Val Pro Glu His Ala Phe Arg Gly Leu His Ser Leu Asp Arg Leu Leu
        195                 200                 205
Leu His Gln Asn His Val Ala Arg Val His Pro His Ala Phe Arg Asp
    210                 215                 220
Leu Gly Arg Leu Met Thr Leu Tyr Leu Phe Ala Asn Asn Leu Ser Met
225                 230                 235                 240
Leu Pro Ala Glu Val Leu Val Pro Leu Arg Ser Leu Gln Tyr Leu Arg
                245                 250                 255
Leu Asn Asp Asn Pro Trp Val Cys Asp Cys Arg Ala Arg Pro Leu Trp
            260                 265                 270
Ala Trp Leu Gln Lys Phe Arg Gly Ser Ser Ser Gly Val Pro Ser Asn
        275                 280                 285
Leu Pro Gln Arg Leu Ala Gly Arg Asp Leu Lys Arg Leu Ala Thr Ser
    290                 295                 300
Asp Leu Glu Gly Cys Ala Val Ala Ser Gly Pro Phe Arg Pro Phe Gln
305                 310                 315                 320
Thr Asn Gln Leu Thr Asp Glu Glu Leu Leu Gly Leu Pro Lys Cys Cys
                325                 330                 335
Gln Pro Asp Ala Ala Asp Lys Ala      SEQ ID NO: 12 (Rat 1-344)
            340
```

FIG. 8 (CONT.)

```
Met Lys Arg Ala Ser Ser Gly Gly Ser Arg Leu Pro Thr Trp Val Leu
 1           5                   10                  15

Trp Leu Gln Ala Trp Arg Val Ala Thr Pro Cys Pro Gly Ala Cys Val
             20                  25                  30

Cys Tyr Asn Glu Pro Lys Val Thr Thr Ser Arg Pro Gln Gln Gly Leu
         35                  40                  45

Gln Ala Val Pro Ala Gly Ile Pro Ala Ser Ser Gln Arg Ile Phe Leu
     50                  55                  60

His Gly Asn Arg Ile Ser Tyr Val Pro Ala Ala Ser Phe Gln Ser Cys
 65                  70                  75                  80

Arg Asn Leu Thr Ile Leu Trp Leu His Ser Asn Ala Leu Ala Gly Ile
                 85                  90                  95

Asp Ala Ala Ala Phe Thr Gly Leu Thr Leu Leu Glu Gln Leu Asp Leu
             100                 105                 110

Ser Asp Asn Ala Gln Leu Arg Val Val Asp Pro Thr Thr Phe Arg Gly
         115                 120                 125

Leu Gly His Leu His Thr Leu His Leu Asp Arg Cys Gly Leu Gln Glu
     130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                 165                 170                 175

Leu Gly Asn Leu Thr His Leu Phe Leu His Gly Asn Arg Ile Pro Ser
             180                 185                 190

Val Pro Glu His Ala Phe Arg Gly Leu His Ser Leu Asp Arg Leu Leu
         195                 200                 205

Leu His Gln Asn His Val Ala Arg Val His Pro His Ala Phe Arg Asp
     210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                 245                 250                 255

Leu Asn Asp Asn Pro Trp Val Cys Asp Cys Arg Ala Arg Pro Leu Trp
             260                 265                 270

Ala Trp Leu Gln Lys Phe Arg Gly Ser Ser Gly Val Pro Ser Asn
         275                 280                 285

Leu Pro Gln Arg Leu Ala Gly Arg Asp Leu Lys Arg Leu Ala Thr Ser
     290                 295                 300

Asp Leu Glu Gly Cys Ala          SEQ ID NO: 13  (Rat  1-310)
305             310
```

```
Arg Ile Tyr Lys Gly Val Ile Gln Ala Ile Gln Lys Ser Asp Glu Gly
 1               5                  10                  15
His Pro Phe Arg Ala Tyr Leu Glu Ser Glu Val Ala Ile Ser Glu Glu
            20                  25                  30
Leu Val Gln Lys Tyr Ser Asn Ser Ala Leu Gly His Val Asn Cys Thr
            35                  40                  45
Ile Lys Glu Leu Arg Arg Leu Phe Leu Val Asp Asp Leu Val Asp Ser
     50                  55                  60
Leu Lys    SEQ ID NO:14
 65
```

```
Arg Ile Tyr Lys Gly Val Ile Gln Ala Ile Gln Lys Ser Asp Glu Gly
 1               5                  10                  15
His Pro Phe Arg Ala Tyr Leu Glu Ser Glu Val Ala Ile Ser Glu Glu
            20                  25                  30
Leu Val Gln Lys Tyr Ser Asn Ser    SEQ ID NO:15
            35                  40
```

```
Arg Ile Tyr Lys Gly Val Ile Gln Lys Ser Asp Glu Gly His Pro Phe
 1               5                  10                  15
Arg Ala Tyr Leu Glu Ser Glu Val Ala Ile Ser Glu Glu Leu Val Gln
            20                  25                  30
Lys Tyr Ser Asn Ser    SEQ ID NO:16
            35
```

*FIG. 9*

BDA INJECTION COORDINATES (RELATIVE TO BREGMA)

| INJECTION # | A/P POSITION | M/L POSITION |
|---|---|---|
| 1 | 0.22 | 0.28 |
| 2 | 0.17 | 0.23 |
| 3 | 0.12 | 0.23 |
| 4 | 0.12 | 0.29 |
| 5 | 0.07 | 0.19 |
| 6 | 0.07 | 0.25 |
| 7 | 0.07 | 0.31 |
| 8 | 0.02 | 0.13 |
| 9 | 0.02 | 0.21 |
| 10 | -0.03 | 0.15 |
| 11 | -0.03 | 0.23 |
| 12 | -0.08 | 0.13 |
| 13 | -0.08 | 0.21 |
| 14 | -0.13 | 0.13 |
| 15 | -0.13 | 0.21 |
| 16 | -0.18 | 0.15 |
| 17 | -0.18 | 0.23 |
| 18 | -0.23 | 0.21 |

*FIG. 15C*

SEQUENCE LISTING

```
<160> NUMBER OF SEQ ID NOS: 18

<210> SEQ ID NO 1
<211> LENGTH: 40
<212> TYPE: PRT
<213> ORGANISM: Homo sapiens

<400> SEQUENCE: 1

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Val Ala Ile Ser Glu Glu
             20                  25                  30

Leu Val Gln Lys Tyr Ser Asn Ser
         35                  40

<210> SEQ ID NO 2
<211> LENGTH: 25
<212> TYPE: PRT
<213> ORGANISM: Homo sapiens

<400> SEQUENCE: 2

Ile Gln Lys Ser Asp Glu Gly His Pro Phe Arg Ala Tyr Leu Glu Ser
  1               5                  10                  15

Glu Val Ala Ile Ser Glu Glu Leu Val
             20                  25

<210> SEQ ID NO 3
<211> LENGTH: 25
<212> TYPE: PRT
<213> ORGANISM: Homo sapiens

<400> SEQUENCE: 3

Arg Ala Tyr Leu Glu Ser Glu Val Ala Ile Ser Glu Glu Leu Val Gln
  1               5                  10                  15

Lys Tyr Ser Asn Ser Ala Leu Gly His
             20                  25
```

```
<210> SEQ ID NO 4
<211> LENGTH: 25
<212> TYPE: PRT
<213> ORGANISM: Homo sapiens

<400> SEQUENCE: 4

Ser Glu Glu Leu Val Gln Lys Tyr Ser Asn Ser Ala Leu Gly His Val
 1               5                  10                  15

Asn Cys Thr Ile Lys Glu Leu Arg Arg
            20                  25

<210> SEQ ID NO 5
<211> LENGTH: 25
<212> TYPE: PRT
<213> ORGANISM: Homo sapiens

<400> SEQUENCE: 5

Ala Leu Gly His Val Asn Cys Thr Ile Lys Glu Leu Arg Arg Leu Phe
 1               5                  10                  15

Leu Val Asp Asp Leu Val Asp Ser Leu
            20                  25

<210> SEQ ID NO 6
<211> LENGTH: 40
<212> TYPE: PRT
<213> ORGANISM: Homo sapiens

<400> SEQUENCE: 6

Arg Ile Tyr Lys Gly Val Ile Gln Ala Ile Gln Lys Ser Asp Glu Gly
 1               5                  10                  15

His Pro Phe Arg Ala Tyr Leu Glu Ser Glu Val Ala Ile Ser Glu Glu
            20                  25                  30

Leu Val Gln Lys Tyr Ser Asn Ser
        35                  40

<210> SEQ ID NO 7
<211> LENGTH: 66
<212> TYPE: PRT
<213> ORGANISM: Homo sapiens

<400> SEQUENCE: 7

Phe Arg Ile Tyr Lys Gly Val Ile Gln Ala Ile Gln Lys Ser Asp Glu
 1               5                  10                  15

Gly His Pro Phe Arg Ala Tyr Leu Glu Ser Glu Val Ala Ile Ser Glu
            20                  25                  30

Glu Leu Val Gln Lys Tyr Ser Asn Ser Ala Leu Gly His Val Asn Cys
        35                  40                  45

Thr Ile Lys Glu Leu Arg Arg Leu Phe Leu Val Asp Asp Leu Val Asp
     50                  55                  60

Ser Leu
 65

<210> SEQ ID NO 8
<211> LENGTH: 473
<212> TYPE: PRT
<213> ORGANISM: Homo sapiens
```

<400> SEQUENCE: 8

```
Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Glu Gln Leu Asp Leu
             100                 105                 110

Ser Asp Asn Ala Gln Leu Arg Ser Val Asp Pro Ala Thr Phe His Gly
         115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Leu Thr Ala Val Arg Pro
385                 390                 395                 400

Glu Gly Ser Glu Pro Pro Gly Phe Pro Thr Ser Gly Pro Arg Arg Arg
                405                 410                 415
```

```
Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 9
<211> LENGTH: 473
<212> TYPE: PRT
<213> ORGANISM: Mus musculus

<400> SEQUENCE: 9

Met Lys Arg Ala Ser Ser Gly Gly Ser Arg Leu Leu Ala Trp Val Leu
  1               5                  10                  15

Trp Leu Gln Ala Trp Arg Val Ala Thr Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Thr Gly Ile Pro Ala Ser Ser Gln Arg Ile Phe Leu
     50                  55                  60

His Gly Asn Arg Ile Ser His Val Pro Ala Ala Ser Phe Gln Ser Cys
 65                  70                  75                  80

Arg Asn Leu Thr Ile Leu Trp Leu His Ser Asn Ala Leu Ala Arg Ile
                 85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Asp Arg Asp Leu Lys Arg Leu Ala Ala Ser
    290                 295                 300

Asp Leu Glu Gly Cys Ala Val Ala Ser Gly Pro Phe Arg Pro Ile Gln
305                 310                 315                 320
```

```
Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
            405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470

<210> SEQ ID NO 10
<211> LENGTH: 344
<212> TYPE: PRT
<213> ORGANISM: Homo sapiens

<400> SEQUENCE: 10

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220
```

```
Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala
            340

<210> SEQ ID NO 11
<211> LENGTH: 310
<212> TYPE: PRT
<213> ORGANISM: Homo sapiens

<400> SEQUENCE: 11

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
                20                  25                  30

Cys Tyr Asn Glu Pro Lys Val Thr Thr Ser Cys Pro Gln Gln Gly Leu
            35                  40                  45

Gln Ala Val Pro Val Gly Ile Pro Ala Ala Ser Gln Arg Ile Phe Leu
        50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255
```

Leu Asn Asp Asn Pro Trp Val Cys Asp Cys Arg Ala Arg Pro Leu Trp
            260                 265                 270

Ala Trp Leu Gln Lys Phe Arg Gly Ser Ser Glu Val Pro Cys Ser
        275                 280                 285

Leu Pro Gln Arg Leu Ala Gly Arg Asp Leu Lys Arg Leu Ala Ala Asn
290                 295                 300

Asp Leu Gln Gly Cys Ala
305             310

<210> SEQ ID NO 12
<211> LENGTH: 344
<212> TYPE: PRT
<213> ORGANISM: Rattus norvegicus

<400> SEQUENCE: 12

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Arg Pro Gln Gln Gly Leu
        35                  40                  45

Gln Ala Val Pro Ala Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Cys Ala Val Ala Ser Gly Pro Phe Arg Pro Phe Gln
305                 310                 315                 320

```
Thr Asn Gln Leu Thr Asp Glu Glu Leu Leu Gly Leu Pro Lys Cys Cys
                325                 330                 335

Gln Pro Asp Ala Ala Asp Lys Ala
            340
```

<210> SEQ ID NO 13
<211> LENGTH: 310
<212> TYPE: PRT
<213> ORGANISM: Rattus norvegicus

<400> SEQUENCE: 13

```
Met Lys Arg Ala Ser Ser Gly Gly Ser Arg Leu Pro Thr Trp Val Leu
  1               5                  10                  15

Trp Leu Gln Ala Trp Arg Val Ala Thr Pro Cys Pro Gly Ala Cys Val
             20                  25                  30

Cys Tyr Asn Glu Pro Lys Val Thr Ser Arg Pro Gln Gln Gly Leu
             35                  40                  45

Gln Ala Val Pro Ala Gly Ile Pro Ala Ser Ser Gln Arg Ile Phe Leu
         50                  55                  60

His Gly Asn Arg Ile Ser Tyr Val Pro Ala Ala Ser Phe Gln Ser Cys
 65                  70                  75                  80

Arg Asn Leu Thr Ile Leu Trp Leu His Ser Asn Ala Leu Ala Gly Ile
                 85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
    290                 295                 300

Asp Leu Glu Gly Cys Ala
305                 310
```

<210> SEQ ID NO 14
<211> LENGTH: 66
<212> TYPE: PRT
<213> ORGANISM: Homo sapiens

```
<400> SEQUENCE: 14

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Val Ala Ile Ser Glu Glu
             20                  25                  30

Leu Val Gln Lys Tyr Ser Asn Ser Ala Leu Gly His Val Asn Cys Thr
         35                  40                  45

Ile Lys Glu Leu Arg Arg Leu Phe Leu Val Asp Asp Leu Val Asp Ser
 50                  55                  60

Leu Lys
 65

<210> SEQ ID NO 15
<211> LENGTH: 40
<212> TYPE: PRT
<213> ORGANISM: Homo sapiens

<400> SEQUENCE: 15

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Val Ala Ile Ser Glu Glu
             20                  25                  30

Leu Val Gln Lys Tyr Ser Asn Ser
         35                  40

<210> SEQ ID NO 16
<211> LENGTH: 37
<212> TYPE: PRT
<213> ORGANISM: Homo sapiens

<400> SEQUENCE: 16

Arg Ile Tyr Lys Gly Val Ile Gln Lys Ser Asp Glu Gly His Pro Phe
  1               5                  10                  15

Arg Ala Tyr Leu Glu Ser Glu Val Ala Ile Ser Glu Glu Leu Val Gln
             20                  25                  30

Lys Tyr Ser Asn Ser
         35

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 17
tatggctagc tatgcacata ctttcacaga att                               33

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 18
ctatttaaat atcattgctg taatcataat ttgtc                             35
```

METHOD FOR TREATING STROKE VIA ADMINISTRATION OF NEP1-40 AND INOSINE

CROSS REFERENCE

This Application is a Continuation-in-Part application of U.S. application Ser. No. 10/580,364, filed Dec. 14, 2006, pending, which is a 35 U.S.C. §371 National Stage of International Application No. PCT/US2004/042255, filed on Dec. 16, 2004, which designates the United States, which claims the benefit of priority under 35 U.S.C §119(e) of U.S. Provisional Application No. 60/529,833, filed Dec. 16, 2003, the contents of each of which are incorporated herein in their entirety.

GOVERNMENT SUPPORT

The work described herein was supported, in part, by National Institute of Health grant No. EY05690, R01 NS047446, and P30 HD018655. The U.S. Government has certain rights to the invention.

BACKGROUND OF THE INVENTION

The inability of CNS neurons to regenerate their axons after injury places severe limitations on the functional recovery that can occur after traumatic injury, stroke, or certain neurodegenerative diseases. Regenerative failure has been attributed in part to proteins associated with CNS myelin and with glial scar that forms at an injury site. Several myelin inhibitors of axon growth, including the C-terminal of NogoA (Chen et al., 2000; GrandPre et al., 2000), myelin-associated glycoprotein, (McKerracher et al., 1994; Mukhopadhyay et al., 1994), and OMgp (Wang et al., 2002b), exert their effects via the Nogo receptor (NgR) and p75$^{NTR}$ or another co-receptor (Fournier et al., 2001; Domeniconi et al., 2002; Liu et al., 2002; Wang et al., 2002a,b). In culture, expression of NgR causes growth cones of embryonic chick retinal ganglion cells (RGCs) to collapse upon contact with the C-terminal region of Nogo (Nogo66) (Fournier et al., 2001) and inhibits neurite outgrowth from cerebellar granule cells on MAG, OMgp, or myelin (Wang et al., 2002a,b). Conversely, transfection with dominant-negative form of NgR (NgR$^{DN}$) enables cerebellar granule cells in culture to overcome the inhibitory effects of myelin, Nogo66, OMgp, and MAG (Domeniconi et al., 2002; Wang et al., 2002a,b). However, the effects of overexpressing either NgR or NgR$^{DN}$ have not been investigated in vivo, nor have the effects of deleting the gene.

Antibodies to NogoA, or a small peptide inhibitor of NgR, increase corticospinal tract (CST) regeneration only to some extent in rats (Schnell et al., 1994; Bregman et al., 1995; GrandPre et al., 2002; Sicotte et al., 2003), whereas genetic deletion of the NogoA gene in mice results either in a modest CST regeneration (Kim et al., 2003b; Simonen et al., 2003) or in none (Zheng et al., 2003). Thus, overcoming specific myelin inhibitors, or suppression of signaling through NgR, is not sufficient to promote the substantive CNS regeneration in vivo that would be required for the treatment of neurological disorders (Steward et al., 2003; Woolf, 2003; Zheng et al., 2003).

There is a need in the art for methods and compositions that can improve the ability of a neuron, or portion of the nervous system, to regenerate, and to maintain desirable function, which can be used for treatment of neurological disorders.

SUMMARY OF THE INVENTION

The present invention is based on the discovery that suppressing the activity of the Nogo receptor (NgR) alone does not result in extensive axon regeneration unless the innate growth pathway of neurons is also activated. Accordingly, the present invention is directed to methods of stimulating axon regeneration using a combination therapy wherein agents that inhibit NgR activity are combined with agents that activate the growth pathway of neurons (e.g. polypeptide growth factors, e.g., BDNF, CNTF, NGF, IL-6, GDNF; activators of macrophages, such as GM-CSF, TGF-β; growth factors produced by macrophages, e.g., oncomodulin or MIF; purine nucleosides, such as inosine; or hexoses, such as mannose).

In one embodiment, a method for stimulating the axonal growth of central nervous system (CNS) neurons is provided comprising the steps of i) contacting CNS neurons with an effective amount of an NgR antagonist; and ii) contacting CNS neurons with an effective amount of an agent that activates the growth pathway of CNS neurons.

Neurons can be contacted with each agent either separately or simultaneously. In one preferred embodiment, neurons are contacted with an agent that activates the growth pathway of CNS neurons prior to contacting with an NgR antagonist.

Examples of suitable agents that can be used for activation of the growth pathway of CNS neurons in the present invention include, but are not limited to, inosine, oncomodulin, known polypeptide growth factors such as NGF, NT-3, NGF, CNTF, IL-6, GDNF, TGF-β and hexose molecules, such as D-mannose, gulose and glucose-6-phosphate.

In one aspect, the method for stimulating the axonal growth of central nervous system (CNS) neurons, as described herein, further comprises contacting CNS neurons with a cAMP modulator that increases the concentration of intracellular cAMP. Suitable cAMP modulators for use in the present invention include, but are not limited to cAMP analogues, activators of G protein coupled receptors that activate cAMP, adenylate cyclase activators, calcium ionophores, and phosphodiesterase inhibitors.

Suitable NgR antagonist for use in the present invention include any agent able to suppress the activity of the Nogo receptor. For example, the NgR antagonist can be an agent that binds to the Nogo receptor thereby inhibiting signaling mediated by NgR, an agent that binds to a ligand of NgR (e.g. OMgp, MAG, or NOGO) thereby inhibiting binding of the ligand to NgR, an agent that inhibits the expression of NgR, or an agent that inhibits the activity of a downstream signaling molecule that is activated by NgR, such as RhoA or Rho kinase (ROCK). NgR antagonists can be antibodies, peptides, a small molecules, RNAs (e.g. siRNA or antisense-RNA), or DNAs.

In the methods described herein, any combination of an NgR antagonist and an agent that activates the growth pathway of CNS neurons can be used.

In one embodiment, the NgR antagonist is a peptide that binds to NgR, said peptide being selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7.

In one embodiment, the NgR antagonist is a peptide that comprises the amino acid residues of human NogoA set forth in SEQ ID NO: 14.

In one embodiment, the NgR antagonist is a peptide that comprises the amino acid residues of human NogoA forth in SEQ ID NO: 15.

In one embodiment, the NgR antagonist is a peptide that comprises the amino acid sequence of Nogo-66 set forth in SEQ ID NO: 16.

In another embodiment, the NgR antagonist is a soluble NgR protein.

In one embodiment, the soluble NgR protein comprises the amino acid sequence set forth in SEQ ID NO: 8 or in SEQ ID NO: 9.

In one embodiment, the soluble NgR protein is a soluble Nogo Receptor-1 polypeptide sequence selected from the group consisting of amino acid residues 26-344 of SEQ ID NO: 10; amino acid residues 26-310 of SEQ ID NO: 11; amino acid residues 26-344 of SEQ ID NO: 12; amino acid residues 27-344 of SEQ ID NO: 12; and amino acid residues 27-310 of SEQ ID NO: 13.

In another embodiment, the NgR antagonist is a nucleic acid aptamer that binds to NgR.

In one embodiment, the NgR antagonist is a DNA that encodes a dominant negative form of NgR. The DNA can be contained in a viral vector (e.g. AAV) whereby administration of said vector is a means for contacting CNS neurons with an effective amount of NgR antagonist. Any viral vector can be used in the methods of the present invention.

In one embodiment, the NgR antagonist is an agent that inhibits the activity of a downstream signaling molecule that is activated by NgR, such as clostridium botulinum C3 ADP-ribosyltransferase that inhibits the downstream signaling molecule RhoA.

In another embodiment, a method for treating a neurological disorder in a patient is provided that comprises the steps of i) administering an effective amount of an NgR antagonist to a patient; and ii) administering to said patient an effective amount of an agent that activates the growth pathway of CNS neurons.

Any neurological disorder that would benefit from new axonal growth can be treated by the methods of the present invention.

In one embodiment, the neurological disorder to be treated is selected from the following: traumatic brain injury, stroke, cerebral aneurism, spinal cord injury, Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, ophthalmoplegia, and retina or optic nerve damage.

Pharmaceutical compositions comprising a NgR antagonist and an agent that activates the growth pathway of CNS neurons is also provided. The composition is formulated for administration, including, for example topical, pulmonary, internal topical, interdermal, parenteral, subcutaneous, intranasal, epidermal, ophthalmic, oral, intraventricular, and intrathecal administration.

In one embodiment, the invention includes a kit having a container of an NgR antagonist and a container of an agent that activates the growth pathway of CNS neurons.

BRIEF DESCRIPTION OF FIGURES

FIG. 3 shows that activation of the growth pathway of RGCs and inactivation of RhoA have synergistic effects in vivo. GAP-43-positive axons visualized in longitudinal sections through the adult rat optic nerve 2 weeks after axotomy with or without lens injury. RGCs were transfected with AAV expressing GFP alone or C3 plus GFP.a, Absence of regeneration after axotomy alone.

FIG. 5 shows SEQ ID NO: 1, SEQ ID NO: 2, SEQ ID NO: 3, SEQ ID NO: 4, SEQ ID NO: 5, SEQ ID NO: 6, and SEQ ID NO: 7.

FIG. 6 shows SEQ ID NO: 8.

FIG. 7 shows SEQ ID NO: 9.

FIG. 8 shows SEQ ID NO: 10, SEQ ID NO: 11, SEQ ID NO: 12, and SEQ ID NO: 13.

FIG. 9 shows SEQ ID NO: 14, SEQ ID NO: 15, and SEQ ID NO: 16.

FIG. 10A: Extent of the smallest (dark gray), average (medium gray), and largest (light gray) lesions in saline-(left) and inosine-(right) treated animals 4 weeks after induction of focal ischemia. FIG. 10B: Volumetric analyses reveal no between-group differences in average lesion size.

FIG. 11A and FIG. 11A' are low magnification camera lucida drawings of BDA-labeled CST fibers that originate in the uninjured hemisphere and project to the side of the spinal cord denervated by unilateral cortical injury. Rats were treated with either saline-(A) or inosine (A'). FIG. 11B and FIG. 11B' are high-magnification photomicrographs of fibers in the grey matter of saline-(B) and inosine-(B') treated rats. FIG. 11C and FIG. 11C' are camera lucida tracings of the fibers in B and B'. FIG. 11D and FIG. 11D' (insets), are higher magnification views of bouton-like structures. FIG. 11E and FIG. 11F, are bar graphs showing quantitation of ipsilaterally projecting CST fibers ≥40 μm in length in the transverse plane in the denervated dorsal funiculus and gray matter, respectively. FIG. 11G is a bar graph showing quantitation of ipsilaterally projecting CST fibers ≥200 μm in length in the denervated gray matter. FIG. 11H is a bar graph showing quantitation of bouton-like swellings on fibers projecting to the ipsilateral spinal gray matter visualized under a 100× oil objective. Results in FIGS. 11E-11G are normalized by the intensity of staining in the intact CST and are reported as number of labeled axons per mm length of spinal cord. **Difference between groups significant at $P<0.01$. Error bars represent SEM.

FIG. 12A, Inosine improves functional recovery using the impaired paw. FIG. 12B, Animals show normal performance with the unim-paired paw after 2 weeks irrespective of treatment. *, , *: Differences significant at $P<0.05$, $P<0.01$, $P<0.001$, respectively. Error bars represent SEM.

FIG. 13B shows performance with the paw ipsilateral to the stroke is unaffected by treatment. *, , *: Differences between groups significant at $P<0.05$, $P<0.01$, $P<0.001$, respectively. Arrows indicate time of pump removal.

FIG. 14A is a heat-map showing patterns of changes induced by stroke alone (stroke+saline) and by inosine treatment after stroke (stroke+inosine). Only genes with statistically significant ($P<0.01$) changes ≥1.7× above or below baseline level of expression are shown. Inset shows scheme for the magnitude of changes. FIG. 14B is a pie chart showing numbers of genes exhibiting different patterns of change after stroke. Most changes follow the trend of being up- or down-regulated after stroke and attenuated (atten.) by inosine. A smaller number of genes are not significantly changed by stroke but are either up- or down-regulated by inosine, and an even smaller number are changed by stroke and changed further in the same direction by inosine. FIG. 14C is a scatter diagram showing effect of inosine in attenuating stroke-induced changes. Data include only those genes whose expression is significantly altered by stroke. Data are plotted as the log 2 change in expression after stroke in animals treated with inosine vs. saline (y-axis) against the log 2 change in expression after stroke alone (and treatment with saline) vs. normal controls. Trend line has a slope of −0.49 and correlation coefficient of 0.87, signifying that inosine attenuates most of the stroke-induced changes. FIG. 14D is a scatter diagram similar to that of FIG. 14C, but showing all data points. Points that fall significantly off the trend line ($P<0.01$, red dots) correspond to genes that are affected by inosine over and above attenuating the stroke-induced changes.

FIG. 15A-FIG. 15C shows example of lesions and BDA labeling. FIG. 15A is a photomicrograph of a section through the rat brain at the level of the primary motor cortex. The lesion is on the right side of the section, while the left side shows the extent of BDA labeling at this level. FIG. 15B is a line drawing of the section shown in a indicating location of the primary motor cortex (M1). FIG. 15C is a stereotaxic coordinates for BDA injections (from the Brain Atlas of Paxinos and Watson (1998); injections of 70 nl BDA (10%) were made at 3 specified depths at each site.

FIG. 17A shows the extent of smallest (dark gray), average (medium gray), and largest (light gray) lesions in animals treated with NEP1-40 alone (left) or NEP1-40 plus inosine-(right) 4 weeks after induction of focal ischemia. FIG. 17B shows quantitation of lesion volume shows that neither treatment alters stroke volume (saline data are repeated from FIG. 10B for comparison).

FIG. 18A and FIG. 18A' show low magnification camera lucida drawings of BDA-labeled CST fibers that cross from the in-tact side of the spinal cord into the side denervated by unilateral SMA injury in rats treated with NEP1-40 alone (FIG. 18A) or NEP1-40 plus inosine (FIG. 18A'). FIG. 18B and FIG. 18B' show high magnification photomicrographs of fibers in the grey matter of rats treated with NEP1-40-(b) or NEP1-40 plus inosine (FIG. 18B'). FIG. 18C and FIG. 18C' show camera lucida tracings of the fibers in FIG. 18B and FIG. 18B'. FIG. 18D and FIG. 18D' (insets) show higher magnification views of bouton-like structures in above axons. FIG. 18E and FIG. 18F show quantitation of recrossed CST fibers in the denervated dorsal funiculus and gray matter, respectively. FIG. 18G shows quantitation of re-crossed CST fibers ≥200 μm in length in the denervated gray matter. Results for saline are the same as shown in FIG. 11 and are shown here for reference. Results in FIG. 18E-FIG. 18G are reported as the number of labeled axons per mm of spinal cord. **/†† Differences between the combined-treatment group and groups treated with saline or NEP1-40 alone; *, **: Differences significant at $P<0.05$, $P<0.01$, respectively.

FIG. 19A shows NEP1-40 alone is effective in improving functional recovery using the impaired paw, and the combination of inosine plus NEP1-40 enables animals to perform at pre-operative levels by week 3. FIG. 19B shows performance with the unimpaired paw is unaffected by treatment. *$P<0.05$ compared to animals treated with saline; †$P<0.05$ compared to animals receiving NEP1-40.

FIG. 20B shows performance with the paw ipsilateral to the stroke is unaffected by treatment. *, , *: Differences between groups significant at P<0.05, P<0.01, P<0.001, respectively.

FIG. 21A: on a test for gross locomotor behavior (BBB: 21 point Basso-Beatty-Bresnahan scale), rats treated with saline alone could barely support their weight with the hindlimbs, whereas rats treated with inosine, either i.v. or i.c.v., returned to near-normal level of performance. FIG. 21B: On a test of skilled sensorimotor coordination (irregular ladder walk; performance scored as % steps made without slipping), animals treated with inosine, either i.v. or i.c.v., were far superior to saline-treated controls. (*, *Significantly different from saline-treated controls at P<0.01 or P<0.001, respectively).

DETAILED DESCRIPTION OF THE INVENTION

Figure 1A:
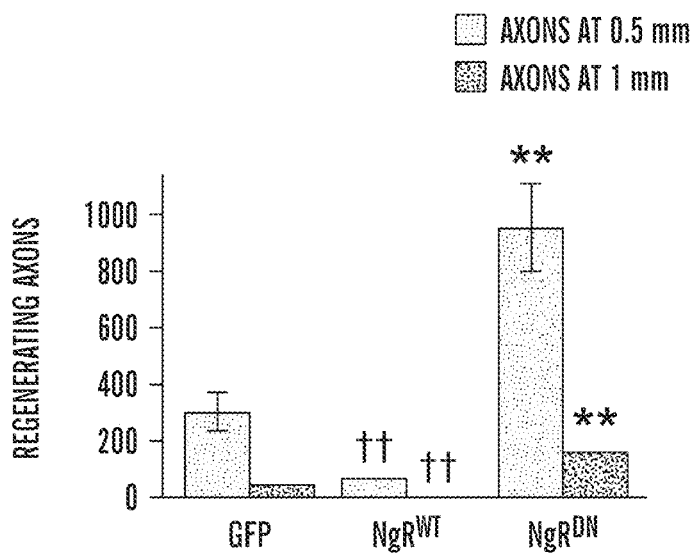
FIG. 1 shows quantization of axon regeneration and RGC survival. A: Quantization of axon growth at 0.5 mm (light bars) and 1 mm (dark bars) distal to the injury site. B: Cell survival (□III tubulin-positive RGCs per section). †† decrease relative to GFP-transfected controls significant at $p<0.01$; **increase relative to GFP-transfected controls significant at $p<0.01$.

The present invention provides methods of stimulating axonal growth of central nervous system (CNS) neurons that can be used for treating neurological disorders. The methods presented herein use a combination therapy that involves stimulation of axonal growth by both i) activating the growth pathway of CNS neurons and, ii) inhibiting the activity of NgR using an antagonist of NgR. Pharmaceutical compositions comprising these agents are also included. Preferred compositions are formulated for intravenous or intrathecal administration.

Definitions

The following definitions are provided for specific terms which are used in the following written description.

As used herein, the term "NgR antagonist" includes any agent that decreases, inhibits, blocks or interferes with NgR activity. The antagonist can be an agent that binds to NgR thereby inhibiting signal mediated by the receptor. Alternatively, the antagonist can be an agent that inhibits the expression of NgR, such as anti-sense RNA, or RNAi. The term antagonist, as used herein, also encompasses agents that inhibit the activity of a downstream signaling molecules that are activated by NgR, or the antagonist can be a dominant-negative form of NgR. Antagonists include, for example, antibodies, as defined herein, and molecules having antibody-like function such as synthetic analogues of antibodies, e.g., single-chain antigen binding molecules, small binding peptides, or mixtures thereof. Agents having antagonist activity can also include small organic molecules, natural products, peptides, aptamers, peptidomimetics, DNA and RNA.

Suitable NgR antagonists for use in methods of the invention include, but are not limited to, NEP1-40, a peptide antagonist which prevents NgR ligands from binding but which does not activate downstream signaling (Nature. 2002 May 30; 417(6888):547-51; J. Neurosci. 2003 May 15; 23(10):4219-27); monoclonal antibodies to the receptor (J Biol. Chem. 2004 Oct. 15; 279(42):43780-8) and those disclosed in WO 2004/014311, such as mAb's 7E11, 5B10, 1H2, 3G5, 2F7, 1D9.3, 2G7.1, 1E4.1, 1G4.1, 2C4.1, 2F11.1, 1H4.1, 2E8.1, 2G11.2, and 1B5.1; soluble fusion proteins, consisting of the ligand-binding domain of the NgR receptor linked to part of an immunoglobulin (NgR(310)ecto-Fc), that binds to NgR ligands and prevent them from interacting with the receptor on axons (J. Neurosci. 2004 Jul. 7; 24(27):6209-17; J. Neurosci. 2004 Nov. 17; 24(46):10511-20) and those disclosed in WO 2004/014311, such as sNogoR310 and sNogoR310-Fc and sNgR disclosed in MacDermid et al., 2004 European Journal of Neuroscience 20(10):p2567; soluble NgR, such as sNgR$^{c-term}$ and sNgR3$^{c-term}$ as disclosed in WO 2004/090103; a dominant-negative form of the Nogo Receptor (Neuron. 2002 Jul. 18; 35(2):283-90; and J. Neurosci. 2004 Feb. 18; 24(7):1646-51); clostridium botulinum C3 ADP-ribosyltransferase that inactivates RhoA; Y-27632, a small molecule inhibitor of ROCK (Dergham et al., 2002 J. Neurosci. 22: 6570-6577 and Lehmann et al. 1999 J. Neurosci. 19: 7537-7547); Nogo antagonist Pep2-41 and synthetic peptide 140 (PCT WO 03/031462; US 2002/0077295) and NEP1-40, a NgR antagonist 40 residue peptide that is commercially available from Phenix Pharmaceuticals Inc. (GrandPre et al., Nature 2002 417: 547-541), other NgR antagonist peptides are described in Fouiner et al., 2001 Nature 409: 341-346, Huber et al., 2000 Biol. Chem. 381: 407-419, Oertle, T et al., 2003 J. Neurosci. 23:5393-5406; and antibodies that block Nogo such as IN-1 antibody (Brosamle et al., J. Neurosci 2000 20: 8061-8068) and 7B12 (Wiessner et al., 2003 J. Cereb. Blood Flow Metab. 23: 154-165) as well as others, such as described in Schnell et al., Nature. 1990 Jan. 18; 343(6255):269-72; Kapfhammer et al., J Neurosci. 1992 June; 12(6):2112-9; Guest et al., J Neurosci Res. 1997 Dec. 1; 50(5):888-905; Z'Graggen et al., Neurosci. 1998 Jun. 15; 18(12):4744-57; Bareyre et al., J. Neurosci. 2002 Aug. 15; 22(16):7097-110; and Fouad et al., Eur J. Neurosci. 2004 November; 20(9):2479-82.

In one embodiment, the NgR antagonist comprises a peptide that binds to the NgR selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7.

In another embodiment, the NgR antagonist is a soluble NgR protein comprising the amino acid sequence of SEQ ID NO: 8 or SEQ ID NO: 9. In some embodiments, the soluble NgR is a fusion protein, e.g., an Fc-fusion protein. In some embodiments, the invention provides a soluble Nogo receptor-1 polypeptide consisting essentially of a N-terminal domain (NT), 8 leucine rich repeat domains (LRR) and a LRR C-terminal domain (LRRCT) of Nogo receptor 1. In some embodiments, said soluble Nogo receptor-1 polypeptide is joined to a signal sequence. In some embodiments, the LRR comprises a heterologous LRRR. In some embodiments, the invention provides a soluble Nogo receptor-1 polypeptide selected from the group consisting of: amino acid residues 26-344 of SEQ ID NO: 10; amino acid residues 26-310 of SEQ ID NO: 11; amino acid residues 26-344 of SEQ ID NO: 12; amino acid residues 27-344 of SEQ ID NO: 12; and amino acid residues 27-310 of SEQ ID NO: 13.

In one embodiment, the NgR antagonist peptide 140 (amino acid residues of 1055-1120 of human NogoA; see US 2002/0077295), which comprises SEQ ID NO: 14 that is acetylated at the C-terminus and amidated at the N-terminus.

In another embodiment, the NgR antagonist is Pep2-41 (amino acid residues 1055-1094 of human NogoA; see PCT Publication WO 03/031462), which comprises SEQ ID NO: 15 that is acetylated at the C-terminus and amidated at the N-terminus.

In another embodiment, the NgR antagonist is NEP1-40 (see GrandPre et al., Nature 2002 417: 547-541), which comprises SEQ ID NO: 16.

In some embodiments, the NgR antagonist is a nucleic acid aptamer that binds to a Nogo Receptor, or a portion thereof, and disrupts interaction of NOGO with the NOGO receptor. Preferred aptamers are disclosed in U.S. 2003/0203870.

As used herein, the term "antibody", includes human and animal mAbs, and preparations of polyclonal antibodies, as well as antibody fragments (antigen binding fragments), synthetic antibodies, including recombinant antibodies (antisera), chimeric antibodies, including humanized antibodies, anti-idiotopic antibodies and derivatives thereof.

In some embodiments, the antibody or antigen-antibody fragment binds to the NgR and inhibits Nogo receptor binding to a ligand (anti-NgR antibody). In one embodiment, a monoclonal antibody to the receptor is selected from the group consisting of 7E11, 5B10, 1H2, 3G5, 2F7, ID9.3, 2G7.1, 1E4.1, 1G4.1, 2C4.1, 2F11.1, 1H4.1, 2E8.1, 2G11.2, and 1B5.1 (See WO 2004/014311).

In some embodiments, the antibody or antigen-antibody fragment binds to a NgR ligand, such as OMgp, Nogo or MAG. Preferred anti-OMgP antibody or antigen-antibody fragment binds are disclosed in U.S. 2003/0113325. Preferred antibodies that block Nogo include IN-1 antibody (Brosamle et al., J. Neurosci 2000 20: 8061-8068) and 7B12 (Wiessner et al., 2003 J. Cereb. Blood Flow Metab. 23: 154-165).

U.S. Application No. 2003/0113325 also discloses peptides that bind OMgp, which are useful NgR antagonists in methods of the invention.

As used herein, the term "hexose" includes any hexose, or derivative thereof, that is able to activate the growth pathway of CNS neurons. Preferred hexoses include D-mannose and gulose. The term "hexose derivative" refers to a hexose molecule that has one or more residues (e.g. esters, ethers, amino groups, amido groups, phosphate groups, sulphate groups, carboxyl groups, carboxy-alkyl groups, and combinations thereof) covalently or ionically attached to one or more of the molecules hydroxyl groups. A preferred derivative includes glucose-6-phosphate. The term hexose derivative includes D- and L-isomers of hexose or hexose derivatives able to activate the growth pathway of CNS neurons. Hexose derivatives are well known in the art and commercially available (See also, for example, WO 2004/028468).

As used herein, an agent that "activates the growth pathway of CNS neurons" refers to an agent that elicits a response or result favorable to the health or function of a CNS neuron. Examples of such effects include improvements in the ability of a neuron or portion of the nervous system to resist insult, to regenerate, to maintain desirable function, to grow or to survive.

As used herein, the term "cAMP modulator" includes any compound which has the ability to modulate the amount, production, concentration, activity or stability of cAMP in a cell, or to modulate the pharmacological activity of cellular cAMP. cAMP modulators may act at the level of adenylate cyclase, upstream of adenylate cyclase, or downstream of adenylate cyclase, such as at the level of cAMP itself, in the signaling pathway that leads to the production of cAMP. Cyclic AMP modulators may act inside the cell, for example at the level of a G-protein such as Gi, Go, Gq, Gs and Gt, or outside the cell, such as at the level of an extra-cellular receptor such as a G-protein coupled receptor. Cyclic AMP modulators include activators of adenylate cyclase such as forskolin; nonhydrolyzable analogues of cAMP including 8-bromo-cAMP, 8-chloro-cAMP, or dibutyryl cAMP (db-cAMP); isoprotenol; vasoactive intestinal peptide; calcium ionophores; membrane depolarization; macrophage-derived factors that stimulate cAMP; agents that stimulate macrophage activation such as zymosan or IFN-y; phosphodiesterase inhibitors such as pentoxifylline and theophylline; specific phosphodiesterase IV (PDE IV) inhibitors; and beta 2-adrenoreceptor agonists such as salbutamol. The term cAMP modulator also includes compounds which inhibit cAMP production, function, activity or stability, such as phosphodiesterases, such as cyclic nucleotide phosphodiesterase 3B. cAMP modulators which inhibit cAMP production, function, activity or stability are known in the art and are described in, for example, in Nano et al., Pflugers Arch 439 (5): 547-54, 2000, the contents of which are incorporated herein by reference.

Examples of phosphodiesterase IV inhibitors suitable for use in the present invention include, but are not limited to, 4-arylpyrrolidinones, such as rolipram (A.G. Scientific, Inc.), nitraquazone, denbufylline, tibenelast, CP-80633 and quinazolinediones such as CP-77059.

Examples of Beta-2 adrenoreceptor agonist suitable for use in the present invention include, but are not limited to, salmeterol, fenoterol and isoproterenol.

As used herein, the term "administering" to a patient includes dispensing, delivering or applying an active compound in a pharmaceutical formulation to a subject by any suitable route for delivery of the active compound to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes.

As used herein, the term "contacting CNS neurons" refers to any mode of agent delivery or "administration" either to cells, or to whole organisms in which the agent is capable of exhibiting it's pharmacological effect in neurons. "contacting CNS neurons" is intended to include both in vivo and in vitro methods of bringing an agent of the invention into proximity with a neuron. Suitable modes of administration can be determined by those skilled in the art and such modes of administration may vary between agents. For example, when axonal growth of CNS neurons is stimulated ex vivo, agents can be administered, for example, by transfection, lipofection, electroporation, viral vector infection, or by addition to growth medium. An in vivo means of contacting neurons with an agent that activates the growth pathway of neurons includes, but is not limited to, for example lens injury. Lens injury leads to macrophage activation and factors secreted from macrophages stimulate RGCs to regenerate their axons (Yin et al, 2003).

As used herein, "effective amount" of an agent is an amount sufficient to achieve a desired therapeutic or pharmacological effect, such as an amount sufficient to inhibit the activity of NgR, or an amount that is capable of activating the growth pathway of CNS neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

A therapeutically effective amount or dosage of an agent may range from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an active compound can include a single treatment or a series of treatments. In one example, a subject is treated with an agent in the range of between about 0.1 to 20 mg/kg body weight, one time per week for between about 1 to 10 weeks, alternatively between 2 to 8 weeks, between about 3 to 7 weeks, or for about 4, 5, or 6 weeks. It will also be appreciated that the effective dosage of an agent used for treatment may increase or decrease over the course of a particular treatment. The agents of the present invention can be administered simultaneously or separately.

As used herein, the term "patient" or "subject" or "animal" or "host" refers to any mammal. The patient is preferably a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

As used herein, the term "Neurological disorder" is intended to include a disease, disorder, or condition which directly or indirectly affects the normal functioning or anatomy of a subject's nervous system.

As used herein, the term axonal "growth" or "outgrowth" includes the process by which axons or dendrites extend from a neuron. The outgrowth can result in a new neuritic projection or in the extension of a previously existing cellular process. Axonal outgrowth may include linear extension of an axonal process by 5 cell diameters or more. Neuronal growth processes, including neuritogenesis, can be evidenced by GAP-43 expression detected by methods such as immunostaining. "Stimulating axonal growth" means promoting axonal outgrowth.

As used herein, the term "CNS neurons" is intended to include the neurons of the brain, the cranial nerves and the spinal cord.

As used herein, "NgR" refers to a receptor that binds to Nogo, or to isoforms of Nogo. For example, Nogo-66 (Fournier et al., 2001, Nature, 409(6818):341-346). Non-limiting examples of Nogo receptors are found in Genebank at accession numbers NM_181377.2, AY311478.1, NM_181380.2, AF462390.1, NM_178570.1, NM_178568.1, AF283463.1, and AF532858. Several Nogo Receptor homologues are also described in U.S. patent applications 20030124704, and 0020077295, which are herein incorporated by reference in their entirety. The term "NgR" is also intended to encompass homologues and allelic variants thereof.

Various aspects of the invention are described in further detail in the following subsections:

NgR Antagonists

The combination therapy described herein comprises contacting CNS neurons with a NgR antagonist. The NgR antagonist can be administered before, concurrently with, or after administration of the agent that activates the growth pathway of CNS neurons. When the antagonist of NgR and additional therapeutic agent are administered at different times, they are preferably administered within a suitable time period to provide substantial overlap of the pharmacological activity of the agents. The skilled artisan will be able to determine the appropriate timing for co-administration of an antagonist and the additional agent depending on the particular agents selected and other factors.

The NgR antagonist can be DNA, RNA, a small organic molecule, a natural product, protein (e.g., antibody), peptide or peptidomimetic. Antagonists can be identified, for example, by screening libraries or collections of molecules, such as, the Chemical Repository of the National Cancer Institute, as described herein or using other suitable methods. Suitable screening methods that can be used to identify NgR antagonists for use in the present invention, as well as known NgR antagonists are described in U.S. Patent Application No.'s 20030203870, 20030186267, 20030113891, 20030113326, 20030113325, 20030060611, 20020077295, 20020012965, 2003/0113325, and PCT publication WO 2004/014311, which are herein incorporated by reference in their entirety. In particular, U.S. Application No's 20030186267, 20030113891, and 20030060611 describe ribozymes that cleave NgR mRNA and anti-sense molecules.

Another source of antagonists is combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods, such as the methods described herein.

The term "peptide", as used herein, refers to a compound consisting of from about two to about ninety amino acid residues wherein the amino group of one amino acid is linked to the carboxyl group of another amino acid by a peptide bond.

A peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). A "peptide" can comprise any suitable L- and/or D-amino acid, for example, common a-amino acids (e.g., alanine, glycine, valine), non-a-amino acids (e.g., P-alanine, 4-aminobutyric acid, 6 aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art and are disclosed in, for example, Green and Wuts, "Protecting Groups in Organic Synthesis", John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using well-known methods of combinatorial chemistry, and can be screened as described herein or using other suitable methods to determine if the library comprises peptides which can antagonize NgR function. Such peptide antagonists can then be isolated by suitable means.

The term "peptidomimetic", as used herein, refers to molecules which are not polypeptides, but which mimic aspects of their structures. For example, polysaccharides can be prepared that have the same functional groups as peptides which can antagonize NgR. Peptidomimetics can be designed, for example, by establishing the three dimensional structure of a peptide agent in the environment in which it is bound or will bind to NgR. The peptidomimetic comprises at least two components, the binding moiety or moieties and the backbone or supporting structure.

The binding moieties are the chemical atoms or groups which will react or form a complex (e.g., through hydrophobic or ionic interactions) with NgR, for example, with the amino acid (s) at or near the ligand binding site. For example, the binding moieties in a peptidomimetic can be the same as those in a peptide antagonist of NgR. The binding moieties can be an atom or chemical group which reacts with the receptor in the same or similar manner as the binding moiety in a peptide antagonist of NgR. Examples of binding moieties suitable for use in designing a peptidomimetic for a basic amino acid in a peptide are nitrogen containing groups, such as amines, ammoniums, guanidines and amides or phosphoniums. Examples of binding moieties suitable for use in designing a peptidomimetic for an acidic amino acid can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, thereby forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more —CONH-groups for a —NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding a-amino group on amino acids, thereby preparing a hydroxyacid and sequentially esterifying the hydroxyacids, optionally blocking the basic and acidic side chains to minimize side reactions. An appropriate chemical synthesis route can generally be readily identified upon determining the desired chemical structure of the peptidomimetic.

Peptidomimetics can be synthesized and assembled into libraries comprising a few to many discrete molecular species. Such libraries can be prepared using well known methods of combinatorial chemistry, and can be screened as described herein to determine if the library comprises one or more peptidomimetics which antagonize NgR function. Such peptidomimetic antagonists can then be isolated by suitable methods.

As used herein, an "antibody that inhibits NgR activity" or "anti-NgR antibody" includes an antibody or antigen-binding fragment. The term "antibody" as used herein encompasses polyclonal or monoclonal antibodies as well as functional fragments of antibodies, including fragments of chimeric, human, humanized, primatized, veneered or single-chain antibodies. Functional fragments include antigen-binding fragments which bind to NgR. For example, antibody fragments capable of binding to NgR or portions thereof, including, but not limited to Fv, Fab, Fab' and F (ab') 2 fragments can be used. Such fragments can be produced by enzymatic cleavage or by recombinant techniques. For example, papain or pepsin cleavage can generate Fab or F (ab') 2 fragments, respectively. Other proteases with the requisite substrate specificity can also be used to generate Fab or F (ab') 2 fragments. Antibodies can also be produced in a variety of truncated forms using antibody genes in which one or more stop codons have been introduced upstream of the natural stop site. For example, a chimeric gene encoding a F (ab') 2 heavy chain portion can be designed to include DNA sequences encoding the CH, domain and hinge region of the heavy chain.

Single-chain antibodies, and chimeric, human, humanized or primatized (CDR-grafted), or veneered antibodies, as well as chimeric, CDR-grafted or veneered single-chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19 (9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for mammalian (e.g., human) NgR can be raised against an appropriate immunogen, such as isolated and/or recombinant human NgR or portions thereof (including synthetic molecules, such as synthetic peptides).

Preparation of immunizing antigen, and polyclonal and monoclonal antibody production can be performed using any suitable technique. For example, monoclonal antibodies directed against binding cell surface epitopes can be readily produced by one skilled in the art. The general methodology for making monoclonal antibodies by hybridomas is well known. Other suitable methods of producing or isolating antibodies of the requisite specificity can be used, including, for example, methods which select recombinant antibody from a library (e.g., a phage display library). Transgenic animals capable of producing a repertoire of human antibodies (e.g., XenoMouse™ (Abgenix, Fremont, Calif.)) can be produced using suitable methods (see, e.g., WO 98/24893 (Abgenix), published Jun. 11, 1998; Kucherlapati, R. and Jakobovits, A., U.S. Pat. No. 5,939,598; Jakobovits et al., Proc. Natl. Acad. Sci. USA, 90: 2551-2555 (1993); Jakobovits et al., Nature, 362: 255-258 (1993)). Additional methods for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

The NgR antagonist of the invention can also be an RNA interfering agent, such as siRNA The use of siRNAs and siRNA-based technologies (for example, shRNA-expression vectors) has proven to be a powerful tool for the silencing of gene expression in a sequence-specific manner and has been found to be amenable to a wide variety of mammalian cell types and tissues. Not only have siRNAs proven to be effective for the dissection of gene function, their application as a therapeutic modality is being aggressively investigated.

Delivery of RNA Interfering Agents

In one embodiment, the RNA interfering agents used in the methods of the invention, e.g., the siRNAs, are taken up actively by cells in vivo following intravenous injection, e.g., hydrodynamic injection, without the use of a vector.

Other strategies for delivery of the RNA interfering agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

In one embodiment, the dsRNA, such as siRNA or shRNA, is delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used.

In one embodiment, the RNA interfering agents, e.g., the siRNAs used in the methods of the invention, can be introduced into cells, e.g., cultured cells, which are subsequently transplanted into the subject by, e.g., transplanting or grafting, or alternatively, can be obtained from a donor (i.e., a source other than the ultimate recipient), and applied to a recipient by, e.g., transplanting or grafting, subsequent to administration of the RNA interfering agents, e.g., the siRNAs of the invention, to the cells. Alternatively, the RNA interfering agents, e.g., the siRNAs of the invention, can be introduced directly into the subject in such a manner that they are directed to and taken up by the target cells and regulate or promote RNA interference of NgR expression. The RNA interfering agents, e.g., the siRNAs of the invention, may be delivered singly, or in combination with other RNA interfering agents.

An "RNA interfering agent" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi).

Preferably, the RNA interfering agent in the methods of the present invention is siRNA.

The NgR targeting siRNAs are designed so as to maximize the uptake of the antisense (guide) strand of the siRNA into RNA-induced silencing complex (RISC) and thereby maximize the ability of RISC to target NGR mRNA for degradation. This can be accomplished by looking for sequences that has the lowest free energy of binding at the 5'-terminus of the antisense strand. The lower free energy would lead to an enhancement of the unwinding of the 5'-end of the antisense strand of the siRNA duplex, thereby ensuring that the antisense strand will be taken up by RISC and direct the sequence-specific cleavage of NgR mRNA.

RNA Interfering Agents

"RNA interference (RNAi)" is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent may be a cellular gene or genomic sequence. An siRNA may be substantially homologous to the target gene or genomic sequence, or a fragment thereof. As used herein, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target allele so as to prevent its interaction with the normal allele.

The siRNA preferably targets only one sequence. Each of the RNA interfering agents, such as siRNAs, can be screened for potential off-target effects may be analyzed using, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues may be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology.

Agents that Activate the Growth Pathway of CNS Neurons

Agents that activate the growth pathway of CNS neurons are agents that are capable of producing a neurosalutary effect. As used herein, a "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. For example, examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; or reversing age-related loss of cholinergic innervation.

Any agent that activates the growth pathway of CNS neurons is suitable for use in the methods of the present invention. Some preferred agents include but are not limited to inosine, mannose, gulose, or glucose-6-phosphate, as described in Li et. al., 2003, J. Neuroscience 23(21):7830-7838; Chen Et al., 2002, Proc. Natl. Acad. Sci. U.S.A, 99:1931-1936; and Benowitz et al., 1998 J. Biol. Chem. 273:29626-29634, which are herein incorporated by reference in their entirety. TGF-β, and oncomodulin as described in Yin et al., 2003, J. Neurosci., 23: 2284-2293, are also preferred agents. In addition, polypeptide growth factors such as BDNF, NGF, NT-3, CNTF, LIF, and GDNF can be used. In one embodiment the methods of the present invention further comprise contacting CNS neurons with a cAMP modulator that increases the concentration of intracellular cAMP. For example, the ability of mature rat retinal ganglionic cells to respond to mannose requires elevated cAMP (Li et. al., 2003, J. Neuroscience 23(21):7830-7838).

The ability of an agent to activate the growth pathway of CNS neurons in a subject may be assessed using any of a variety of known procedures and assays. For example, the ability of an agent to re-establish neural connectivity and/or function after an CNS injury, may be determined histologically (either by slicing neuronal tissue and looking at neuronal branching, or by showing cytoplasmic transport of dyes). Agents may also be assessed by monitoring the ability of the agent to fully or partially restore the electroretinogram after damage to the neural retina or optic nerve; or to fully or partially restore a pupillary response to light in the damaged eye.

Other tests that may be used to determine the ability of an agent to produce a neurosalutary effect in a subject include standard tests of neurological function in human subjects or in animal models of spinal injury (such as standard reflex testing, urologic tests, urodynamic testing, tests for deep and superficial pain appreciation, propnoceptive placing of the hind limbs, ambulation, and evoked potential testing). In addition, nerve impulse conduction can be measured in a subject, such as by measuring conduct action potentials, as an indication of the production of a neurosalutary effect.

Animal models suitable for use in the assays of the present invention include the rat model of partial transaction (described in Weidner et al., 2001). This animal model tests how well a compound can enhance the survival and sprouting of the intact remaining fragment of an almost fully-transected cord. Accordingly, after administration of a candidate agent these animals may be evaluated for recovery of a certain function, such as how well the rats may manipulate food pellets with their forearms (to which the relevant cord had been cut 97%).

Another animal model suitable for use in the assays of the present invention includes the rat model of stroke (described in Kawamata et al., 1997). This paper describes in detail various tests that may be used to assess sensor motor function in the limbs as well as vestibulomotor function after an injury. Administration to these animals of the compounds of the invention can be used to assess whether a given compound, route of administration, or dosage provides a neurosalutary effect, such as increasing the level of function, or increasing the rate of regaining function or the degree of retention of function in the test animals.

Standard neurological evaluations used to assess progress in human patients after a stroke may also be used to evaluate the ability of an agent to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

Pharmaceutically Acceptable Formulations

The agents of the present invention can be contained in pharmaceutically acceptable formulations. Such pharmaceutically acceptable formulation may include a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix. The terms "polymer" or "polymeric" are art-recognized and include a structural framework comprised of repeating monomer units which is capable of delivering a hexose derivative such that treatment of a targeted condition, such as a neurological disorder, occurs. The terms also include co-polymers and homopolymers such as synthetic or naturally occurring. Linear polymers, branched polymers, and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of the active compound release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection. Polymers can be prepared using methods known in the art.

The polymeric formulations can be formed by dispersion of the active compound within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and the active compound, the types of solvent used, and reaction times.

The active therapeutic compound can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 µm, preferably less than 20 µm, and more preferably between about 0.1 and 10 µm.

In another embodiment, the pharmaceutically acceptable formulations comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing an active compound such variables as the efficiency of active compound encapsulation, lability of the active compound, homogeneity and size of the resulting population of vesicles, active compound-to-lipid ratio, permeability, instability of the preparation, and pharmaceutical acceptability of the formulation should be considered.

Prior to introduction, the formulations can be sterilized, by any of the numerous available techniques of the art, such as with gamma radiation or electron beam sterilization.

Ophthalmic products for topical use may be packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v"). Such preparations may be packaged in dropper bottles or tubes suitable for safe administration to the eye, along with instructions for use.

Administration of the Pharmaceutically Acceptable Formulations to a Patient

When the agents are delivered to a patient, they can be administered by any suitable route, including, for example, orally (e.g., in capsules, suspensions or tablets) or by parenteral administration. Parenteral administration can include, for example, intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. Administration can be local or systemic as indicated. Agents can also be delivered using viral vectors, which are well known to those skilled in the art.

The compounds are administered such as the agents come into contact with a subject's nervous system. The preferred mode of administration can vary depending upon the particular agent chosen.

Both local and systemic administration are contemplated by the invention. Desirable features of local administration include achieving effective local concentrations of the active compound as well as avoiding adverse side effects from systemic administration of the active compound. In one embodiment, the active agents are administered by introduction into the cerebrospinal fluid of the subject. In certain aspects of the invention, the active compound is introduced into a cerebral ventricle, the lumbar area, or the cistema magna. In another aspect, the active compound is introduced locally, such as into the site of nerve or cord injury, into a site of pain or neural degeneration, or intraocularly to contact neuroretinal cells.

The pharmaceutically acceptable formulations can be suspended in aqueous vehicles and introduced through conventional hypodermic needles or using infusion pumps.

In one embodiment, the active compound formulation described herein is administered to the subject in the period from the time of, for example, an injury to the CNS up to about 100 hours after the injury has occurred, for example within 24, 12, or 6 hours from the time of injury.

In another embodiment of the invention, the active compound formulation is administered into a subject intrathecally. As used herein, the term "intrathecal administration" is intended to include delivering an active compound formulation directly into the cerebrospinal fluid of a subject, by techniques including lateral cerebroventricular injection through a burrhole or cisternal or lumbar puncture or the like (described in Lazorthes et al., 1991, and Ommaya A. K., 1984, the contents of which are incorporated herein by reference). The term "lumbar region" is intended to include the area between the third and fourth lumbar (lower back) vertebrae. The term "cistema magna" is intended to include the area where the skull ends and the spinal cord begins at the back of the head. The ten-n "cerebral ventricle" is intended to include the cavities in the brain that are continuous with the central canal of the spinal cord. Administration of an active compound to any of the above mentioned sites can be achieved by direct injection of the active compound formulation or by the use of infusion pumps. Implantable or external pumps and catheter may be used.

For injection, the active compound formulation of the invention can be formulated in liquid solutions, preferably in physiologically compatible buffers such as Hank's solution or Ringer's solution. In addition, the active compound formulation may be formulated in solid form and re-dissolved or suspended immediately prior to use. Lyophilized forms are also included. The injection can be, for example, in the form of a bolus injection or continuous infusion (such as using infusion pumps) of the active compound formulation.

In one embodiment of the invention, the active compound formulation is administered by lateral cerebroventricular injection into the brain of a subject, preferably within 100 hours of when an injury (resulting in a condition characterized by aberrant axonal outgrowth of central nervous system neurons) occurs (such as within 6, 12, or 24 hours of the time of the injury). The injection can be made, for example, through a burr hole made in the subject's skull. In another embodiment, the formulation is administered through a surgically inserted shunt into the cerebral ventricle of a subject, preferably within 100 hours of when an injury occurs (such as within 6, 12 or 24 hours of the time of the injury). For example, the injection can be made into the lateral ventricles, which are larger, even though injection into the third and fourth smaller ventricles can also be made. In yet another embodiment, the active compound formulation is administered by injection into the cistema magna, or lumbar area of a subject, preferably within 100 hours of when an injury occurs (such as within 6, 12, or 24 hours of the time of the injury).

An additional means of administration to intracranial tissue involves application of compounds of the invention to the olfactory epithelium, with subsequent transmission to the olfactory bulb and transport to more proximal portions of the brain. Such administration can be by nebulized or aerosolized preparations.

In another embodiment of the invention, the active compound formulation is administered to a subject at the site of injury, preferably within 100 hours of when an injury occurs (such as within 6, 12, or 24 hours of the time of the injury).

In a further embodiment, ophthalmic compositions of the present invention are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic compositions may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

Duration and Levels of Administration

In a preferred embodiment of the method of the invention, the active compound is administered to a subject for an extended period of time to produce optimum axonal outgrowth. Sustained contact with the active compound can be achieved by, for example, repeated administration of the active compound over a period of time, such as one week, several weeks, one month or longer. More preferably, the pharmaceutically acceptable formulation used to administer the active compound provides sustained delivery, such as "slow release" of the active compound to a subject. For example, the formulation may deliver the active compound for at least one, two, three, or four weeks after the pharmaceutically acceptable formulation is administered to the subject. Preferably, a subject to be treated in accordance with the present invention is treated with the active compound for at least 30 days (either by repeated administration or by use of a sustained delivery system, or both).

As used herein, the term "sustained delivery" is intended to include continual delivery of the active compound in vivo over a period of time following administration, preferably at least several days, a week, several weeks, one month or longer. Sustained delivery of the active compound can be demonstrated by, for example, the continued therapeutic effect of the active compound over time (such as sustained delivery of the agents can be demonstrated by continued axonal growth in CNS neurons in a subject). Alternatively, sustained delivery of the active compound may be demonstrated by detecting the presence of the active compounds in vivo over time.

Preferred approaches for sustained delivery include use of a polymeric capsule, a minipump to deliver the formulation, a biodegradable implant, or implanted transgenic autologous cells (as described in U.S. Pat. No. 6,214,622). Implantable infusion pump systems (such as Infusaid; see such as Zierski, J. et al, 1988; Kanoff, R. B., 1994) and osmotic pumps (sold by Alza Corporation) are available in the art. Another mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

It is to be noted that dosage values may vary with the severity of the condition to be alleviated. It is to be further understood that for any particular subject, specific dosage regimens should be adjusted over time according to the individual need and the professional judgment of the person administering or supervising the administration of the active compound and that dosage ranges set forth herein are exemplary only and are not intended to limit the scope or practice of the claimed invention.

The amount of agent administered to the individual will depend on the characteristics of the individual, such as general health, age, sex, body weight and tolerance to drugs as well as the degree, severity and type of rejection. The skilled artisan will be able to determine appropriate dosages depending on these and other factors. Typically, an effective amount can range from about 0.1 mg per day to about 100 mg per day for an adult. Preferably, the dosage ranges from about 1 mg per day to about 100 mg per day.

Antibodies and antigen-binding fragments thereof, particularly human, humanized and chimeric antibodies and antigen-binding fragments can often be administered less frequently than other types of therapeutics. For example, an effective amount of such an antibody can range from about 0.01 mg/kg to about 5 or 10 mg/kg administered daily, weekly, biweekly, monthly or less frequently.

In Vitro Treatment of Neurons

Neurons derived from the central or peripheral nervous system can be contacted with the agents ex vivo to modulate axonal outgrowth in vitro. Accordingly, neurons can be isolated from a subject and grown in vitro, using techniques well known in the art, and then treated in accordance with the present invention to modulate axonal outgrowth. Briefly, a neuronal culture can be obtained by allowing neurons to migrate out of fragments of neural tissue adhering to a suitable substrate (such as a culture dish) or by disaggregating the tissue, such as mechanically or enzymatically, to produce a suspension of neurons. For example, the enzymes trypsin, collagenase, elastase, hyaluronidase, DNase, pronase, dispase, or various combinations thereof can be used. Methods for isolating neuronal tissue and the disaggregation of tissue to obtain isolated cells are described in Freshney, Culture of Animal Cells, A Manual of Basic Technique, Third Ed., 1994, the contents of which are incorporated herein by reference.

Such cells can be subsequently contacted with the agents (alone or in combination with a cAMP modulator) in amounts and for a duration of time as described above. Once modulation of axonal outgrowth has been achieved in the neurons, these cells can be re-administered to the subject, such as by implantation.

Treatment of Neurological Disorders

Elements of the nervous system subject to disorders which may be effectively treated with the compounds and methods of the invention include the central, somatic, autonomic, sympathetic and parasympathetic components of the nervous system, neurosensory tissues within the eye, ear, nose, mouth or other organs, as well as glial tissues associated with neuronal cells and structures. Neurological disorders may be caused by an injury to a neuron, such as a mechanical injury or an injury due to a toxic compound, by the abnormal growth or development of a neuron, or by the misregulation, such as downregulation, of an activity of a neuron. Neurological disorders can detrimentally affect nervous system functions such as the sensory function (the ability to sense changes within the body and the outside environment); the integrative function (the ability to interpret the changes); and the motor function (the ability to respond to the interpretation by initiating an action such as a muscular contraction or glandular secretion).

Examples of neurological disorders include traumatic or toxic injuries to peripheral or cranial nerves, spinal cord or to the brain, cranial nerves, traumatic brain injury, stroke, cerebral aneurism, and spinal cord injury. Other neurological disorders include cognitive and neurodegenerative disorders such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, hereditary motor and sensory neuropathy (Charcot-Marie-Tooth disease), diabetic neuropathy, progressive supranuclear palsy, epilepsy, and Jakob-Creutzfieldt disease. Autonomic function disorders include hypertension and sleep disorders.

Also to be treated with compounds and methods of the invention are neuropsychiatric disorders such as depression, schizophrenia, schizoaffective disorder, Korsakoff's psychosis, mania, anxiety disorders, or phobic disorders, learning or memory disorders (such as amnesia and age-related memory loss), attention deficit disorder, dysthymic disorder, major depressive disorder, mania, obsessive-compulsive disorder, psychoactive substance use disorders, anxiety, phobias, panic disorder, bipolar affective disorder, psychogenic pain syndromes, and eating disorders. Other examples of neurological disorders include injuries to the nervous system due to an infectious disease (such as meningitis, high fevers of various etiologies, HIV, syphilis, or post-polio syndrome) and injuries to the nervous system due to electricity (including contact with electricity or lightning, and complications from electroconvulsive psychiatric therapy). The developing brain is a target for neurotoxicity in the developing central nervous system through many stages of pregnancy as well as during infancy and early childhood, and the methods of the invention may be utilized in preventing or treating neurological deficits in embryos or fetuses in utero, in premature infants, or in children with need of such treatment, including those with neurological birth defects. Further neurological disorders include, for example, those listed in Harrison's Principles of Internal Medicine (Braunwald et al., McGraw-Hill, 2001) and in the American Psychiatric Association's Diagnostic and Statistical Manual of Mental Disorders DSM-IV (American Psychiatric Press, 2000) both incorporated herein by reference in their entirety. Neurological disorders associated with ophthalmic conditions include retina and optic nerve damage, glaucoma and age related macular degeneration.

As used herein, the term "stroke" is art recognized and is intended to include sudden diminution or loss of consciousness, sensation, and voluntary motion caused by rupture or obstruction (for example, by a blood clot) of an artery of the brain.

As used herein, "Traumatic brain injury" is art recognized and is intended to include the condition in which, a traumatic blow to the head causes damage to the brain or connecting spinal cord, often without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

It is understood that the foregoing detailed description and the following examples are illustrative only and are not to be taken as limitations upon the scope of the invention. The terminology used herein is for the purpose of describing particular embodiments only, and is not intended to limit the scope of the present invention, which is defined solely by the claims. Various changes and modifications to the disclosed embodiments, which will be apparent to those skilled in the art, may be made without departing from the spirit and scope of the present invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used to describe the present invention, in connection with percentages means ±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example I

NgR Mediates Axon Regeneration in Mature CNS

The optic nerve is a classic model for understanding regenerative failure or success in the mature mammalian CNS (Aguayo et al., 1991; Ramon y Cajal, 1991). Axons that are injured in the mature rat optic nerve cannot grow back into the myelin-rich environment distal to the injury site. In addition, if axonal damage occurs close to the eye, retinal ganglion cells (RGCs) undergo apoptosis after several days (Berkelaar et al., 1994). Several intraocular manipulations, including injuring the lens (Leon et al., 2000; Fischer et al., 2000, 2001), injecting the pro-inflammatory agent zymosan (Yin et al., 2003), or inserting a peripheral nerve fragment (Berry et al., 1996), partially reverse this situation and allow many RGCs to survive injury and regenerate lengthy axons into the optic nerve; these effects appear to be mediated via macrophage-derived factors (Yin et al., 2003) acting in concert with a carbohydrate that is constitutively present in the eye (Li et al., 2003). The partial regeneration that occurs under these conditions provides a sensitized background on which to investigate the significance of NgR in CNS regeneration. This was done here by transfecting RGCs with adeno-associated viruses (AAV) carrying a gene for either the wild-type NgR or for NgR$^{DN}$.

Materials and Methods

Viral Transfections.

cDNAs encoding either wild-type NgR (Fournier et al., 2001) or a C-terminal truncated, dominant-negative variant of NgR that retains the ligand binding domain does not associate with its co-receptor (Domeniconi et al., 2002; Wang et al., 2002b), were inserted into the AAV-MCS2-IGFP plasmid, described on the website of the Harvard Gene Therapy Initiative ( ). Gene expression was driven by a CMV promoter. Constructs expressed enhanced green fluorescent protein (GFP) from an internal ribosome entry site. NgR constructs obtained an HA epitope tag, as described (Wang et al., 2002a). Controls were transfected with viruses expressing GFP alone. Virus production was carried out at the Harvard Gene Therapy Initiative Core Facility. To transfect RGCs, female Sprague-Dawley rats (160-180 g) were anesthetized with Ketamine-Xylazine and the back of the eye was exposed intraorbitally. After withdrawing 10 µl of fluid from the eye, ~$10^{10}$ AAV particles in 10 µl phosphate-buffered saline (PBS) were injected into the vitreous body using a micropipette, with care taken to avoid injuring the lens (Fischer et al., 2000). Injections were done 3 weeks prior to optic nerve surgery to maximize levels of transgene expression at the onset of axon regeneration (Cheng et al., 2002).

Optic Nerve Surgery and Lens Injury.

Animals were re-anesthetized using Ketamine-Xylazine, immobilized in a stereotaxic apparatus, and the left optic nerve was surgically exposed intraorbitally. After opening the meninges longitudinally, the optic nerve was crushed 2 mm from the orbit by applying pressure with jewelers' forceps under a dissecting microscope for 10 sec. Lens injury was accomplished by puncturing the lens capsule with a microcapillary through a posterior approach (Fischer et al., 2000). Lens injury leads to macrophage activation, and factors secreted from activated macrophages stimulate RGCs to regenerate their axons (Yin et al., 2003). Controls sustained nerve injury but no lens damage. Nerve injury was verified by the appearance of a clearing at the crush site; the vascular integrity of the retina was verified by fundoscopic examination.

Retinal Explants.

Explants of viral-transfected retinas were prepared 4 days after crushing the optic nerve and either injuring the lens or performing sham surgery. Animals were euthanized and their retinas were dissected out, cut into 8 radial pieces, and cultured in DMEM-B27 (Invitrogen) on a laminin-poly-D-lysine substrate (Bahr et al., 1988) with or without myelin, prepared as described (Wang et al., 2002b). Two days later, the number of axons growing ≥50 μm beyond the margin of each explant was counted with the aid of an inverted phase-contrast microscope (Axiovert, Zeiss) and a calibrated ocular micrometer at a magnification of ×200. In cases with strong regeneration, some fiber fasciculation was observed, and these were counted as single axons. Results from individual explants were averaged within each treatment group and between-group differences were evaluated with Student's t-test. To evaluate growth on myelin, we calculated the ratio of axons growing >500 μm to total axons ≥50 μm in TUJ1-immunostained explants. This was done to account for the variability in adhesion and outgrowth of explants grown on the mixed myelin-laminin substrate, and to visualize axons against a particulate background. Results were averaged from 6 explants per retina and 4-5 retinas per condition.

Histology: Retinal Explants.

After 2 days in culture, retinas were fixed in 4% paraformaldehyde in PBS, treated with methanol for 10 min, blocking solution containing 10% serum from the same species as the secondary antibody for 1 hour (RT), and then incubated overnight (4° C.) with antibodies against either GFP (prepared in rabbit: Molecular Probes, Eugene, Oreg., 1:1000); βIII tubulin (mouse monoclonal antibody TUJ1, Babco, Richmond, Calif., 1:500), or the HA epitope tag (mouse monoclonal antibody, Molecular Probes, 1:100) fused to NgR. Primary antibodies were prepared in Tris-buffered saline (TBS) containing 2× physiological saline, 5% serum, 2% BSA, and 0.1% Tween-20. Following 3 rinses in TBS, sections were incubated with fluorescently tagged secondary antibodies, i.e., AlexaFluor 488-conjugated goat antibody to rabbit IgG or AlexaFluor 594-conjugated goat antibody to mouse IgG (1:500, 2 hours, RT), rinsed, and covered.

Optic Nerve and Retinal Cross-Sections.

Two weeks after nerve surgery, animals were euthanized with an overdose of anesthesia and perfused with PBS followed by 4% paraformaldehyde in PBS. Optic nerves with retinas attached were dissected and prepared for longitudinal sectioning as described (Yin et al., 2003). Sections were stained to visualize either GAP-43 (primary antibody prepared in sheep (Benowitz et al., 1988); 1:1000, followed by a fluorescent-tagged donkey anti-sheep IgG), or GFP, as above. Retinal cross-sections were stained to visualize either GFP or βIII tubulin (as above), or NgR. The latter was visualized using a primary antibody made in goat to the N-terminus of NgR (1:10, Santa Cruz), followed by a fluorescent secondary antibody to goat IgG made in donkey (1:500).

Axon Regeneration: Quantitation.

Regeneration was quantified as described (Leon et al., 2000; Yin et al, 2003). In brief, under 400× magnification, we counted the number of GAP-43 positive axons extending >500 μm and >1 mm from the injury site in 4 sections per case, normalized these numbers to the cross-sectional width of the optic nerve, and used these data to calculate the total numbers of regenerating axons in each animal (Leon et al., 2000; Yin et al, 2003). The significance of inter-group differences were evaluated by Student's t-tests.

Cell Survival.

Cross-sections through the center of the retina were double-stained with antibodies to GFP and βIII tubulin as described above. The numbers of βIII tubulin-positive cells per section were counted in 4-6 sections per case, averaged for each case, and then averaged across all similarly treated animals to obtain group means and standard errors.

Results

To investigate the role of NgR in vivo, we injected mature rats intravitreally with AAV (serotype 2) carrying a plasmid expressing either the wild-type Nogo receptor ($NgR^{WT}$) (Fournier et al., 2001) or a truncated, dominant-negative variant of NgR ($NgR^{DN}$) (Domeniconi et al., 2002; Wang et al., 2002b) from a CMV promoter, along with enhanced green fluorescent protein (GFP) from an internal ribosome entry site ($AAV\text{-}NgR^{WT}\text{-}IGFP$ and $AAV\text{-}NgR^{DN}\text{-}IGFP$, respectively). Controls were transfected with viruses expressing GFP alone (AAV-GFP). When examined 3 weeks later, the GFP reporter was detected in >75% of all RGCs, in agreement with prior studies using a similar virus (Cheng et al., 2002; Martin et al., 2002). GFP-labeled cells were localized almost exclusively within the ganglion cell layer in cells that are immunopositive for βIII tubulin. Within the retina, this tubulin isoform is expressed only in RGCs (Cui et al., 2003: Yin et al., 2003), which we verified by showing a complete overlap of βIII tubulin immunostaining with Fluorogold labeling in RGCs after injecting the latter into the superior colliculus. The specificity of transfection to RGCs presumably reflects a combination of the neural-selectivity of AAV2 (Bartlett et al., 1998) and the ready access of intravitreal viral particles of RGC axons and somata.

NgR immunostaining was modest or weak in controls transfected with AAV-GFP, but was strong in retinas transfected with $AAV\text{-}NgR^{WT}\text{-}IGFP$. Thus, in transfected cells, levels of transgene expression exceed those of the endogenous protein. Three weeks after transfections, animals were re-anesthetized and the left optic nerve was crushed 2 mm from the back of the eye; in half of these animals, the lens was damaged to activate macrophages and promote regeneration (Fischer et al., 2000; Leon et al., 2000; Yin et al., 2003); the remaining animals received no further surgery.

Regeneration was investigated 2 weeks after optic nerve injury; prior work has shown that damaged axons have begun to grow back into the distal optic nerve by this time provided macrophages have been activated intravitreally (Leon et al., 2000). Regenerating axons are readily distinguished by staining with antibodies to GAP-43. GAP-43 is normally undetectable in the mature optic nerve but is strongly upregulated in RGC axons undergoing regeneration (Schaden et al., 1994;

Berry et al., 1996; Leon et al., 2000). The origin of the GAP-43 positive axons in RGCs has been shown previously by anterograde labeling and double-immunostaining (Leon et al., 2000). Controls transfected with AAV-GFP (n=8) showed a moderate number of GAP-43-positive axons distal to the injury site, in numbers comparable to those reported in similarly treated animals without viral transfections (FIG. 1A; Leon et al., 2000).

Two weeks after nerve crush and lens injury, animals overexpressing $NgR^{WT}$ showed 76% fewer axons regenerating ≥0.5 mm from the injury site than controls (n=9, p<0.01), and 96% fewer axons extending ≥1 mm (p<0.01). Many $NgR^{WT}$-containing axons retracted from the lesion site towards the optic nerve head, reflecting the sensitivity of these axons to myelin; this phenomenon was never observed in animals expressing GFP alone or $NgR^{DN}$.

In striking contrast, expression of $NgR^{DN}$ enhanced axon regeneration greatly. Two weeks after nerve crush and lens injury, animals expressing $NgR^{DN}$ (n=5) extended approximately 3 times more axons >1 mm beyond the injury site than controls expressing GFP alone, and 75 times more axons than animals expressing $NR^{WT}$ (FIG. 1A). In general, although GFP could be visualized in many axons proximal to the injury site, fewer than half of the axons that extended beyond this point exhibited GFP immunofluorescence, presumably due to decreasing concentrations of the cytoplasmic reporter protein far from RGC somata. However, the longest regenerating axons frequently exhibited GFP staining, which suggests that they may have arisen from RGCs that express abundant $NgR^{DN}$. This co-localization further confirms the origin of GAP-43 immunopositive axons in RGCs. Diminished transgene expression combined with declining RGC viability after longer survival times probably limits the amount of regeneration that can be obtained under the present conditions, and further research will be required to determine whether overcoming these problems will enable growth-activated, $NgR^{DN}$-expressing RGCs to extend axons back to their central targets.

In the absence of lens injury, NgRDN expression did not enable RGCs to regenerate their axons into the distal optic nerve. Quantitatively, no axons were counted at 0.5 mm in any animal without lens injury irrespective of which transgene was expressed.

Figure 1B:
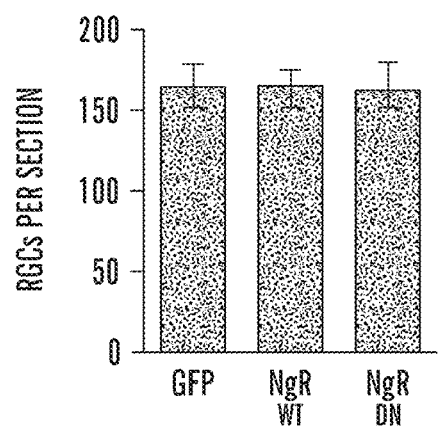

To investigate whether the effects of the 3 transgenes on axon regeneration might reflect differences in cell survival, we counted TUJ1-positive cells in retinal cross-sections 2 weeks after nerve crush and lens injury. Transgene expression had no measurable effect on cell survival (FIG. 1B).

Figure 2A:
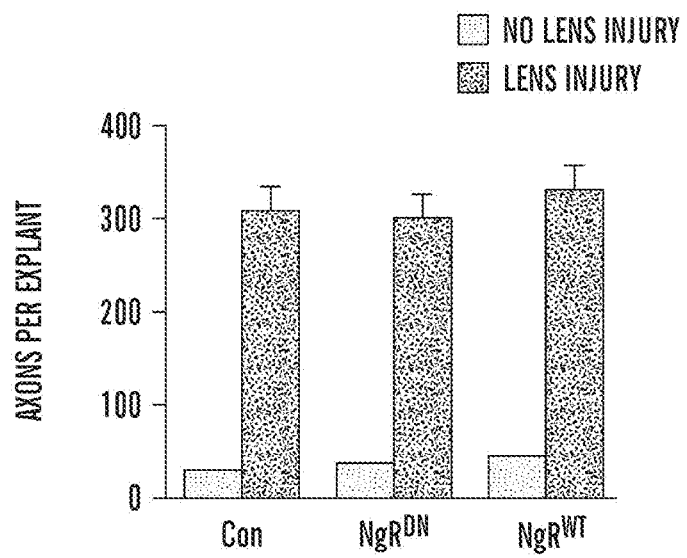
FIG. 2 shows axon regeneration on permissive and non-permissive substrates. A-B: Retinal explants grown on a permissive laminin/poly-L-lysine substrate. A: Quantization of axon growth. Control retina not exposed to macrophage-derived factors in vivo (i.e., no lens injury) and in retinas transfected with AAV-NgR$^{WT}$-IGFP and exposed to macrophage-derived factors in vivo or axons arising from growth-activated retina transfected with AAV-NgR$^{DN}$-IGFP B: Growth of transfected retinal explants (exposed to macrophage-derived factors in vivo) on myelin (percentage of axons arising from explants that extend >500 μm). ††† decrease relative to controls significant at $p<0.001$; **increase relative to controls significant at $p<0.001$. Scale bar: 100 μm.

To investigate whether altering NgR levels or function might affect RGCs' intrinsic ability to extend axons, we investigated outgrowth on a more permissive substrate. As before, we transfected RGCs in vivo with either AAV-$NgR^{WT}$-IGFP or AAV-$NgR^{DN}$-IGFP, then performed optic nerve surgery combined with lens injury or sham intraocular surgery 3 weeks later. After 4 days, a time at which axotomized RGCs stimulated by macrophage-derived factors go into a growth state (Fischer et al., 2000), we explanted wedges of retinas onto a poly-L-lysine-laminin (PLL) substrate. Little outgrowth was seen in explants not exposed to growth factors in vivo irrespective of transgene expression (FIG. 2A). It should be noted that axotomized RGCs do not show signs of apoptosis at this time point (Berkelaar et al., 1994). Retinas primed to grow as a result of lens injury in vivo showed strong outgrowth regardless of which transgene was expressed (FIG. 2A). There was strong outgrowth from RGCs expressing $NgR^{WT}$, while minimal outgrowth from a growth-activated retina expressing $NgR^{DN}$.

Figure 2B:
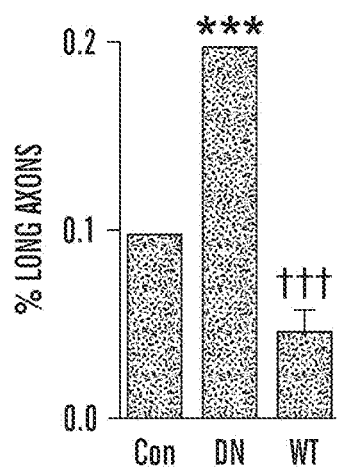

As expected, the effects of transgene expression became apparent when explants were plated on a substrate containing myelin (FIG. 2B). $NgR^{WT}$ overexpression decreased the percentage of axons growing >500 μm on a mixed myelin-laminin substrate by approximately 50% relative to controls, whereas expression of $NgR^{DN}$ doubled the percentage of long axons (p<0.001 in both cases).

Discussion

The results of this study show that NgR plays a major role in limiting axon regeneration in the mature optic nerve; however, extensive regeneration requires activation of neurons' intrinsic growth state in addition to suppression of NgR activity. Our results also demonstrate that AAV-mediated transfection provides a highly effective means of altering either the levels of functioning of gene products important for axon regeneration in CNS neurons.

The critical role of NgR for optic nerve regeneration is evident from the dramatic enhancement of axon growth that occurs when growth-sensitized RGCs express a dominant-negative form of NgR, and conversely, from the near-complete failure of sensitized RGCs to regenerate their axons when overexpressing wild-type NgR. In mature mice, a null mutation of the NgR gene does not enhance regeneration of the corticospinal tract (CST), but does increase sprouting of essential descending serotonergic projections after spinal cord injury (Kim et al., 2003a). Based upon the present study, we would propose that the contrasting results seen in CST vs. serotonergic axons after NgR deletion may reflect intrinsic differences in the growth state of cortical pyramidal cells vs. raphe neurons, and that activation of the former with appropriate trophic factors could lead to a stronger CST phenotype.

Alterations of NgR functioning (or levels) and activation of the axonal growth program are largely independent of one another. As shown in the explant studies, altering NgR functioning or levels did not affect neurons' ability to extend axons on a permissive substrate, and activating RGCs' intrinsic growth state still left axons partially responsive to the effects of myelin proteins. Activation of RGCs' growth program by macrophage-derived factors greatly increases the expression of GAP-43 (Yin et al., 2003) and other regeneration-associated genes, but does not appreciably alter mRNA levels of NgR or p75, a NgR co-receptor (D. Fischer and L. Benowitz, unpublished gene profiling results). Inhibition of RhoA, an essential downstream mediator of NgR functioning, allows for limited axon regeneration when an ADP ribosyl transferase is delivered at the site of optic nerve injury (Lehmann et al., 1999).

AAV-mediated transfection of growth-sensitized RGCs represents a general approach for investigating the role of various gene products in axon regeneration. By this method, one can readily obtain precise temporal and spatial control of gene expression without the expense, time delays, and possible developmental problems inherent in transgenic technology. The specificity and efficiency of RGC transfection by AAV found here has also been demonstrated in other studies (Cheng et al., 2002; Martin et al., 2002).

The clinical implications of this work are clear: extensive axon regeneration is not attainable in the mature CNS by overcoming inhibitory signals alone, but requires that neurons' intrinsic growth state be activated at the same time (Schnell et al., 1994; Cheng et al., 1996; Guest et al., 1997).

Example II

RhoA Inactivation Combined with Lens Injury Results in High Levels of Axon Regeneration Materials and Methods
Induction of Axon Regeneration Adult female Sprague Dawley rats, 220-250 gm, were anesthetized by intraperitoneal injection of ketamine (60-80 mg/kg) and xylazine (10-15 mg/kg), and a 1-1.5 cm incision was made in the skin above the right orbit. The optic nerve was surgically exposed under an operating microscope, the epineurium was opened longitudinally, and the nerve was crushed 0.5 mm behind the eye for 10 sec using jeweler's forceps, avoiding injury to the ophthalmic artery. Nerve injury was verified by the appearance of a clearing at the crush site; the vascular integrity of the retina was verified by fundoscopic examination. Lens injury was induced through a retrolenticular approach, puncturing the lens capsule with the narrow tip of a microcapillary tube; inflammation was enhanced by injecting 10 µl of PBS intravitreally after retrieving the same volume from the anterior chamber of the eye (Fischer et al., 2000). Controls received PBS injections only. All surgical procedures were approved by the Institutional Animal Care and Use Committee of Children's Hospital.

Retinal Explants

Rats were killed, and their retinas were dissected 0-7 d after crushing the optic nerve and either injuring the lens or performing sham intraocular surgery (n=5 animals per group). Additional controls received no treatment (n=5) or lens injury without nerve crush (n=5). Retinas were cut into eight radial pieces, which were cultured in astrocyte-microglia growth medium (PromoCeli, Heidelberg, Germany) in laminin-poly-L-lysine-coated dishes (Bahr et al, 1988). In some cases, we coated culture plates with myelin (courtesy of Dr. Zhigang He, Children's Hospital, Boston, Mass.), as described (Wang et al., 2002a). The number of axons extending ≥50 µm from each explant was counted after 24 and 48 hr using inverted phase-contrast optics (200×; Axiovert; Zeiss, Thornwood, N.Y.) and a calibrated ocular micrometer. In cases with strong regeneration, some fiber fasciculation was observed, and these were counted as one axon. Results from individual explants were averaged within each experimental group, and intergroup differences were evaluated by Student's 't test. Growth velocities were estimated after at least five axons had extended from the edge of the explant. The lengths of these five axons were measured at 4, 6, 12, 18, 24, 36, and 48 hr.

Immunohistochemistry

Animals were killed with a lethal overdose of anesthesia and perfused through the heart with cold saline plus heparin, followed by 4% paraformaldehyde. Eyes with optic nerves segments attached were dissected from connective tissue, postfixed overnight, transferred to 30% sucrose overnight (4° C.), and frozen. Frozen sections were cut longitudinally on a cryostat, thaw-mounted onto coated glass slides (Superfrost plus; Fisher Scientific, Pittsburgh, Pa.), and stored at −20° C. until additional use. To visualize RGCs in double-labeling experiments, we used the monoclonal mouse TUJ1 antibody (Babco, Richmond, Calif.) at a dilution of 1:500. Secondary antibodies included a cyanine 3-conjugated anti-rabbit IgG antibody (1:600; Jackson ImmunoResearch, West Grove, Pa.) and anti-mouse IgG conjugated to Alexa Flour 488 (1:500; Molecular Probes). Flourescent sections were covered using Vectashield mounting medium (Vector Laboratories) and analyzed under a fluorescent microscope.

Visualization of RhoA Activation by Rho-Binding Domain-Glutathione S-Transferase Staining The Rho-binding domain (RBD) of the protein rhotekin binds selectively to the active (GTP-bound) form of RhoA and can be used as a reagent to visualize RhoA-GTP in cell homogenates or in situ (Dubreuil et al., 2002). Bacteria expressing a glutathione S-transferase (GST)-RBD fusion protein in a pGEX vector (a gift from John Collard, Division of Cell Biology, Netherlands Cancer Institute, Amsterdam, The Netherlands) were grown in L-broth with 100 µl/ml ampicillin. Overnight cultures were diluted 1:10 into 1000 ml of L-broth and incubated in a shaking bacterial incubator at 37° C. for 1 hr. Isopropl-β-D-thiogalactopyranoside was then added to the incubating cultures for 2 hr, resulting in a final concentration of 0.1 mM. Bacteria were collected by centrifugation at 6000×g for 20 min. The pellets were resuspended in 10 ml of lysis buffer (50 mM Tris, pH 7.5, 1% Triton-X, 150 mM NaCl, 5 mM $MgCl_2$, 1 mM DTT, 10 µg/ml leueptin, 10 µg/ml aprotinin, and 1 mM PMSF), sonicated, and lysates were spun at 14,000 rpm for 30 min at 4° C. The clarified bacterial lysate was diluted 1:100 and used for in situ binding studies. Paraformaldehyde-fixed retinal cryostat sections were incubated with diluted lysate overnight at 4° C., washed three times in TBS, blocked in 5% BSA in TBS with 0.05% Tween 20 for 1 hr at room temperature, and incubated with an anti-GST antibody (Immunology Consultants Laboratory, Newberg, Oreg.) and with the TUJ1 antibody (Babco) overnight at 4° C. as described (Dubreuil et al., 2002). Sections were washed in TBS and incubated for 2 hr at room temperature with Alexa Fluor 488 and 594-conjugated secondary antibodies (1:500, Molecular Probes).

Viral Construction cDNA encoding a modified form of the ADP ribosyl transferase C3 was generated by PCR from the pET-3a-C3 plasmid, generously provided by Dr. S, Narumiya (Kyoto University, Kyoto, Japan) (Kumagai et al., 1993), using the following primers: forward, 5'-TATGGCTAGCTATGC ACATACTTTCACAGAATT-3' (SEQ ID NO: 17); reverse, 5'-CTATTTAAATATCATTGCTGTAATCATAATTTGTC-3' (SEQ ID NO: 18). The encoded form (Fournier et al., 2001) and the dipeptide Met-Ala is attached to $Ser^1$. The cDNA was inserted into the AAV-MCS2-IGFP plasmid, developed by the Harvard Gene Therapy Initiative (HGTI). In addition, we ligated in-frame sequence encoding the first 10 amino acids of GAP-43 to target the protein to the cell membrane (Zuber et al., 1989; Liu et al., 1994). Gene expression was drive by a cytomegalovirus promoter; constructs also expressed enhanced green fluorescent protein (GFP) from an internal ribosome entry site (IRES). Controls were transfected with viruses expressing GFP alone. Virus production was performed at the HGTI Core Facility.

Viral Transfections

To transfect RGCs, female Sprague Dawley rats (160-180 gm) were anesthetized with ketamine-xylazine, and the back of the eye was exposed intraorbitally. After withdrawing 10 µl of fluid from the eye, approximately $10^{11}$ AAV particles in 10 µl of PBS were injected into the vitreous body using a micropipette, with care taken to avoid injury to the lens. Injections were done 2 weeks before optic nerve surgery to obtain high levels of transgene expression during the course of regeneration (Cheng et al., 2002).

Results

Transfection of RGCS with AAV Expressing C3 ADP-Ribosyltransferase

We injected mature rats intravitreally with AAV expressing either GFP alone (AAV-GFP) or clostridium botulinum C3 ADP-ribosyltransferase (and GFP after an IRES: AAV-C3-IGFP) to inactivate RhoA. By virtue of AAV2 being neuron specific, and by virtue of RGC somata and axons being superficial in the retina, this method results in the transfection of approximately 75% of RGCs but little transfection of other cell types (DiPolo et al., 1998; Martin et al., 2002; Fischer et al., 2004). RT-PCR demonstrated a strong C3 signal in retinas transfected with AAV-C3-IGFP but none in controls transfected with AAV-GFP (data not shown). The high efficiency and specificity of transfection was verified by double-labeling studies showing the GFP reporter to be expressed in the same cells that express the RGC-specific tubulin isoform βIII tubulin. Using RBD-GST for in situ "pull-down assays" to detect RhoA in the active (GTP-bound) state (Dubreuil et al., 2003), we observed considerable binding in normal RGCs but much less in RGCs transfected with AAV-C3-IGFP. Thus, AAV transfection leads to strong transgene expression in RGCs, and in the case of C3 expression, this inactivates RhoA.

RhoA Inactivation and Macrophage Activation have Synergistic Effects In Vivo

Figure 3A:
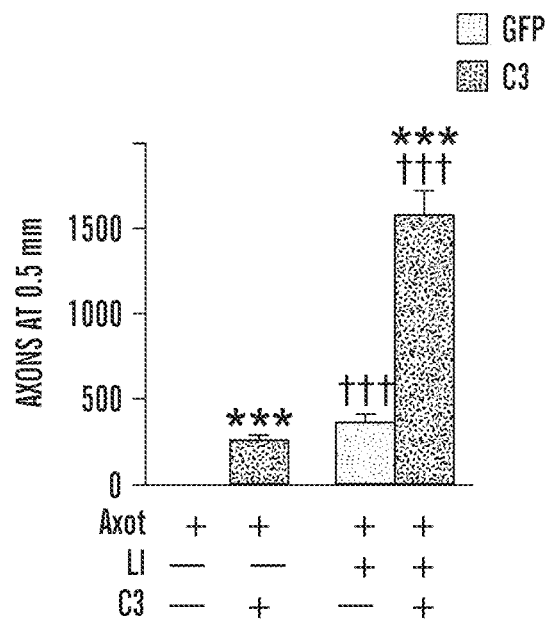
FIG. 3A, Quantitation of outgrowth (number of axons growing ≥500 μm beyond the injury site per optic nerve).

After allowing 2 weeks for transgenic C3 protein levels to become sufficiently high in RGCs, rats were re-anesthetized, and left optic nerve was crushed, and the lens was either injured or was left intact. Regeneration was evaluated 2 weeks later by GAP-43 immunostaining (Berry et al., 1996; Leon et al., 2000). As expected, AAV-GFP-transfected animals subjected to nerve crush alone showed no axons growing ≥500 μm beyond the lesion site 2 weeks after surgery (FIG. 8a), whereas similarly transfected animals with lens injury had, on average, approximately 400 axons extending ≥500 μm beyond the lesion site (FIG. 3a) (cf. Leon et al., 2000; Yin et al., 2003; Fischer et al., 2004). Even in the absence of lens injury, rats expressing C3 showed a modest number of axons passing through the lesion site; a higher percentage of these continued to extend ≥500 μm than was seen in GFP-expressing cases with lens injury, although the total number of axons reaching that criterion was lower (FIG. 3a). Combining C3 expression with lens injury resulted in unprecedented levels of axon regeneration. In every animal in this group, axon growth was so high as to obscure the discontinuity in GAP-43 immunostaining that is otherwise seen at the injury site. The number of axons extending ≥500 μm beyond the injury site was 4.5 times greater than after lens injury or C3 expression alone (FIG. 3a) (n=9; p<0.001) and higher than the effects of two added together. Thus, inactivation of RhoA and activation of the growth state of RGCs have synergistic effects in vivo.

C3 Expression Enhances RGC Survival

Figure 3B:
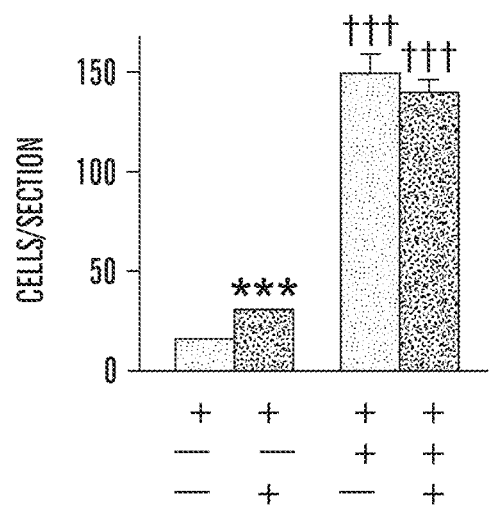
FIG. 3B, RGC survival (TUJ1$^+$RGCs per retinal cross section). Axot, Axotomy; LI, lens injury. ***Effect of C3 expression significant at $p<0.001$. †††, effect of intravitreal macrophage activation significant at $p<0.001$. Scale bar, 200 μm.
Figure 4:
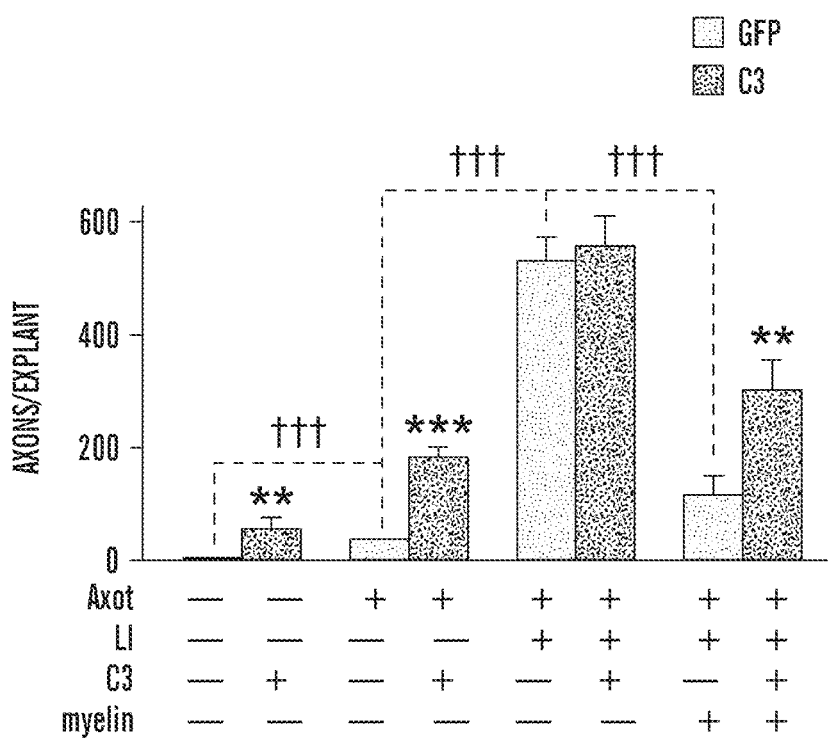
FIG. 4 shows the effect RhoA inactivation on axon regeneration depends on growth state and substrate: in vitro studies. Retinal explants were grown on poly-L-lysine-laminin substrate without or with myelin proteins 2 weeks after transfecting RGCs in vivo with genes expressing GFP alone or C3 expression has a small stimulatory effect under these conditions. Optic nerve injury 4d before explanting increases outgrowth slightly relative to controls and C3 expression enhances this growth considerably. Exposure of axotomized RGCs to the effects of lens injury increases outgrowth greatly, but C3 expression has no additional effect. Myelin proteins diminish outgrowth from growth-activated RCGs, and C3 expression partially reverses this inhibition. The graph shows the quantitation of results. Significance of C3 expression: $p<0.02$; *$p<0.001$; ††† differences between experimental treatments significant at $p<0.001$. Scale bar, 250 μm.

RhoA inactivation by C3 has been reported to protect neurons and other cells from apoptotic cell death (Dubreuil et al., 2003). To investigate whether C3 affects RGC survival in vivo, we counted the number of TUJ1-positive cells from four to six cross sections through each retina (near the level of the optic nerve head) 2 weeks after nerve crush and lens injury. C3 expression increased RGC survival after nerve crush approximately twofold relative to controls expressing GFP alone but did not enhance the strong neuroprotective effects of lens injury any further (FIG. 3b).

The Effects of C3 Expression on Growth State and Substrate

To investigate the effects of C3 expression in more detail, we examined the growth of retinal explants expressing C3 or GFP in culture. On a permissive laminin-poly-L-lysine substrate, control RGCs transfected with GFP showed almost no outgrowth, and C3 expression increased growth only slightly (FIG. 9) (p<0.001). Subjecting GFP-transfected RGCs to axotomy alone 4 d before-hand caused a moderate increase in regeneration compared with control RGCs (FIG. 9c,i) (p<0.001) (compare FIG. 1), and C3 transfection increased growth 4.6-fold when RGCs were in this state (p<0.001) (FIG. 9). Axotomy combined with lens injury increased growth 14-fold relative to RGCs subjected to axotomy alone, and this growth was not enhanced further C3 transfection (FIG. 9). Thus, when extrinsic inhibitors are absent, RhoA inactivation has only a small effect when the growth program of RGCs is not activated, a strong effect when the growth program is weakly activated by axotomy alone, but no additional effect when the growth program of RGCs is strongly activated.

When plated on a substrate containing myelin proteins, RGCs subjected to axotomy and lens injury showed far less growth than on poly-L-lysine-laminin (FIG. 9) (p<0.001) (cf. Fischer et al., 2004). Under these conditions, C3 expression increased the number of axons regenerating ≥50 μm 2.6-fold (FIG. 9) (p<0.02) and increased the number of axons growing ≥0.5 mm 3.8-fold (p=0.001; data not shown). Thus, when RGCs are in an active growth state, RhoA inactivation (by C3 expression) helps overcome the inhibitory effects of myelin.

Discussion

RGCs in an active growth state can regenerate injured axons for considerable distances through the optic nerve, but their growth is still limited by inhibitory signals associated with myelin and the glial scar. Inactivating RhoA greatly potentiated the amount of growth that occurred when the growth state of neurons was activated. These findings support that clinically successful regeneration requires a multi-pronged approach.

References

1. Aguayo A J, Rasminsky M, Bray G M, Carbonetto S, McKerracher L, Villegas-Perez M P, Vidal-Sanz M, Carter D A (1991) Degenerative and regenerative responses of injured neurons in the central nervous system of adult mammals. Philos Trans R Soc Lond B Biol Sci 331:337-343.
2. Bahr M, Vanselow J, Thanos S (1988) In vitro regeneration of adult rat ganglion cell axons from retinal explants. Exp Brain Res 73:393-401.
3. Bartlett J S, Samulski R J, McCown T J (1998) Selective and rapid uptake adeno-associated virus type 2 in brain. Hum Gene Ther 9:1181-1186.
4. Benowitz L I, Apostolides P J, Perrone-Bizzozero N, Finklestein S P, Zwiers H (1988) Anatomical distribution of the growth-associated protein GAP-43/B-50 in the adult rat brain. J Neurosci 8:339-352.
5. Berkelaar M, Clarke D B, Wang Y C, Bray G M, Aguayo A J (1994) Axotomy results in delayed death and apoptosis of retinal ganglion cells in adult rats. J Neurosci 14:4368-4374.
6. Berry M, Carlile J, Hunter A (1996) Peripheral nerve explants grafted into the vitreous body of the eye promote the regeneration of retinal ganglion cell axons severed in the optic nerve. J. Neurocytol 25:147-170.
7. Bregman B S, Kunkel-Bagden E, Schnell L, Dai H N, Gao D, Schwab M E (1995) Recovery from spinal cord injury mediated by antibodies to neurite growth inhibitors. Nature 378:498-501.
8. Chen M S, Huber A B, van de Haar M E, Frank M, Schnell L, Spillmann A A, Christ F, Schwab M E (2000) Nogo-A is a myelin-associated neurite outgrowth inhibitor and an antigen for monoclonal antibody IN-1. Nature 403:434-439.
9. Cheng H, Cao Y, Olson L (1996) Spinal cord repair in adult paraplegic rats; partial restoration of hind limb function. Science 273:510-513.
10. Cheng L, Sapieha P, Kittlerova P, Hauswirth W W, Di Polo A (2002) TrkB gene transfer protects retinal ganglion cells from axotomy-induced death in vivo. J. Neurosci 22:3977-3986.
11. Cui Q, Yip H K, Zhao R C, So K F, Harvey A R (2003) Intraocular elevation of cyclic AMP potentiates ciliary neurotrophic factor-induced regeneration of adult rat retinal ganglion cell axons. Mol Cell Neurosci 22:49-61.

12. Di Polo A. et al., (1998) Prolonged delivery of brain-derived neurotrophic factor by adenovirus-infected Muller cells temporarily rescues injured retinal ganglion cells. Proc. Natl. Acad. Sci. USA 95:3978-3983.
13. Domeniconi M, Cao Z, Spencer T, Sivasankaran R, Wang K, Nikulina E, Kimura N, Cai H, Deng K, Gao Y, He Z, Filbin M (2002) Myelin-associated glycoprotein interacts with the nogo66 receptor to inhibit neurite outgrowth. Neuron 35:283.
14. Dubreuil et al. (2003) Rho activation patterns after spinal cord injury and the role of activated Rho in apoptosis in the central nervous system. J. Cell Biol. 162:233-243.
15. Fischer D, Pavlidis M, Thanos S (2000) Cataractogenic lens injury prevents traumatic ganglion cell death and promotes axonal regeneration both in vivo and in culture. Invest Ophthalmol Vis Sci 41:3943-3954.
16. Fischer D, Heiduschka P, Thanos S (2001) Lens-injury-stimulated axonal regeneration throughout the optic pathway of adult rats. Exp Neurol 172:257-272.
17. Fischer D. et al., (2004) Counteracting the NOGO receptor enhances optic nerve regeneration if retinal ganglion cellas are in an active growth state. J. Neurosci 24:1646-1651.
18. Fischer D. et al., (2004) Switching mature retinal ganglion cells to a robust growth state in vivo: gene expression and synergy with RhoA inactivation.
19. Fournier A E, GrandPre T, Strittmatter S M (2001) Identification of a receptor mediating Nogo-66 inhibition of axonal regeneration. Nature 409:341-346.
20. GrandPre T, Li S, Strittmatter S M (2002) Nogo-66 receptor antagonist peptide promotes axonal regeneration. Nature 417:547-551.
21. GrandPre T, Nakamura F, Vartanian T, Strittmatter S M (2000) Identification of the Nogo inhibitor of axon regeneration as a Reticulon protein. Nature 403:439-444.
22. Guest J D, Hesse D, Schnell L, Schwab M E, Bunge M B, Bunge R P (1997) Influence of IN-1 antibody and acidic FGF-fibrin glue on the response of injured corticospinal tract axons to human Schwann cell grafts. J Neurosci Res 50:888-905.
23. Kim J E, Liu B P, Yang X, Strittmatter S M (2003a) Recovery from spinal cord injury in mice lacking the Nogo-66 receptor. Program No 415.11, Abstract Viewer and Itinerary Planner. Washington, D.C.: Society Neuroscience, 2003 CD-ROM.
24. Kim J E, Li S, GrandPre T, Qiu D, Strittmatter S M (2003b) Axon regeneration in young adult mice lacking nogo-a/b. Neuron 38:187-199.
25. Kumagi N et al. (1993) ADP-ribosylation of rho p21 inhibits lysophosphatidic acid-induced protein tyrosine phosphorylation and phosphatidylinositol 3-kinase activation in cultured Swiss 3T3 cells. J. Biol. Chem. 268:24535-24538.
26. Lehmann M, Fournier A, Selles-Navarro I, Dergham P, Sebok A, Leclerc N, Tigyi G, McKerracher L (1999) Inactivation of Rho signaling pathway promotes CNS axon regeneration. J. Neurosci. 19:7537-7547.
27. Leon S, Yin, Y, Nguyen J, Irwing N, Benowitz K I (2000) Lens injury stimulates axon regeneration in the mature rat optic nerve. J Neurosci 20:4615-4626.
28. Li Y, Irwin N, Yin Y, Lanser M, Benowitz L I (2000) Axon regeneration in goldfish and rat retinal ganglion cells: differential responsiveness to carbohydrates and cAMP. J Neurosci 23:7830-7838.
29. Liu B P, Fournier A, GrandPre T, Strittmatter S M (2002) Myelin-Associated Glycoprotein as a Functional Ligand for the Nogo-66 Receptor. Science 27:27.
30. Liu Y. et al., (1994) Intracellular sorting of neuromodulin (GAP-43) mutants modified in the membrane targeting domain. J. Neurosci. 14:5807-5817.
31. Martin K R, Klein R L, Quigley H A (2002) Gene delivery to the eye using adeno-associated viral vectors. Methods 28:267-275.
32. McKeon R J, Hoke A, Silver J (1995) Injury-induced proteoglycans inhibit the potential for laminin-mediated axon growth on astrocytic scars. Exp Neurol 136:32-43.
33. McKerracher L, David S, Jackson D L, Kottis V, Dunn R J Braun P E (1994) Identification of myelin-associated glycoprotein as a major myelin-derived inhibitor of neurite growth. Neuron 13:805-811.
34. Moon, L D, Asher R A, Rhodes K E, Fawcett J W (2001) Regeneration of CNS axons back to their target following treatment of adult rat brain with chondroitinase ABC. Nat Neurosci 4:465-466.
35. Mukhopadhyay G, Doherty P, Walsh F S, Crocker P R, Filbin M T (1994) A novel role for myelin-associated glycoprotein as an inhibitor of axonal regeneration. Neuron 13:757-767.
36. Niederost B, Oertle T, Fritsche J, McKinney R A, Bandtlow C E (2002) Nogo-A and myelin-associated glycoprotein mediate neurite growth inhibition by antagonistic regulation of RhoA and Rac1. J Neurosci 22:10368-10376.
37. Oertle T, van de Haar M E, Bandtlow C E, Robeva A, Burfeind P, Buss A, Huber A B, Simonen M, Schnell L, Brosamle C, Kaupmann K, Vallon R, Schwab M E (2003) Nogo-A inhibits neurite outgrowth and cell spreading with three discrete regions. J Neurosci 23:5393-5406.
38. Oster S F, Bodeker M O, He F, Sretavan D W (2003) Invariant Sema5A inhibition serves an ensheathing function during optic nerve development. Development 130:775-784.
39. Ramon y Cajal S (1991) Degeneration and Regeneration of the Nervous System. New York: Oxford University Press.
40. Schaden H. Stuermer C A, Bahr M (1994) GAP-43 immunoreactivity and axon regeneration in retinal ganglion cells of the rat. J Neurobiol 25:1570-1578.
41. Schnell L, Schneider R, Kolbeck R, Barde Y A, Schwab M E (1994) Neurotrophin-3 enhances sprouting of corticospinal tract during development and after adult spinal cord lesion. Nature 367:170-173.
42. Sicotte M, Tsatas O, Jeong S Y, Cai C Q, He Z, David S (2003) Immunization with myelin or recombinant Nogo-66/MAG in alum promotes axon regeneration and sprouting after corticospinal tract lesions in the spinal cord. Mol Cell Neurosci 23:251-263.
43. Simonen M, Pedersen V, Weinmann O, Schnell L, Buss A, Ledermann B, Christ F, Sansig G, van der Putten H, Schwab M E (2003) Systemic deletion of the myelin-associated outgrowth inhibitor nogo-a improves regenerative and plastic responses after spinal cord injury. Neuron 38:201-211.
44. Spillmann A A, Bandtlow C E, Lottspeich F, Keller F, Schwab M E (1998) Identification and characterization of a bovine neurite growth inhibitor (bNI-220). J Biol Chem 273:19283-19293.
45. Steward O, Zheng B, Tessier-Lavigne M (2003) False resurrections: distinguishing regenerated from spared axons in the injured central nervous system. J Comp Neurol 459:1-8.
46. Wang K C, Kim J A, Sivasankaran R, Segal R, He Z (2002a) p75 interacts with the Nogo receptor as a co-receptor for Nogo, MAG and OMgp. Nature 420:74-78.

47. Wang K C, Koprivica V, Kim J A, Sivasankaran R, Guo Y, Neve R L, He Z (2002b) Oligodendrocyte-myelin glycoprotein is a Nogo receptor ligand that inhibits neurite outgrowth. Nature 417:941-944.
48. Woolf C J (2003); No Nogo: now where to go? Neuron 38:153-156.
49. Yin Y, Cui Q, Li Y, Irwin N, Fischer D, Harvey A R, Benowitz L I (2003) Macrophage-derived factors stimulate optic nerve regeneration. J Neurosci 23:2284-2293.
50. Zheng B, Ho C, Li S, Keirstead H, Steward O, Tessier-Lavigne M (2003) Lack of enhanced spinal regeneration in nogo-deficient mice. Neuron 38:213-224.
51. Zuber et al. (1989) A membrane targeting signal in the amino terminus of the neuronal protein GAP-42. Nature 341: 345-348.

Example III

Inosine Alters Gene Expression and Axonal Projections in Neurons Contralateral to a Cortical Infarct and Improves Skilled Use of the Impaired Limb In the US alone, over 350,000 people who survive a stroke each year suffer persistent sensorimotor and/or cognitive deficits that significantly impair daily living. Current treatments are limited to the use of thrombolytic agents and physical therapy. Strategies to improve outcome by limiting secondary injury, while successful in animal studies, have shown little benefit clinically (Dobkin, 2003). Another strategy for improving outcome af-ter stroke might be to stimulate the reinnervation of brain regions that have lost their normal inputs. After focal brain injury, undamaged neurons undergo changes in their dendritic arbors (Allred and Jones, 2004; Hsu and Jones, 2006; Papadopoulos et al., 2006) and axonal projections (Carmichael et al., 2001; Carmichael, 2003; Dancause et al., 2005; Nudo, 2006) that enable them to assume some of the functions formerly mediated by the damaged areas (Nudo, 2007). Thus, treatments that enhance anatomical reorganization may help improve functional outcome after stroke.

Factors that limit anatomical reorganization after brain injury include the low intrinsic potential of most CNS neurons to extend axons, and the many inhibitory proteins associated with myelin and the perineuronal net. In a unilateral stroke model, interfering with the inhibitory protein Nogo or one of its receptors, NgR, enables corticospinal neurons (CSNs) on the intact side of the brain to sprout axon collaterals into the denervated side of the spinal cord and improves animal's ability to use the affected paw (Papadopoulos et al., 2002; Emerick et al., 2003; Lee et al., 2004; Cafferty and Strittmatter, 2006).

A complementary way to promote rewiring after stroke is to augment neurons' intrinsic growth state (Kawamata et al., 1997). The purine nucleoside inosine activates Mst3b, a protein kinase that is part of a cell-signaling pathway that regulates axon outgrowth (Irwin et al., 2006). Inosine stimulates axon outgrowth from several types of neurons in culture (Benowitz et al., 1998; Irwin et al., 2006; Zurn et al., 1988), and in vivo, it enhances the ability of neurons contralateral to an injured hemisphere to extend axon collaterals into denervated parts of the brainstem and spinal cord (Chen et al., 2002; Smith et al., 2007). In the present study, a more refined injury model is used to show that inosine affects gene expression in CSNs contralateral to a stroke, enhances these neurons' ability to extend new axons and form synaptic-like structures on the denervated side of the spinal cord, and almost completely restores fine motor control with the forepaw previously controlled by the damaged hemisphere.

Materials and Methods
Stroke Surgery.

All procedures were carried out in accordance with NIH Guidelines with the approval of Children's Hospital Animal Care and Use Committee. Unilateral in-farcts were induced in the sensorimotor cortex of adult Sprague-Dawley rats (275-300 g; Charles River Laboratories, Wilmington, Mass.) using the photothrombotic model of focal ischemia (Markgraf et al., 1993). Briefly, rats were anesthetized with a combination of ketamine (75 mg/kg) and Domitor (medetomidine; 0.5 mg/kg) and a 15 mm skin incision was made at the midline rostral to the posterior suture. A craniotomy was performed over the sensorimotor cortex using a hand-held drill to open a window that spanned medio-laterally between the sagittal sinus and temporal ridge, and rostro-caudally between Bregma +2.5 mm and Bregma −3.5 mm. The photosensitive dye Rose Bengal was injected into the femoral vein, and a fiber-optic cable connected to a xenon light source was centered over the craniotomy, focusing light directly on the exposed region of the brain for 30 minutes. A green filter fitted over the bulb restricted illumination to ~525 nm, a wavelength that excites Rose Bengal and causes it to release free radical species. The subsequent damage to endothelial cells in exposed portions of the cortical vasculature causes platelet aggregation, resulting in severe focal ischemia. As shown below, infarcts had a diameter of 6-7 mm and were restricted to cortical tissue and some underlying white matter. Control animals were generated using the same surgical procedure but without photo-activation of Rose Bengal. Animals with strokes were randomly assigned to receive a continuous infusion of either saline (0.9%, Baxter Scientific; n=12), inosine (50 mM in saline, Sigma-Aldrich Co., St. Louis, Mo.; n=12), NEP1-40 (500 µM in 2.5% DMSO/97.5% saline; n=12), or inosine +NEP1-40 (n=12) into the cisterna magna using osmotic minipumps (0.25 µl/h, Alzet model 2004, Durect Corpora-tion, Palo Alto, Calif.). In addition to these, a separate set of animals with the same 4 groups (n=12 in each) was created for a long-term behavioral study. Because CSF drug concentrations presumably require several hours to achieve steady-state levels when delivered via slow-releasing osmotic pumps, all animals received a 25 µl intraventricular bolus of the appropriate agent prior to pump placement. Pumps were tucked between the shoulder blades and infusion needles were secured onto the cranium with a silicon-based glue. The incision was closed with silk sutures and cleaned with beta-dine and ethanol pads. For 72 hours following surgery, animals received twice-daily, subcu-taneous injections of Buprenex (buprenorphine; Reckitt Benkiser Pharmaceuticals Inc., Richmond, Va.) for pain management.

Behavioral Testing.

In animals in which both behavioral testing and anatomical tracing was performed, animals were tested at 7, 14, 21, and 28 days after surgery, whereas in the long-term behavioral study, minipumps were removed after 4 weeks and testing was continued weekly for another 4 weeks. All testing was done by an experimenter blind to the animals' treatments. A skilled forelimb-reaching task was used to test functional recovery after stroke. The task requires the rat to reach with either paw through a narrow slit in a Plexiglas box, grasp a banana-flavored food pellet (Bio-Serv, Inc., Frenchtown, N.J.) from a platform, and bring it successfully to the mouth (Allred and Jones, 2004; Luke et al., 2004). Three days prior to and during training, animals were maintained on a restricted diet of banana-flavored pellets to remove novelty-induced hesitation and to increase motivation. Rats were trained 30-60 minutes per day with each paw for two weeks or until they reached a baseline performance of 20-30 successful reaches in a two-minute period. At the end of the training period but prior to surgery, each animal was tested for the number of pellets it successfully grasped and ate in a two-minute trial, making certain that animals were motivated and stress-free. This became the "baseline" score, to which subsequent scores were normalized, allowing consideration of possible individual differences in motivation and competence as a biasing factor for overall performance. Performance was recorded only if rats retrieved a minimum of 25 pellets within the two minute interval. Relatively little inter-animal variation was seen in baseline performance once rats were well-trained. In postsurgical testing, performance was likewise scored only when animals were fully engaged and performing the task at a relatively consistent level. Scores from the unimpaired paw were used to gauge animals' engagement and motivation. Data were analyzed using a regular two-way ANOVA. Bonferroni's post-test was used to compare data sets.

Anterograde Tracing of Crossing Fibers.

In groups treated for four weeks after stroke, animals were re-anesthetized, the infusion needle and pump were removed, and a craniotomy was performed over the uninjured SMA. The anterograde tracer bioti-nylated dextran amine (BDA: Molecular Probes: 10% wt/vol in sterile saline) was injected stereotaxically at depths of 0.5, 1.0, and 2.0 mm below the cortical surface at 18 standardized points distributed over the sensorimotor cortex (70 nl per injection; Nano-ject, Drummond Scientific, Broomall, Pa.). Two weeks later, animals were anesthetized and perfused transcardially with 0.9% saline followed by 4% paraformaldehyde. The brain and spinal cord were dissected and post-fixed overnight in 4% paraformaldehyde, followed by 10% and 30% sucrose solutions over the next few days. Tissue was em-bedded in OCT Tissue Tek Medium (Sakura Finetek USA Inc., CA) and frozen on dry ice. Forty micron free-floating sections were cut in the coronal plane on a Frigo-Jung 8500 cryostat. Free-floating spinal cord sections were used to detect crossing fibers using avidin-biotin complex conjugated to horseradish peroxidase (Vectastain ABC Kit; Vector Laboratories), followed by Vector SG (Vector Laboratories) as a chromagen. Sections were mounted on pre-coated slides and lightly counterstained with eosin to distinguish grey and white matter boundaries. Six to ten sections spanning a distance of 1.2 mm were examined and quantified for (a) BDA-labeled axon profiles ≥40 µm in length within the dorsal funiculus on the denervated side of the spinal cord (ipsilateral to the BDA injection and contralateral to the injury); (b) BDA+axons≥40 µm in length in the gray matter of the denervated side of the spinal cord, and (c) BDA+axons≥200 µm in length on the denervated side. Axon length was measure in the transverse plane. Average numbers of axons were calculated and converted to axons per mm of spinal cord.

Determination of Lesion Severity.

Sections through the telencephalon were cut at 10 µm, mounted on slides, and stained with Crystal Violet to determine the extent of the lesions. Sections were scanned using a high resolution Epson Perfection 3490 PHOTO scanner. The area of the injured and uninjured hemisphere of each section was determined using NIH Image-J software. Lesion area was determined by subtracting the area of tissue remaining in the injured hemisphere from that in the uninjured hemisphere in sections spaced 250 µm apart spanning the full rostrocaudal extent of the lesion. Lesion volume was extrapolated from these data. Lesions were redrawn onto standard sections from a rat brain atlas (Paxinos and Watson, 1998). Representations of the injury were created from tracings of scanned sections in Adobe Photoshop.

Retrograde Labeling of Layer 5 Pyramidal Cells.

In a separate group of animals (n=20), layer V pyramidal cells of the sensorimotor cortex were retrogradely labeled by injecting Alexa-Fluor-488-conjugated cholera toxin B subunit (CTB; 300 U/µl in sterile saline) into the cervical spinal cord. For this, animals were anesthetized with a combination of ketamine and Domitor (medetomidine) and a laminectomy was performed at the cervical level of the spinal cord (C2-C4). CTB was stereotaxically delivered into four sites lateral to the corticospinal tract. Injections (1.3 µl) were spaced 1 mm apart on the rostro-caudal axis, and were made 0.5 mm to the left and right of the midline. After allowing two weeks for transport of the tracer, we performed either sham surgery with no treatment (n=6) or stroke surgery combined with saline (n=3) or inosine (n=4) treatment as described above. Seven days later, animals were decapitated under transient gas anesthesia, brains were removed and rinsed in cold RPMI medium, and a tissue block containing the sensorimotor cortex was dissected and placed in OCT Tissue Tek Medium (Sakura Finetek USA Inc., CA) on dry ice within five minutes of death. Ten µm sections were cut onto precleaned Gold Seal RITE-ON glass slides (Gold Seal Prod-ucts, Portsmouth, N.H.), placed on dry ice, and rapidly stored at −80° C. The numbers of cases shown above represent the cases that were found to be suitable for further analysis based upon quality of the RNA and within-group reproducibility (see below).

Laser-Capture Microdissection (LCM) and Microarray Analysis.

Slide-mounted sections were thawed and dehydrated in RNAse-free ethanol gradients and xylene. Retro-gradely labeled, fluorescent cortical pyramidal cells in the undamaged hemisphere were individually captured using the Arcturus VERITAS system. ≥500 cells were collected from each animal and stored in Arcturus extraction buffer at −80° C. Total RNA was extracted from cells using the Micro-to-Midi TotalRNA Purification System (Invitrogen, Carlsbad Calif.) and double-amplified using the TargetAmp 2-Round Aminoallyl-aRNA Amplification kit 1.0 (Epicentre, Madison, Wis.). Amplified RNA was checked for average fragment length using the Agilent RNA 6000 Nano LabChip kit (Agilent Technologies, Santa Clara, Calif.) and then biotinylated and hybridized (1 µg) on Illumina RatRef-12 Expression BeadChip arrays (Illumina, San Diego Calif.), querying the expression of >22,000 RefSeq-curated rat transcripts. Results were obtained from a total of 15 samples representing 6 untreated controls, 4 animals with stroke treated with saline and 5 animals with stroke treated with inosine. Slides were processed and scanned with Illumina BeadStation platform according to the manufacturer protocol.

Raw data was analyzed using Bioconductor packages (www.bioconductor.org, (Gentleman et al., 2004)). Low level quality-control analysis was performed using inter-array Pearson correlation and clustering based on variance. Two arrays (1 saline and 1 inosine-treated) were outliers and were excluded from the analysis. Data was normalized using quantile normalization, and analysis of differential expression was performed using a linear model fitting (LIMMA package, (Smyth, 2005). Differentially expressed genes were classified according to gene ontology using Bioconductor packages and online tools (DAVID, http://david.abcc.ncifcrf.gov/). Pathway analysis was carried out using Ingenuity Pathway Analysis (Ingenuity Systems, www.ingenuity.com).

Results
Lesion Placement and Size

Figure 10A:
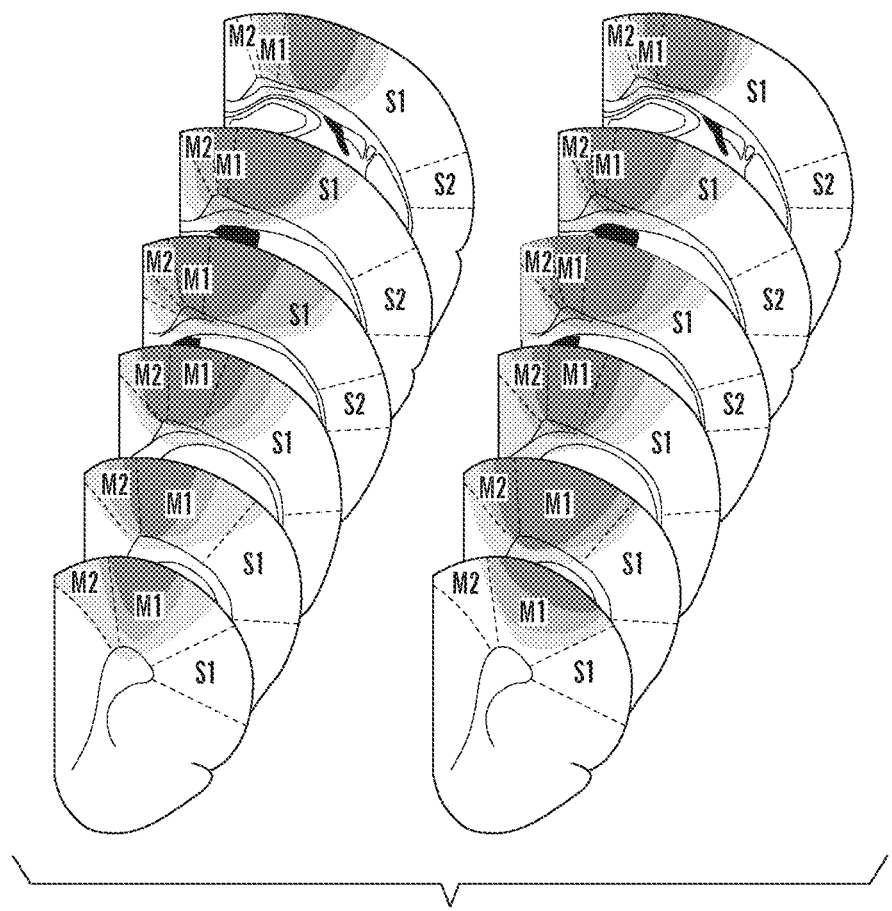
FIG. 10A-FIG. 10B shows unilateral brain damage after focal ischemia.
Figure 10B:
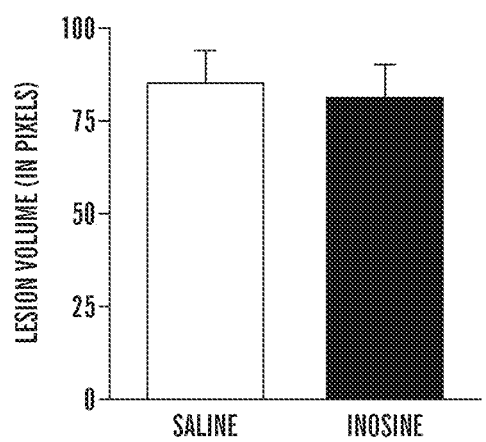
Figure 15A:
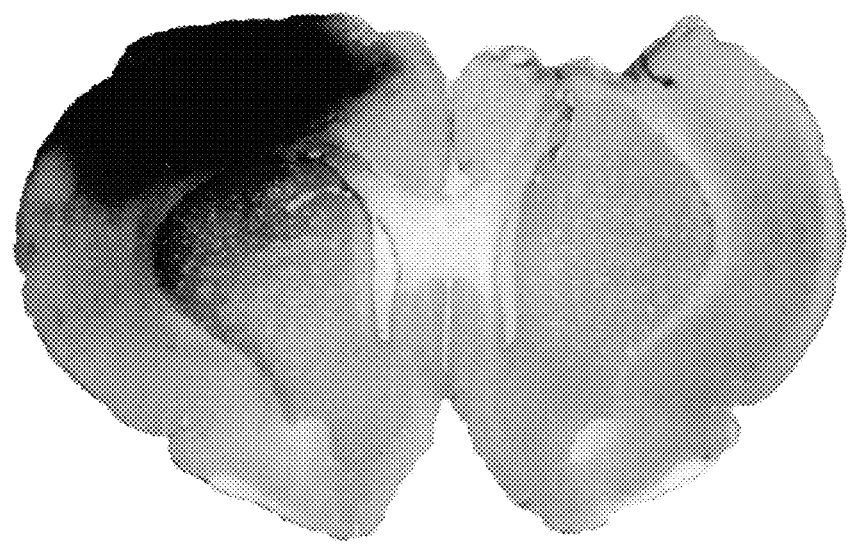
Figure 15B:
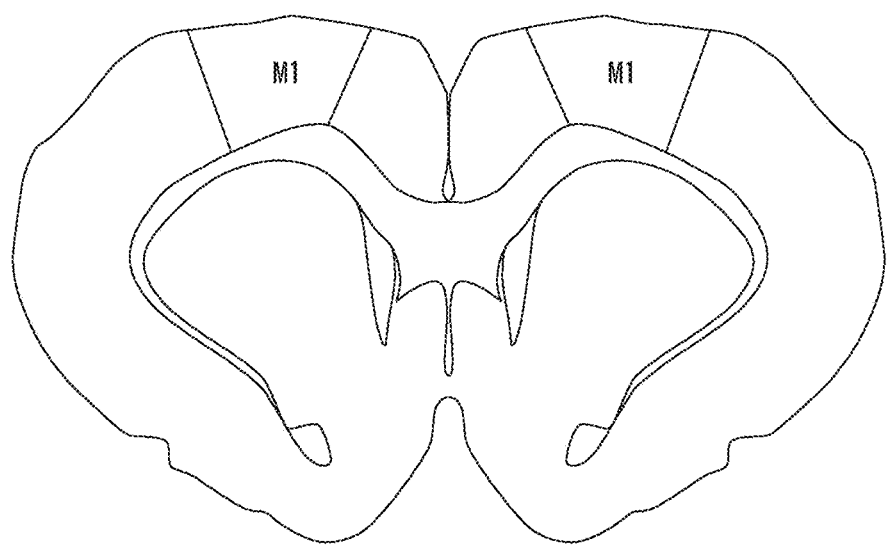
Figure 16A:
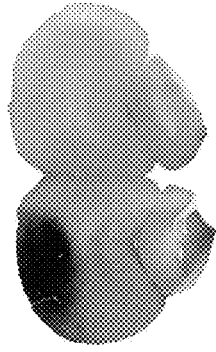
FIG. 16A-FIG. 16I shows range of lesion sizes. Serial sections through the brains of individual cases with the smallest (FIG. 16A-C), average (FIG. 16 D-F) and largest (FIG. 16G-I) lesions in our study. The lesions are on the right sides of the sections, whereas the left sides show the extent of BDA labeling. Note that the brain is distorted during processing in the case with the largest lesion. Measurements of lesion size are based on the difference between the cross-sectional area of the damaged side and the intact side over 20 equally spaced sections through the lesioned area.
Figure 16B:
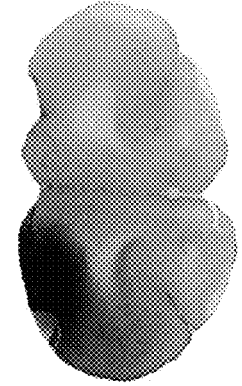
Figure 16C:
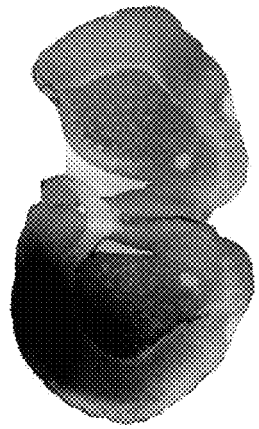
Figure 16D:
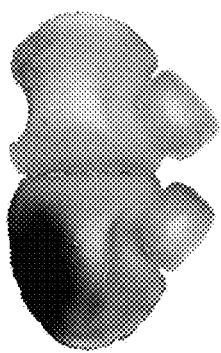
Figure 16E:
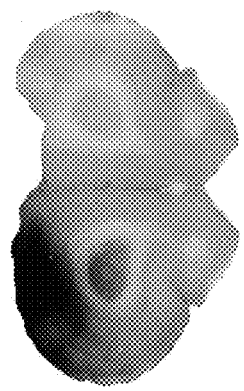
Figure 16F:
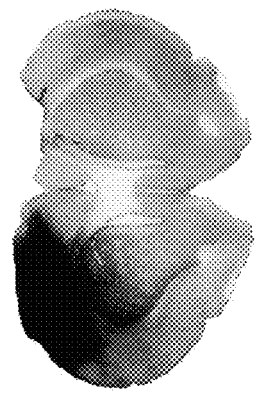
Figure 16G:
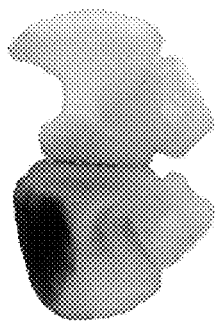
Figure 16H:
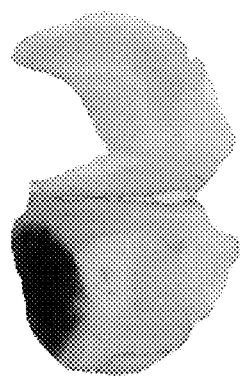
Figure 16I:
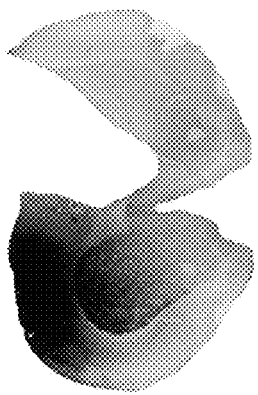

A photothrombotic stroke model was used to generate unilateral ischemic lesions centered in the forelimb motor area of the cortex. The infarct area was determined using stereotaxic coordinates and was verified by histological analysis. Lesions were restricted to one hemisphere and included the caudal forelimb area of the primary motor cortex along with varying amounts of adjacent cortex (FIG. 10A and FIGS. 15 and 16). Lesion size varied among animals in each group, but there were no systematic between-group differences (lesion size [in pixels]=85.4±8.2 d [mean±S.E.M] for the saline-treated group and 81.1±8.6 for the inosine-treated group: difference not significant). This finding suggests that inosine was not neuroprotective. This conclusion is further supported by the absence of any difference between inosine- and saline-treated cases in the number and size of profiles expressing activated caspase-3, as quantified focally in a standardized area on the periphery of the stroke (Caspase-3 profiles in saline-treated group=11.8±1.1, and in inosine treated group=11.9±1.5). Cannulas delivering inosine or saline, placed into the lateral ventricle caudal to the forelimb motor area, did not cause excessive tissue damage.

Figure 11A:
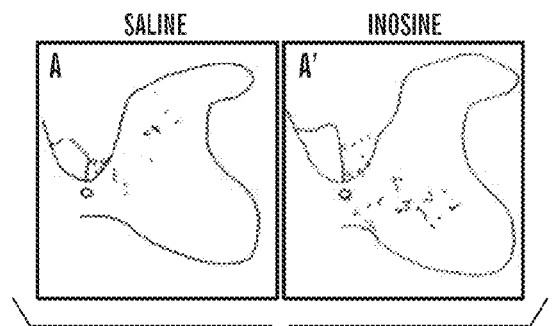
FIG. 11A-FIG. 11H shows inosine enhances CST sprouting on the denervated side of the spinal cord.

Inosine Promotes the Sprouting of CST Axons from the Intact Hemisphere into the Denervated Side of the Spinal Cord To investigate the effect of inosine on CST reorganization, biotinylated dextran amine (BDA) was injected into multiple sites in the forelimb motor area of the undamaged hemisphere at the completion of behavioral testing (FIG. 15 and FIG. 16). After allowing two weeks for BDA to be transported down the length of the corticospinal tract (CST), animals were euthanized and prepared for histology. Relative to controls, animals treated with inosine showed a three-fold increase in the number of CST fibers that originate in the undamaged hemisphere and re-cross the midline to enter the denervated dorsal funiculus ($P<0.01$, FIG. 11 A/A', FIG. 11E). Within the gray matter on the denervated side of the cord, inosine induced a 2.5-fold increase in the number of labeled fibers ≥40 μm in length (FIG. 11F, $P<0.01$), and increased the number of lengthy axons (>200 μm) 3.5-fold (FIG. 11G, $P<0.01$). Midline CST axons were observed crossing at the level of the cervical spinal cord, for example a BDA-labeled CST axon that arose from the undamaged hemisphere and crossed into the denervated side of the spinal cord was observed (not shown).

Figure 11B:
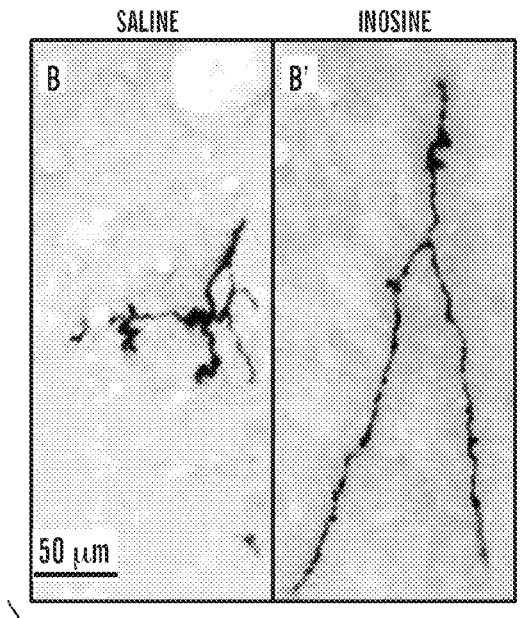
Figure 11C:
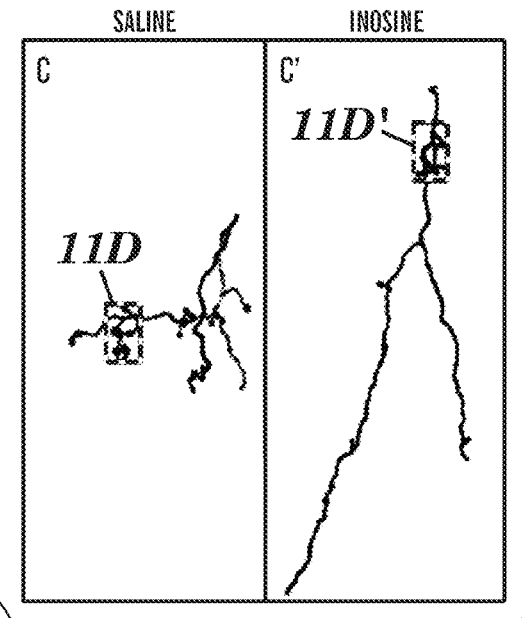
Figure 11D:
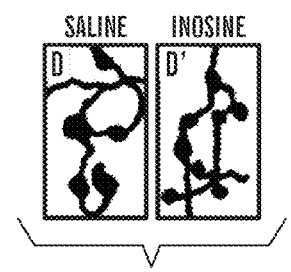
Figure 11E:
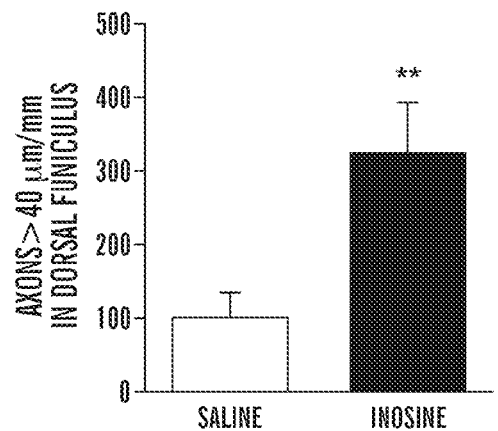
Figure 11F:
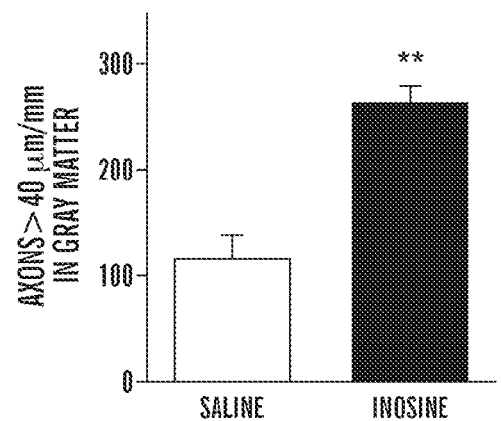
Figure 11G:
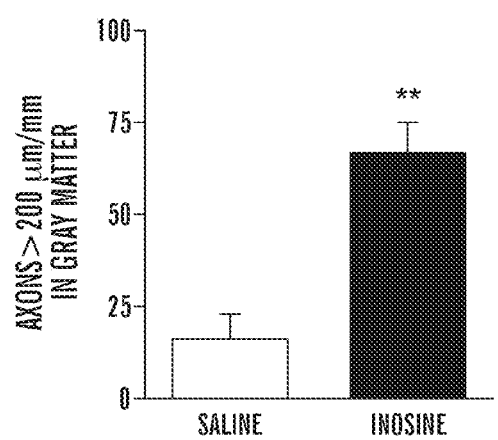
Figure 11H:
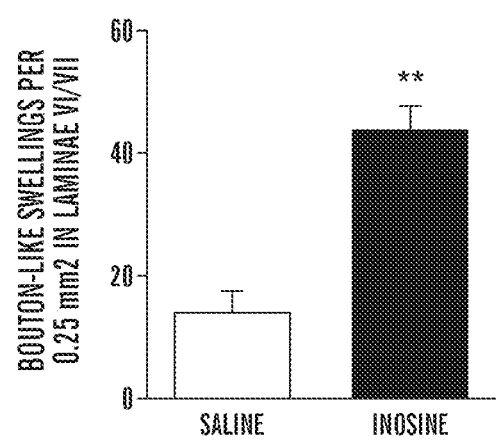

At high magnification, labeled CST axons showed numerous bouton-like structures, local swellings that were ≥2× the width of the axons (FIG. 11B, B'). Camera lucida tracings demonstrate the presence of both en passant and terminal boutons (FIG. 11). These structures are known to correspond to synapses at the electron microscopic level (Lagerback et al., 1981; Havton and Kellerth, 1987), and were observed in both saline and inosine-treated cases in proportion to the length of axons in the gray matter. Quantifying the density of these structures within a 0.25 mm² box spanning Laminae VI and VII using a 100× oil objective revealed that inosine tripled the number of synaptic bouton-like structures (FIG. 11H).

Inosine Did not Alter CST Reorganization in the Absence of Brain Injury

To investigate this question, animals underwent sham surgeries (craniotomies, Rose Bengal injections, no photoactivation) and received inosine or saline into the lateral ventricle of the right hemisphere for 4 weeks. One hemisphere was then labeled with BDA and the animals were prepared for histology 2 weeks later. Inosine- and saline-treated animals showed similarly small numbers of labeled CST axons in the spinal grey matter ipsilateral to the labeled hemisphere (60±6.7 axons/mm for saline-treated cases, and 77.5±9.0 for inosine-treated cases: t=1.56, df=11, P~0.15), indicating that inosine does not stimulate CST axons to sprout in the absence of brain injury and target denervation. To investigate whether stroke per se causes significant anatomical reorganization, animals in Expt. III (Table 1) underwent unilateral brain injury but received no further treatment. Four weeks later, the undamaged hemisphere was labeled with BDA and, after allowing another 2 weeks for BDA transport, animals were prepared for histology. Animals with strokes showed approximately 5 times more CST fibers that projected from the unaffected hemisphere into the ipsilateral cervical grey matter than sham-operated controls (40±16 axons/mm without stroke vs. 217.5±57.2 with stroke, $P<0.001$). Together, these data suggest that inosine augments a naturally occurring reorganization of CST fibers after stroke, but does not alter CST organization in the absence of brain injury.

To examine the time course of CST reorganization, a separate group of animals was generated (N=6 per group) in which CST axons arising from the intact hemisphere were labeled two weeks after stroke, rather than 4 weeks. No significant differences were found in the number of BDA-labeled CST fibers between inosine- and saline-treated cases (data not shown).

Inosine Improves Skilled Use of the Denervated Forepaw

Figure 12A:
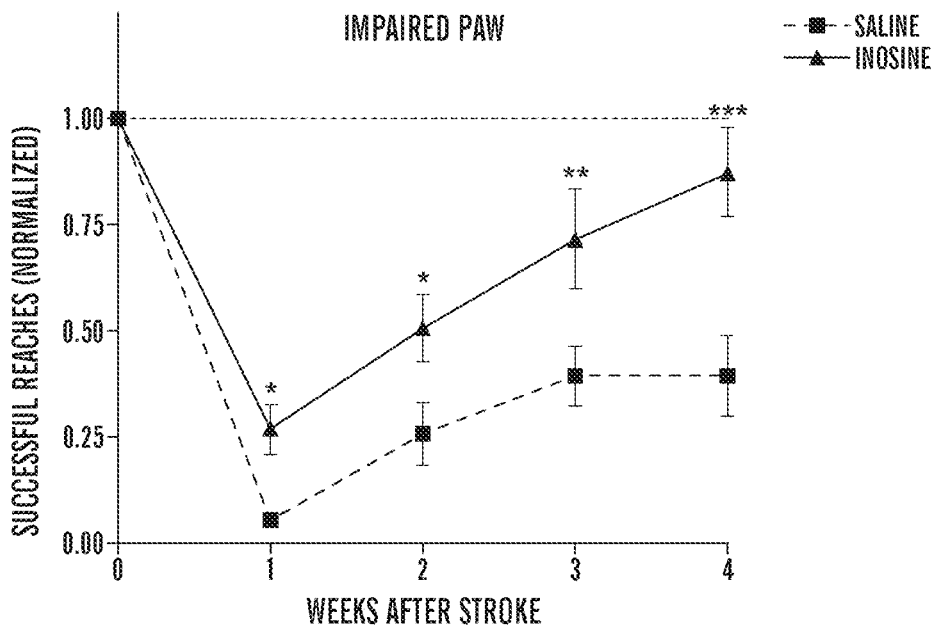
FIG. 12A-FIG. 12B are line graphs showing that inosine enhances functional recovery after stroke. Animals were trained to retrieve food pellets through a restricted opening with either paw prior to surgery and were then tested weekly beginning one week later by a blinded observer. Scores are reported as percentage of pre-operative performance.
Figure 12B:
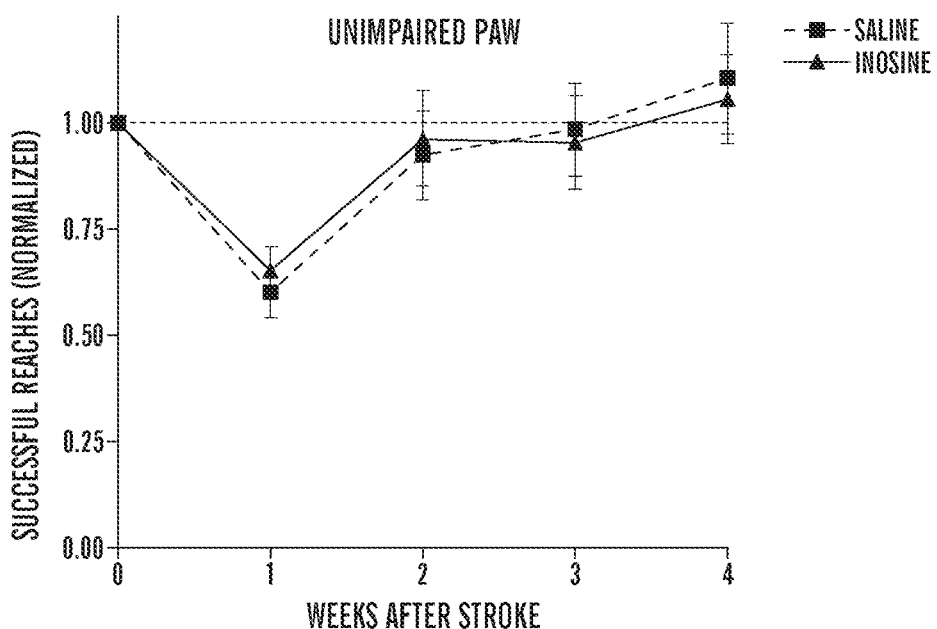

By using a photothrombotic injury model, it was possible to limit injury to the primary motor area and surrounding neocortex with only modest subcortical damage. This enabled the investigation of recovery of skilled behavior with a minimum of nonspecific functional deficits. All animals were trained to criterion with both paws before surgery and the presurgical scores were used to normalize their scores after stroke. In the first week after stroke, all animals suffered a dramatic drop in their ability to retrieve food pellets with the paw contralateral to the infarct (FIG. 12A). Saline-treated animals initially showed almost no ability to grasp the food pellets, though performance recovered to 35-40% of their pre-operative level over the next 3-4 weeks. The performance of inosine-treated animals was superior to that of controls at 1 week ($P<0.01$) and became increasingly so over time. By week 4, inosine-treated animals were performing at approximately 80% of their baseline levels (FIG. 12A: difference from controls significant at $P<0.01$). The experimental and control groups both performed normally with the unaffected paw (FIG. 12B), indicating that the deficits seen with the impaired paw are not attributable to changes in motivation or overall activity levels.

Persistent Effects of Treatment on Functional Recovery

Figure 13A:
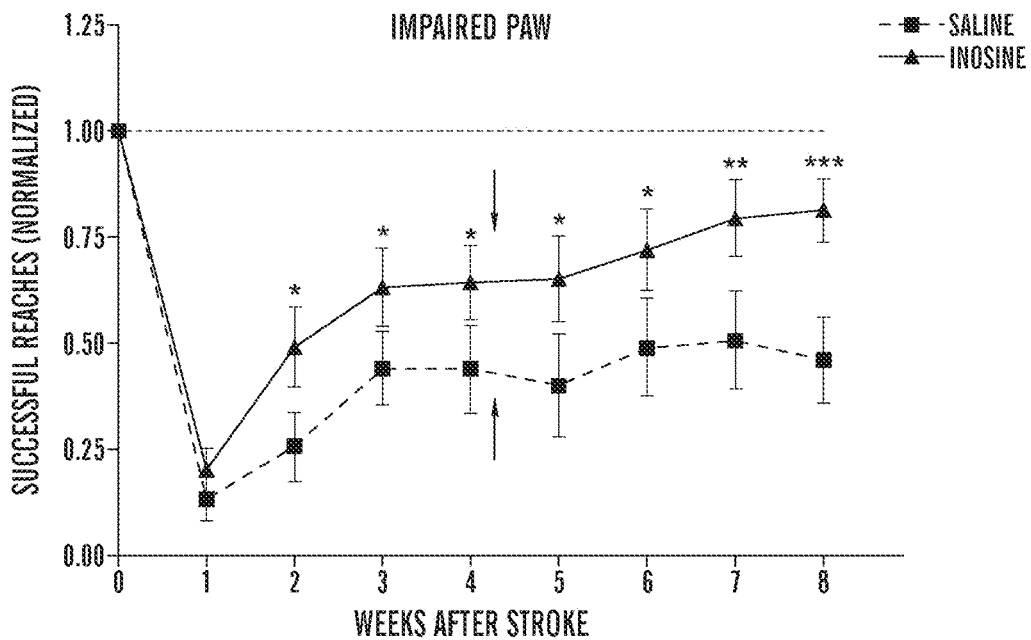
FIG. 13A-FIG. 13B are line graphs showing that functional improvements persist after the cessation of treatment. Animals were treated as in FIG. 12 but were tested for an additional 4 weeks after treatments ended with either the paw contralateral to the stroke (FIG. 13A) or the unaffected paw (FIG. 13B). Performance with the affected paw failed to improve after 3-4 weeks in saline-treated animals, but remained high and even tended to improve after inosine treatment ended.
Figure 13B:
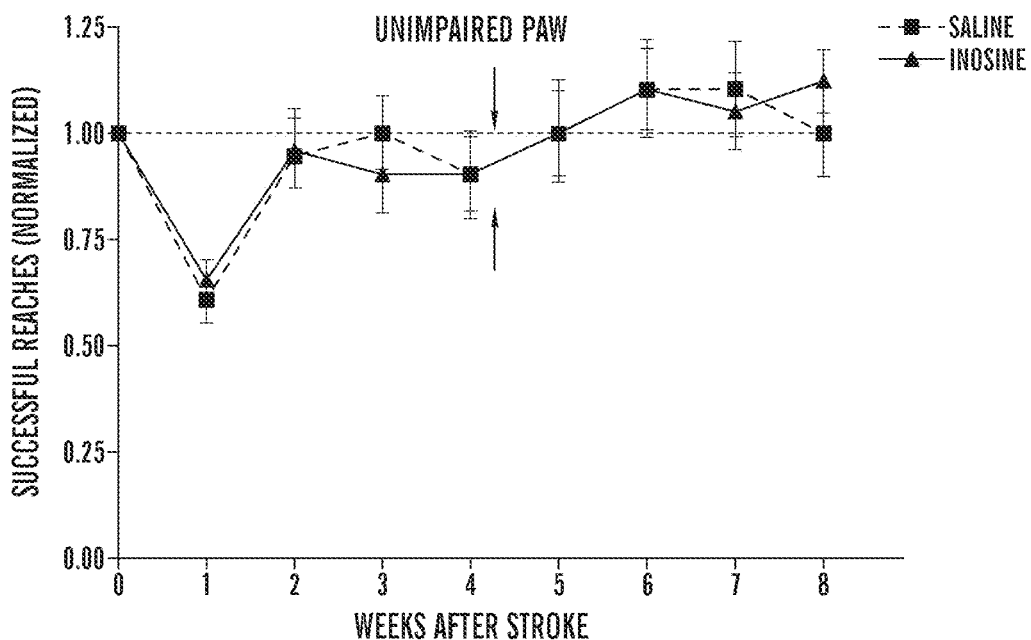

A separate set of animals was used to investigate whether the functional effects of inosine would persist after treatment ended. Animals were treated and tested for 4 weeks as before, then tested for an additional 4 weeks after minipumps were removed. As before, saline-treated animals showed almost no ability to retrieve food pellets in the first week and recovered to about 40% of their preoperative level by week 3-4. No further improvements were seen at later time points (FIG. 13A). In contrast, inosine-treated animals continued to perform well and even improve over time, going from ~70% of baseline at week four to ~80% at week eight. The performance of inosine-treated animals was significantly better than that of saline-treated controls from week 2 on ($P<0.05$ for weeks 2-6, $P<0.01$ for weeks 7 and 8). No differences were detected in animals' performance with the unimpaired paw (FIG. 13B). The results of this study confirm the effects of inosine seen in the first part of the study, and show that these effects persist for at least a month after treatment ends.

Inosine Alters Gene Expression in Neurons Contralateral to the Lesion

Figure 14A:
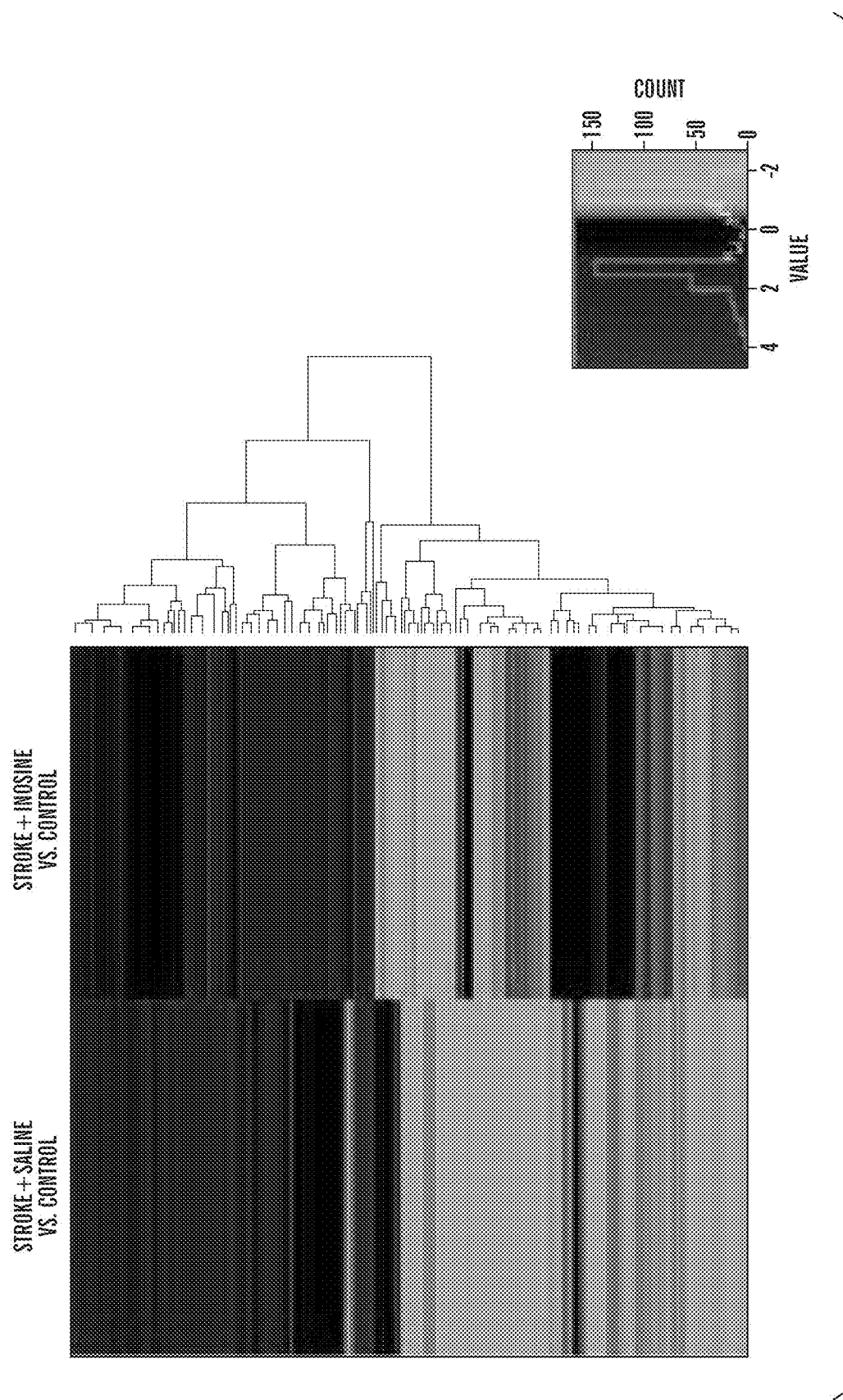
FIG. 14A-FIG. 14D show that inosine alters gene expression in corticospinal neurons contralateral to the stroke.
Figure 14B:
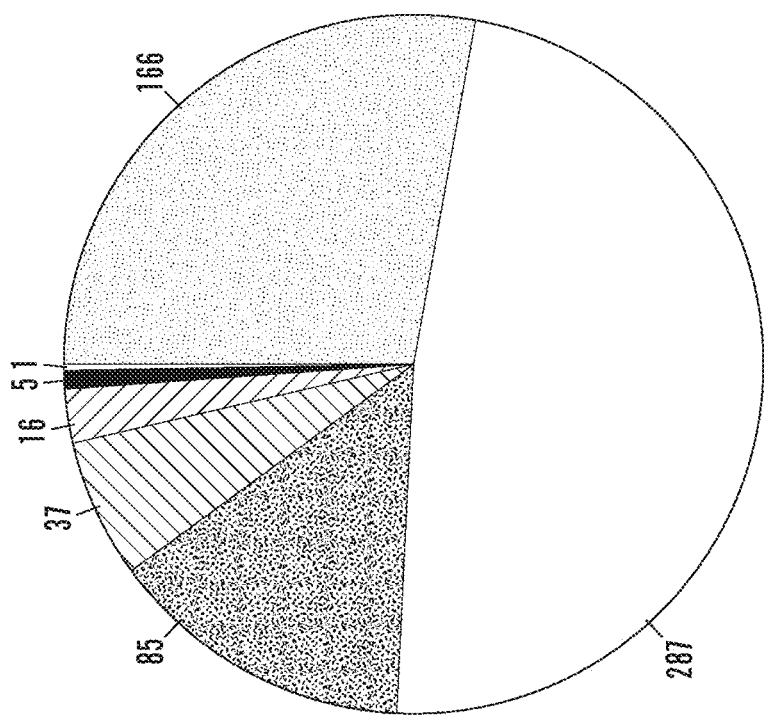
Figure 14D:
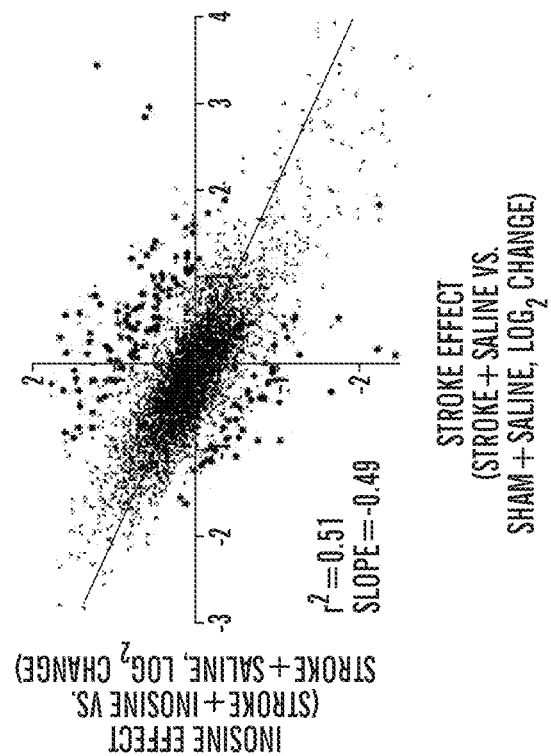

To investigate the effects of inosine at a molecular level, we used laser-capture microdissection (LCM) to isolate corticospinal tract neurons (CSNs) on the side of the brain contralateral to the stroke 7 days after surgery and treatment. mRNA from each animal was analyzed separately using Illumina microarrays. Resulting signal intensities ranged from <100 to >30,000 and showed good reproducibility, with R values (Pearson's correlation) varying from 0.93 to 0.98 between biological replicates. Of the ca. 22,000 genes represented on the arrays, stroke and/or inosine treatment caused significant changes in the expression of 636 genes using the following criteria: (a) average signal intensity ≥400 in at least one condition and (b) change significant at P≤0.01 (Table 4). 84% of these changes resulted from stroke per se (293 decreases in expression and 242 increases; FIG. 14A). Analysis of the stroke-induced changes using Ingenuity Pathways Analysis software revealed an over-representation of genes involved in protein ubiquitination ($P<10^{-3}$), mostly a down-regulation of particular ubiquitination factors (ube4A, ube2M, ube2E3), proteosomal proteins (psmC5, psmB5, psmB4, psmA7, hspA8), and heat shock protein (hsp)-70; genes encoding proteosomal proteins psmB6 and -8 showed increased expression. Also over-represented were genes associated with mitochondrial dysfunction. Stroke caused a significant upregulation of several components of the complement cascade (c1qβ, c1qγ, c2, c3).

Inosine showed two distinct effects: it attenuated most of the stroke-induced changes and induced the expression of a distinct set of genes (FIG. 14A-D). The effect of inosine in attenuating stroke-induced changes can be seen in the "heat map" of FIG. 14A, where the intensity of many of the changes induced by stroke (stroke/saline vs. control) is diminished by inosine treatment. This effect can also be visualized in the scatter plot of FIG. 14B. For each gene that is significantly affected by stroke (P<0.01), the magnitude of the change due to stroke was plotted along the x-axis ($\log_2$ ratio of expression in animals with stroke treated with saline vs. normal controls) and the magnitude of the change due to inosine on the y-axis ($\log_2$ ratio of expression in inosine- vs. saline-treated cases after stroke). The majority of points cluster around a trend line with a slope of −0.49 and an R value of 0.87 (P<0.0001), indicating that inosine strongly attenuates the changes due to stroke: a slope of −1 would signify that inosine fully restores changes due to stroke to baseline, whereas a more shallow slope or more scatter would indicate a lesser effect of inosine in attenuating the effects of stroke.

Figure 14C:
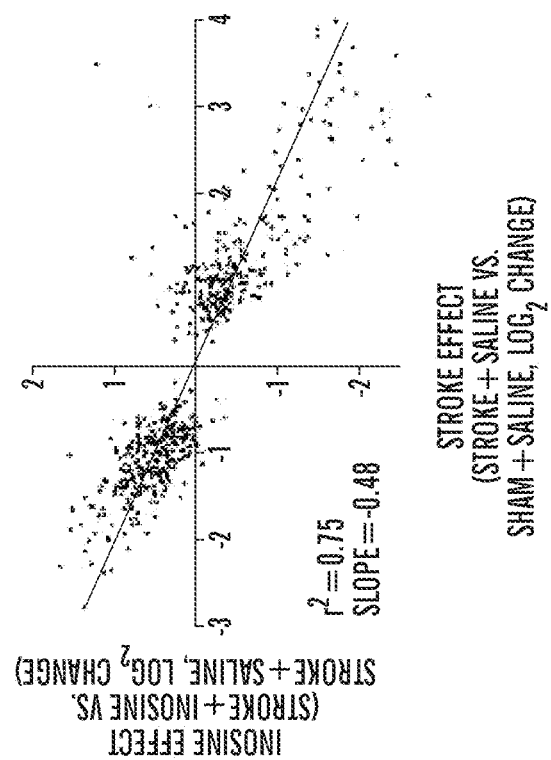

The second effect of inosine is represented by the genes that lie at a significant distance from the trend line through the data (FIG. 14C). The magnitude of this second effect was calculated as the difference between the observed value for the inosine:saline ratio after stroke and the expected value along the trend line of FIG. 14C. Of the genes that were significantly upregulated by inosine over and above attenuating the effect of stroke, 30% were also found to be upregulated in retinal ganglion cells stimulated to re-generate their axons in the mature rat optic nerve (Fischer et al., 2004b). This amount of overlap is significant at $P<10^{-7}$. Growth-related genes selectively upregulated by inosine include those encoding tissue inhibitor of metalloproteinase (timp1), metallothinonine, and galectin 3 (Table 2), though not others that are associated with optic nerve regeneration, e.g., gap43 and sprr1 a. The other striking effect of inosine was to increase expression of proteins in the complement cascade, including c1qa, c1qb, c1qg, c1s, c2, c3, c4B, adipsin, serping1, and cfb (complement factor B) (Table 3). This set of changes is highly significant ($P<10^{-11}$).

To verify that the between-group differences seen in gene expression were not due to differences in mRNA degradation, RNA stability was examined using several methods. Mean detection scores, a measure of the genes that were detected in the various samples, did not differ among unoperated controls (Table 5), animals with strokes treated with inosine, and animals with strokes treated with saline. These groups also did not differ when we compared average fragment lengths in doubly-amplified RNA samples, as analyzed by Agilent Bioanlyzer Nanochips. A subset of samples were also run on both Illumina and Affymetrix arrays, and computed the 5' to 3' ratio, finding comparable ratios in all sets.

To investigate whether some of the changes seen in the microarray study translate into differences at the protein level, immunohistochemistry was performed for C1q, C3, and metallothionein (Study VII). Quantitation of complement staining intensities and counts of metallothionein-positive profiles showed that the inosine-induced changes seen in the microarrays data are also evident at the protein level. Immunohistochemistry was used to investigate whether inosine-induced changes found at the mRNA level translate into changes at the protein level. Analyses were carried out in layer 5 of the uninjured forelimb motor cortex 7 days after a stroke was induced in the corresponding region of the contralateral hemisphere. Inosine induced changes in levels of complement proteins C1q (a) and C3 (b) and metallothionine (c).

For C1q, inosine increased staining intensity by 75% in layer 5 of the undamaged hemisphere (average grain pixel density=3231±519 for saline-treated cases and 5654±894 for inosine-treated cases: difference significant at P<0.05). For C3, inosine increased staining intensity by 37% (average grain pixel density=1002±101 for saline-treated cases and 1377±101 for inosine: difference significant at P<0.05). Finally, for metallothionine, inosine increased the number of positively staining profiles per field by 28% (14.0±1.5 for saline-treated animals and 17.9±0.8 for inosine-treated cases).

Inosine Enhances the Effect of the NEP1-40 Peptide.

Figure 17A:
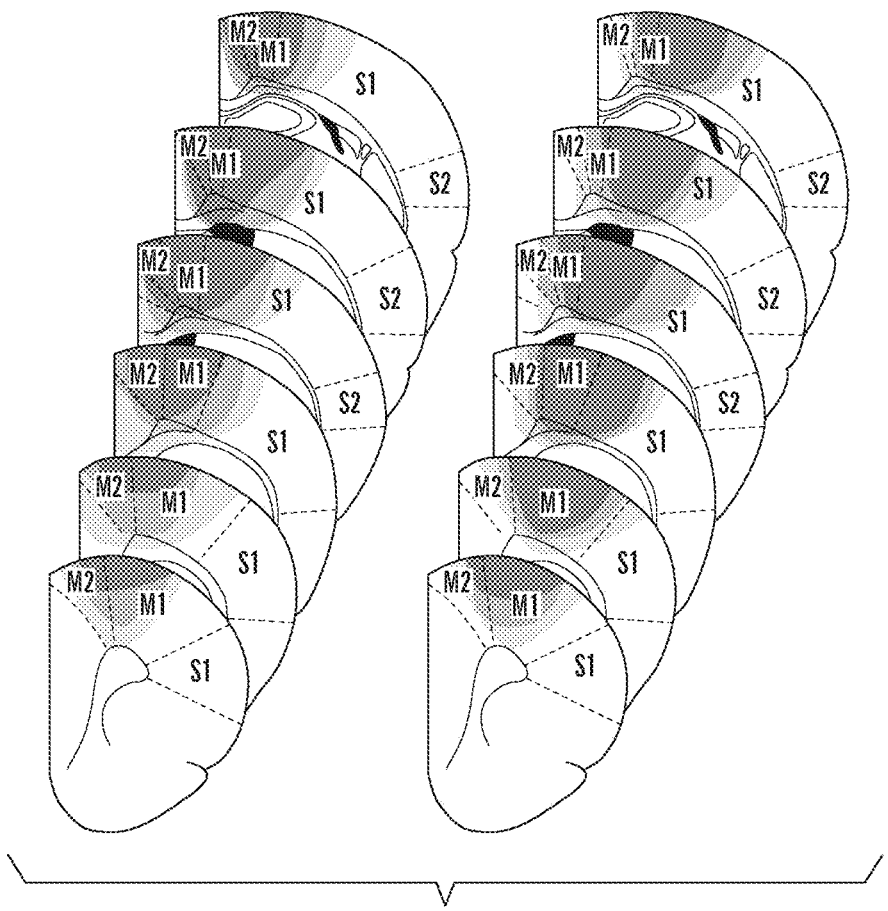
FIG. 17A-FIG. 17B shows the extent and size of lesions in animals receiving combinatorial treatment.
Figure 17B:
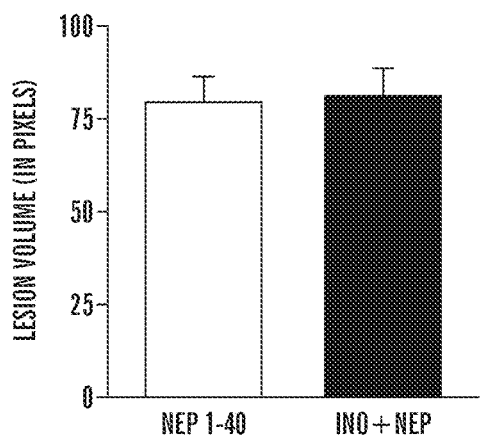

NEP1-40, a peptide antagonist of the Nogo receptor, partially abrogates the effect of myelin on growth cone collapse and promotes CST axon growth in vivo (GrandPre et al., 2002). Whether the effect of NEP1-40 on CST plasticity could be enhanced by inosine was investigated. As expected, neither NEP1-40 by itself nor NEP1-40 combined with inosine was neuroprotective, as assessed by measuring stroke volume (FIG. 17). NEP1-40 increased the number of CST fibers that originate in the undamaged hemisphere, enter the denervated dorsal funiculus (FIG. 18A, E, P<0.05), and project into the cervical grey matter (FIG. 18F,G). This effect was observed for total axons >40 μm in length in the transverse plane (P<0.05) and for longer fibers (>200 μm, P<0.01).

Figure 18A:
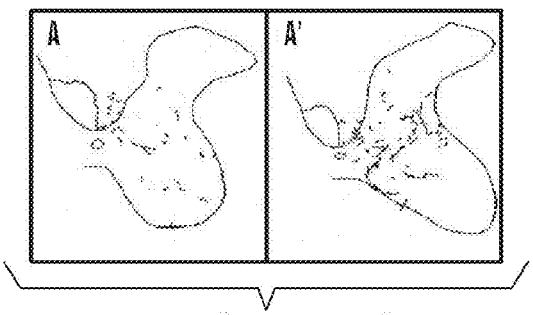
FIG. 18A-FIG. 18G show NEP1-40 enhances the effects of inosine on CST rewiring.
Figure 18B:
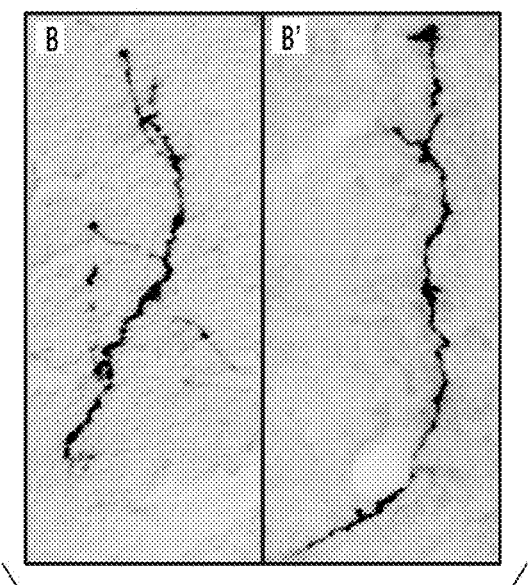
Figure 18C:
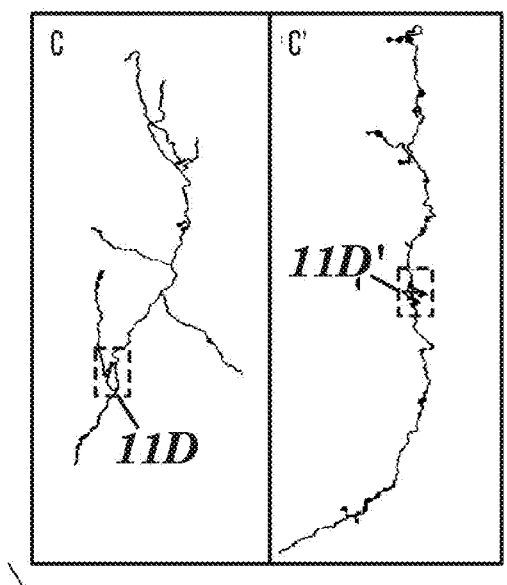
Figure 18D:
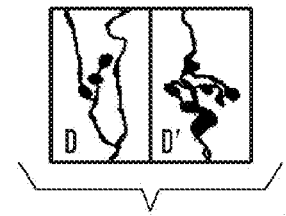
Figure 18E:
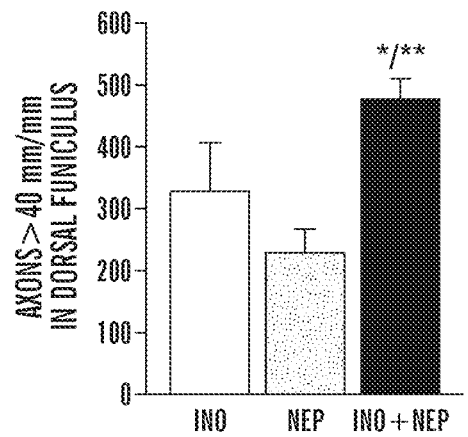
Figure 18F:
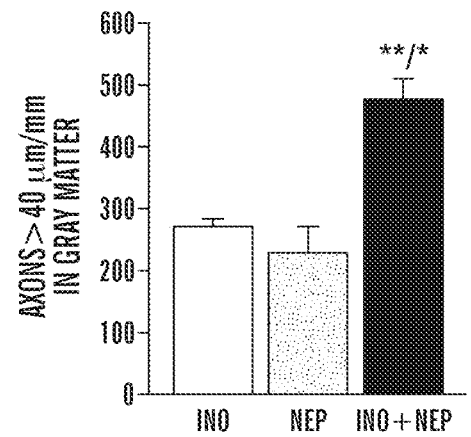
Figure 18G:
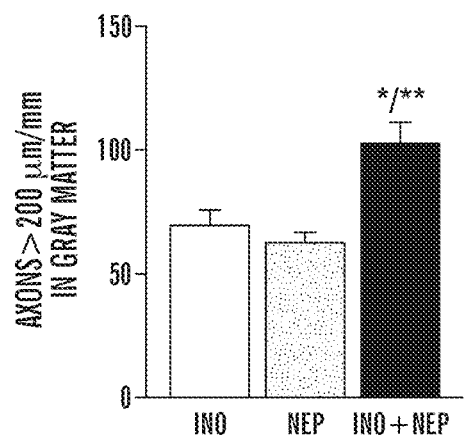

Inosine enhanced the effect of NEP1-40 on CST reorganization (FIG. 11A' and FIG. 18A'). Inosine strongly increased the number of axons >40 μm in length (FIG. 18F, P<0.01) and >200 μm in length (FIG. 18G, P<0.01) in the cervical gray matter relative to the levels seen with NEP1-40 alone (FIG. 18E), though it did not increase the number of CST fibers seen in the denervated dorsal funiculus.

Figure 19A:
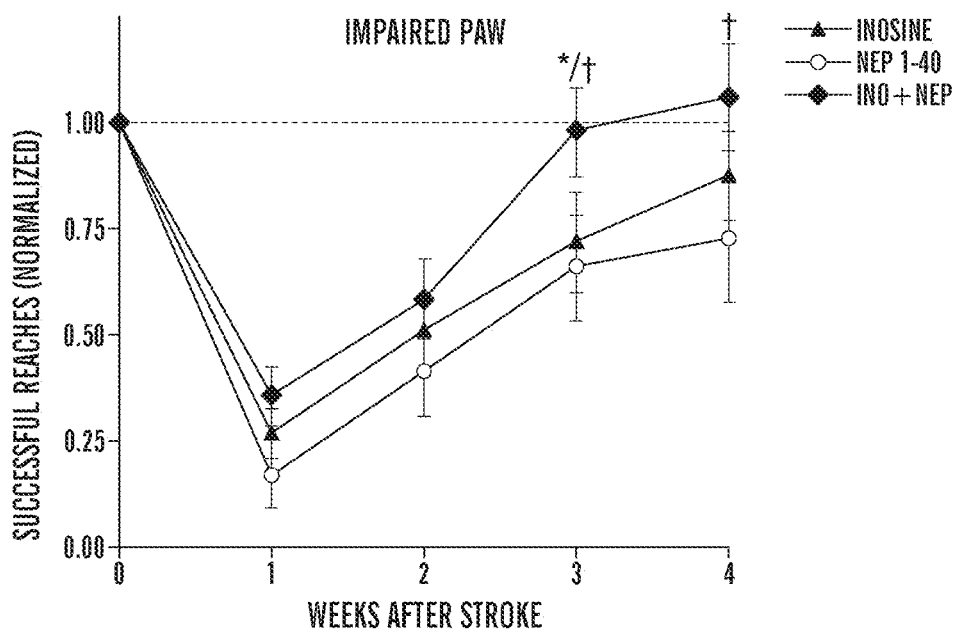
FIG. 19A-FIG. 19B show inosine combined with NEP1-40 restores food-retrieval skill with the affected paw to pre-operative levels. Animals were trained in the food-retrieval task, tested, and scored as in FIG. 12.
Figure 19B:
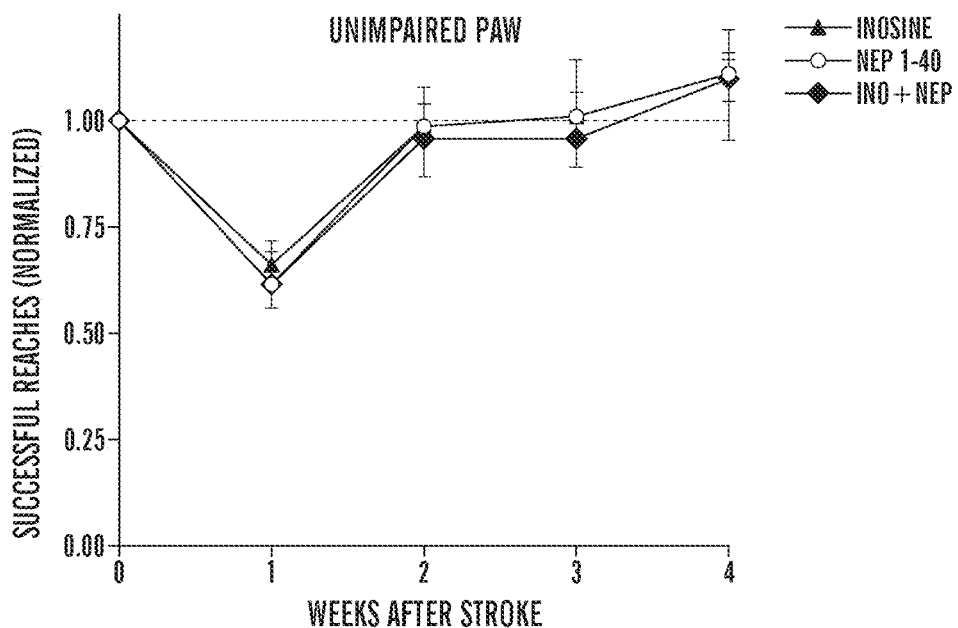

Combinatorial treatment enhanced skilled use of the denervated forepaw. Treatment with NEP1-40 alone enabled animals to perform better than saline-treated controls by 3 weeks after injury (FIG. 19A, P<0.05) and this difference persisted at week 4. Animals treated with the combination of inosine and NEP1-40 performed better than saline-treated controls as early as one week after surgery (FIG. 19A, P<0.01), and by three weeks, they also performed significantly better than animals receiving NEP 1-40 alone (FIG. 19A, P<0.05). Remarkably, by 4 weeks, animals receiving combinatorial treatment were able to retrieve food pellets with the impaired paw as well as they had pre-operatively. No inter-group differences were seen in the use of the paw ipsilateral to the injury. In preliminary studies, a scrambled NEP1-40 control peptide improved behavior as well as NEP1-40 (data not shown).

Long-Term Effects of Treatment on Functional Recovery

Figure 20A:
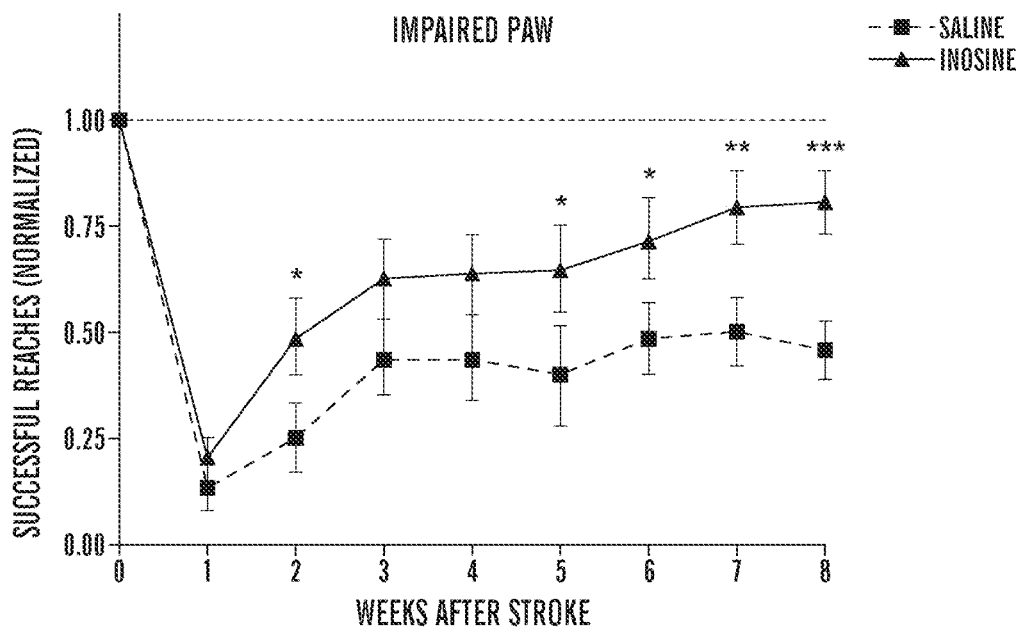
FIG. 20A-FIG. 20D shows functional improvements persist after cessation of treatment. Long-term studies were carried out in animals treated with inosine alone (FIGS. 20A and B) or combined with NEP1-40 (FIGS. 20 C and D) for 4 weeks after treatments ended, i.e., 8 weeks after stroke. Animals were tested with either the affected paw contralateral to the stroke (FIGS. 20 A and C) or the unaffected paw (FIGS. 20B and D). Performance with the affected paw failed to improve for saline-treated animals after 3-4 weeks, but remained high, or even continued to improve, in animals receiving inosine alone (FIG. 20A) or inosine combined with NEP1-40 (FIG. 20C). Performance with the combined therapy remained above that from single treatments and improved above pre-operative levels at later time points.
Figure 20B:
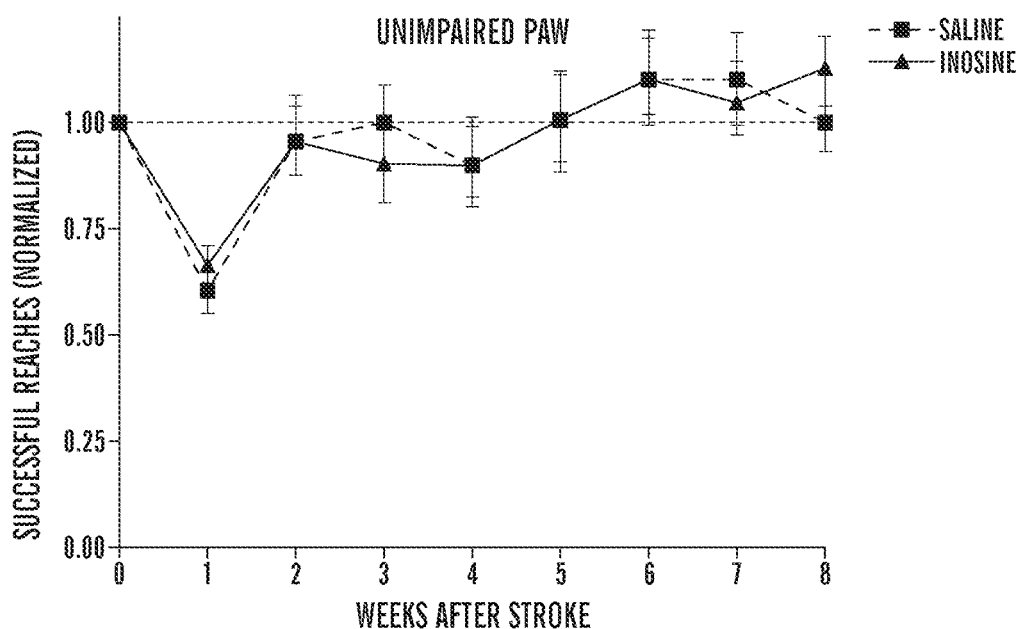
Figure 20C:
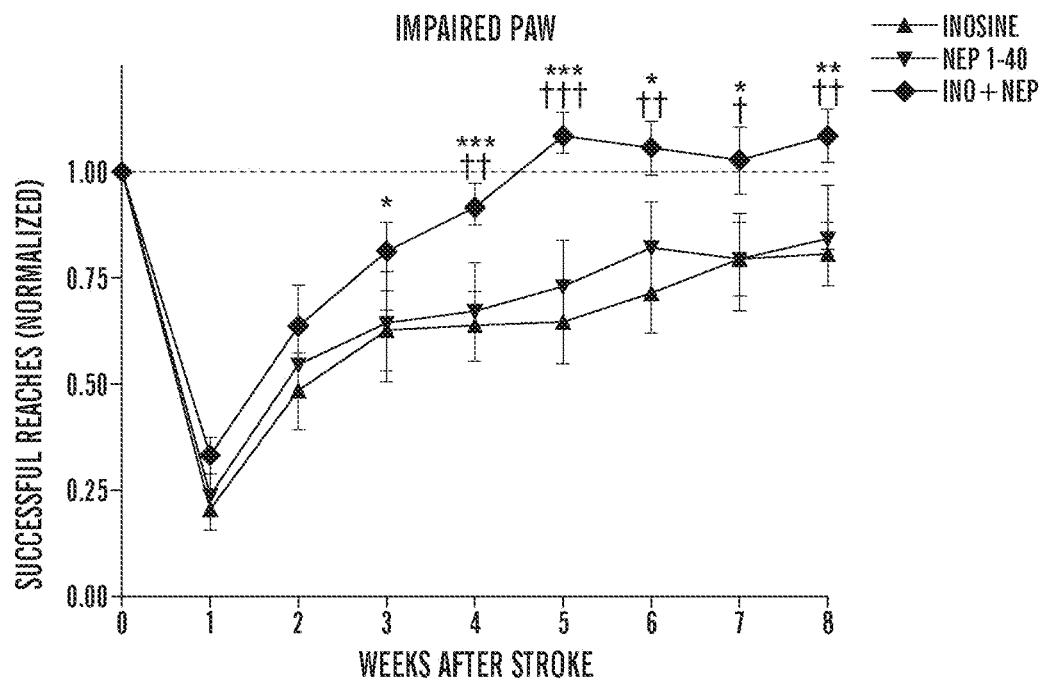
Figure 20D:
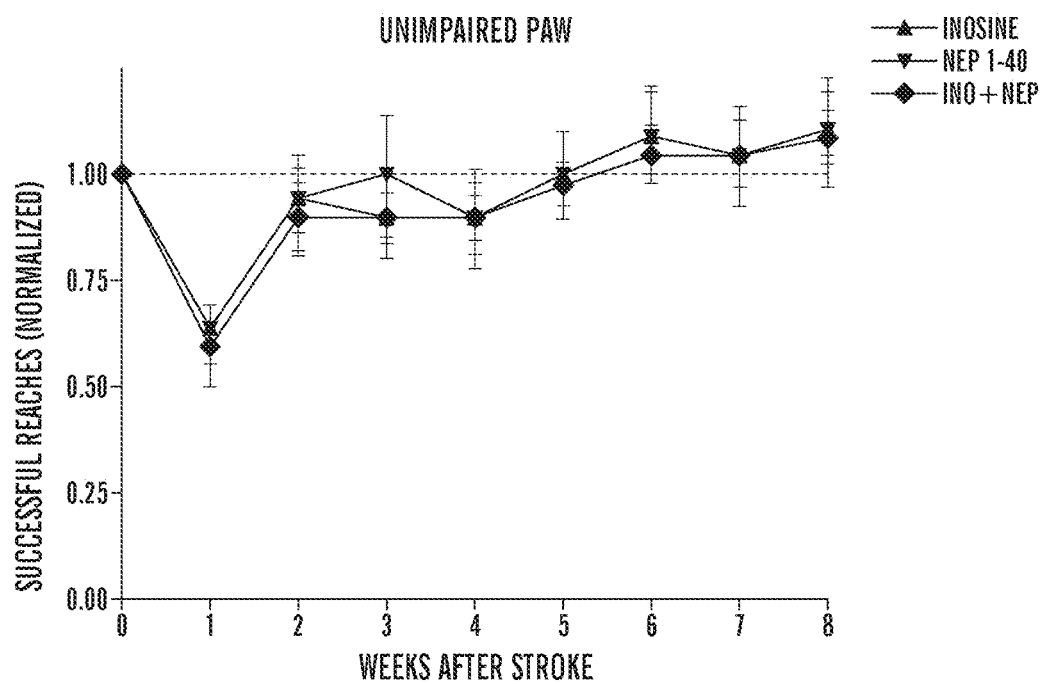

To determine if the functional benefits of inosine and/or NEP1-40 persist after treatment ends, separate groups of animals were generated for an eight-week behavioral study. Animals were treated and tested for 4 weeks after stroke as before, but were tested for an additional 4 weeks after minipumps were removed. Saline-treated animals again performed at around 40% of their preoperative level by week 3-4, and no further improvements were seen at later time points (FIG. 20A). In contrast, inosine-treated animals continued to improve over time, going from ~70% of baseline at week four to ~80% at week eight. The performance of inosine-treated animals in this series was significantly better than that of saline-treated controls from week 2 on (P<0.05 for weeks 2-6, P<0.01 for weeks 7 and 8). NEP 1-40 treatment likewise improved performance relative to saline-treated controls (FIG. 20C, P<0.05 at weeks 2-4 and 7, P<0.01 at weeks 5, 6 and 8). Inosine strongly enhanced the effect of NEP1-40 (FIG. 20C, P<0.01 from week 4 onwards). The combined-treatment group continued to improve between weeks four and eight, achieving behavioral scores that were consistently above those of the other experimental groups (FIG. 8c). The results of this study fully confirm the effects of inosine seen in the animals treated for 4 weeks described above, and show that the benefits of these treatments persist after pumps are removed. Remarkably, with further testing and training, animals treated with inosine and NEP1-40 were able to retrieve and consume food pellets at least as well as when the contralateral SMA was intact (FIG. 20C).

Discussion

Following a unilateral stroke, intraventricular delivery of inosine altered gene expression in corticospinal motorneurons (CSMNs) of the undamaged hemisphere, stimulated these cells to form new connections on the denervated side of the spinal cord, and improved animals' ability to use the impaired forelimb in a skilled tactile retrieval task. In the absence of inosine, photothrombotic injury to the sensorimotor area (SMA) of one hemisphere altered the transcriptional profile of CSMNs on the undamaged side of the brain. Inosine attenuated these changes, induced the expression of genes related to axon growth and synaptic remodeling, and stimulated the growth of new connections into the denervated side of the spinal cord. When inosine was combined with a Nogo receptor antagonist, animals' ability to retrieve food pellets with the impaired forepaw returned to preoperative levels.

Mechanisms of Action

Inosine induces several types of neurons to extend axons in culture, including those of the embryonic cortex (Zurn and Do, 1988; Benowitz et al., 1998; Irwin et al., 2006). Inosine diffuses across the cell membrane and activates Mst3b, a Ste20-like protein kinase that plays a central role in the signal transduction pathway through which trophic factors induce axon outgrowth. Knock-down of Mst3b expression or expression of a dominant-negative form of Mst3b abrogates the axon-promoting effects of inosine and trophic factors (Irwin et al., 2006; Lorber et al., 2008).

Other known effects of inosine may also contribute to improving outcome after stroke. Inosine has been reported to limit the size of a cortical infarct when administered prior to stroke, though not afterwards (Shen et al., 2005), and to be neuroprotective after spinal cord injury (Liu et al., 2006b). Inosine did not show obvious neuroprotective effects in the present study, as judged by the absence of changes in lesion size or in caspase-3 activation. Inosine has also been reported to suppress the response of cortical neurons to glutamate (Shen et al., 2005), enhance inhibition by binding to benzodiazepine receptors (Marangos et al., 1981), limit the production of inflammatory cytokines (Hasko et al., 2000, 2004) and, at high concentrations, block hypoxia-induced astrocyte death (Haun et al., 1996; Jurkowitz et al., 1998). In addition, uric acid, a primary metabolite of inosine, prevents peroxynitrite-induced protein damage, protects the blood-brain barrier, and has potent anti-inflammatory effects (Scott et al., 2002, 2005). The extent to which these effects contributed to improving functional outcome in the present study is unknown.

Gene Expression

Transcriptional profiling of CSN-enriched preparations revealed that inosine affects gene expression in cells contralateral to a stroke in two ways. Inosine attenuated the many changes in gene expression induced by the stroke, while also upregulating the expression of genes related to axon growth and synaptic remodeling. The basis for the stroke-induced changes in untreated animals is unknown, but could be due to the loss of synaptic inputs from the injured side, hyperexcitability, inflammation, or hypoxia. Gene ontogeny analysis indicates that some of the stroke-induced genes are related to mitochondrial dysfunction and proteosomal processing. The ability of inosine to attenuate these changes was unanticipated, but could be related to its neuroprotective or anti-inflammatory properties. In addition to this effect, inosine increased the expression of many of the same genes that are upregulated in retinal ganglion cells undergoing axon regeneration in vivo (Fischer et al., 2004b). However, inosine did not increase the expression of such well-established growth-associated proteins as GAP43 and SPRR1A, perhaps reflecting differences in the molecular programs associated with collateral sprouting from undamaged neurons vs. lengthy regeneration of injured axons.

In light of recent studies linking complement proteins to synaptic remodeling (Stevens et al., 2007), the upregulation of these proteins by inosine may be contributing to structural reorganization in the present study. Although complement proteins have been detected in mature cortical pyramidal cells (Shen et al., 1997), their upregulation in our studies could have occurred in other cells included inadvertently in our LCM samples, e.g., microglia.

Anatomical Reorganization

In adult rats, almost all CST axons decussate in the pyramids and project to the contralateral side of the spinal cord. Even in the absence of treatment, unilateral damage to the forelimb motor area significantly increased the number of CST fibers that projected from the undamaged hemisphere into the denervated side of the spinal cord. This finding is consistent with prior reports of axonal reorganization in other brain regions after stroke (Carmichael et al., 2001, 2005; Dancause et al., 2005) and other types of CNS injury (Raisman, 1969; Lynch et al., 1976; Darian-Smith and Gilbert, 1994; Buonomano and Merzenich, 1998; Z'Graggen et al., 2000; Weidner et al., 2001; Bareyre et al., 2004). Thus, the effect of inosine in enhancing CST reorganization appears to represent an augmentation of the brain's normally modest capacity to rewire itself after injury. The results of the present study show that inosine particularly promotes the extension of long axon branches into the denervated gray matter of the spinal cord and the formation of bouton-like structures that are likely to correspond to synapses (Lagerback et al., 1981; Havton and Kellerth, 1987). The trajectory by which axons from the undamaged hemisphere reach the undamaged, ipsilateral side of the spinal cord is not entirely clear. Inosine did not promote CST reorganization in the absence of brain injury. These observations suggest that target denervation and/or novel patterns of brain activity seen after stroke (Carmichael, 2006) are prerequisites for neurons exposed to inosine to form new connections. Another point worth noting is that, although recent studies indicate that smaller lesions are less likely to induce dramatic anatomical reorganization than larger ones (Nudo, 2006), inosine was found here to increase axon growth even after relatively small lesions limited to the forelimb motor area and surrounding cortex. Although the lesions of the present study included most of the classical forelimb area, a more rostral area that may be important for control of the digits (Neafsey and Sievert, 1982) was not included. Hence, the recovery seen here may involve contributions from both the forelimb area of the uninjured hemisphere and spared regions of the damaged hemisphere, including perhaps the rostral forelimb area.

Behavioral Outcome

Inosine enabled rats to retrieve food pellets with the impaired paw to approximately 80% of the level seen before surgery. This task involves precise, coordinated movements of the limbs, forepaw and digits, and requires the integrity of the contralateral sensorimotor cortex for its acquisition and execution (Whishaw et al., 1993). In the absence of inosine, rats' ability to use the affected forepaw reached a plateau of 35-40% of the pre-operative level of performance 3-4 weeks after stroke. Although both the spontaneous improvements and the effect of inosine in enhancing performance correlated with changes in CST organization, it is possible that the functional improvements seen here involved additional anatomical changes in both hemispheres and perhaps even other effects of inosine or uric acid, e.g., limiting neural excitability, inflammation, blood-brain barrier permeability, and protein damage. Whether inosine augments the changes in dendritic growth and neurogenesis that occur after stroke (Jones, 1999; Bury and Jones, 2002; Carmichael, 2006) remains unknown.

CST reorganization was not yet evident 2 weeks after inosine treatment. This could reflect a delay in the initiation of axon reorganization or a technical difficulty in detecting thin, nascent axons that might have been present. If CST axons arising from the ipsilateral hemisphere were not yet present at 2 weeks, the behavioral improvements seen at that time point may have been due to the sprouting of CST fibers arising from undamaged layer 5 pyramidal cells in the same hemisphere as the stroke, as suggested above, or to the reorganization of other pathways not studied here, or to some of the other effects of inosine suggested above.

In our prior study, rats sustained large vascular strokes in the territory of the middle cerebral artery and part of the anterior cerebral artery. This caused extensive damage to the basal ganglia and lateral cortex, and impaired extrapyramidal motor pathways and sensorimotor integration, while sparing much of the primary forelimb motor area (Chen et al., 2002). Although inosine enabled rats in that study to swipe for food pellets with the affected paw, almost none of the animals could grasp the pellets and consume them. Thus, that study left open the question of whether inosine could promote the formation of circuitry that could restore complex behaviors mediated by a specific brain area, i.e., the forepaw motor area. The differences in outcome between the prior study and this one are likely to be related primarily to differences in the extent and locus of damage. Another potentially relevant difference is that animals in the present study received a bolus injection of inosine immediately after stroke, supplementing the slow build-up in the CSF that would be expected from minipump delivery.

Combinatorial Therapy

In the optic nerve, activation of neurons' intrinsic growth state strongly enhances the amount of axon regeneration that results from counteracting cell-extrinsic inhibitory signals (Fischer et al., 2004a; Fischer et al., 2004b). Whether inosine would augment the effects of NEP1-40, a peptide that blocks inhibitory signals transmitted through the Nogo receptor (NgR), was investigated. NgR mediates some of the inhibitory effects of NogoA, MAG, and OMgp on axon growth, and blockade of NgR signaling or deletion of the ngr gene enhances axonal rewiring after stroke (Lee et al., 2004). The NEP1-40 peptide has been shown to promote axon growth after spinal cord injury and improve behavioral outcome (Li and Strittmatter, 2003; Cao et al., 2007), although others have reported lesser effects that are also seen with a scrambled control peptide (Steward et al., 2008). In our studies, NEP1-40 by itself enhanced axon rewiring and functional improvement with the impaired paw. Inosine strongly augmented the effects of NEP1-40 in both CST rewiring and skilled use of the affected forepaw. Unlike controls, all treated groups continued to improve despite the cessation of treatment at 4 weeks, presumably using compensatory circuitry and behavioral strategies. Remarkably, animals receiving combinatorial treatment performed better than their preoperative levels from 4 weeks onwards.

Summary and Conclusions

Inosine alters gene expression in neurons contralateral to a stroke and enables them to form connections on the side of the spinal cord which had lost its normal innervation. When inosine was delivered together with a peptide antagonist of the Nogo receptor, animals returned to preoperative levels of performance in a skilled food-reaching task using the affected paw. This dramatic recovery is likely to be related to other anatomical changes in addition to the ones visualized here and perhaps also to the anti-inflammatory and neuroprotective effects of inosine and its metabolite, uric acid.

In view of the established safety of inosine in other clinical settings, these results indicate inosine administration, and administration of inosine with an antagonist of Nogo receptor, has therapeutic applications after stroke and other types of neurological damage.

References for Example III

1. Allred R P, Jones T A (2004) Unilateral ischemic sensorimotor cortical damage in female rats: forelimb behavioral effects and dendritic structural plasticity in the contralateral homotopic cortex. Exp Neurol 190:433-445.
2. Bareyre F M, Kerschensteiner M, Raineteau O, Mettenleiter T C, Weinmann O, Schwab M E (2004) The injured spinal cord spontaneously forms a new intraspinal circuit in adult rats. Nat Neurosci 7:269-277.
3. Benowitz L I, Jing Y, Tabibiazar R, Jo S A, Petrausch B, Stuermer C A, Rosenberg P A, Irwin N (1998) Axon outgrowth is regulated by an intracellular purine-sensitive mechanism in retinal ganglion cells. J Biol Chem 273: 29626-29634.
4. Buonomano D V, Merzenich M M (1998) Cortical plasticity: from synapses to maps. Annu Rev Neurosci 21:149-186.

5. Bury S D, Jones T A (2002) Unilateral sensorimotor cortex lesions in adult rats facilitate motor skill learning with the "unaffected" forelimb and training-induced dendritic structural plasticity in the motor cortex. J Neurosci 22:8597-8606.
6. Cafferty W B, Strittmatter S M (2006) The Nogo-Nogo receptor pathway limits a spectrum of adult CNS axonal growth. J Neurosci 26:12242-12250.
7. Cao Y, Shumsky J S, Sabol M A, Kushner R A, Strittmatter S, Hamers F P, Lee D H, Rabacchi S A, Murray M (2007) Nogo-66 Receptor Antagonist Peptide (NEP1-40) Administration Promotes Functional Recovery and Axonal Growth After Lateral Funiculus Injury in the Adult Rat. Neu-rorehabil Neural Repair.
8. Carmichael S T (2003) Plasticity of cortical projections after stroke. Neuroscientist 9:64-75.
9. Carmichael S T (2006) Cellular and molecular mechanisms of neural repair after stroke: making waves. Ann Neurol 59:735-742.
10. Carmichael S T, Wei L, Rovainen C M, Woolsey T A (2001) New patterns of intracortical projections after focal cortical stroke. Neurobiol Dis 8:910-922.
11. Carmichael S T, Archibeque I, Luke L, Nolan T, Momiy J, Li S (2005) Growth-associated gene expression after stroke: evidence for a growth-promoting region in peri-infarct cortex. Exp Neurol 193:291-311.
12. Chen S, Aston-Jones G (1995) Evidence that cholera toxin B subunit (CTb) can be avidly taken up and transported by fibers of passage. Brain Res. 13:107-111.
13. Chen P, Goldberg D E, Kolb B, Lanser M, Benowitz L I (2002) Inosine induces axonal rewiring and improves behavioral outcome after stroke. Proc Natl Acad Sci USA 99:9031-9036.
14. Dancause N, Barbay S, Frost S B, Plautz E J, Chen D, Zoubina E V, Stowe A M, Nudo R J (2005) Extensive cortical rewiring after brain injury. J Neurosci 25:10167-10179.
15. Darian-Smith C, Gilbert C D (1994) Axonal sprouting accompanies functional reorganization in adult cat striate cortex. Nature 368:737-740.
16. Dobkin B (2003) The Clincal Science of Neurologic Rehabilitation, Second Edition. Oxford: Oxford University Press.
17. Emerick A J, Neafsey E J, Schwab M E, Kartje G L (2003) Functional reorganization of the motor cortex in adult rats after cortical lesion and treatment with monoclonal antibody IN-1. J Neurosci 23:4826-4830.
18. Filbin M T (2003) Myelin-associated inhibitors of axonal regeneration in the adult mammalian CNS. Nat Rev Neurosci 4:703-713.
19. Fischer D, He Z, Benowitz L I (2004a) Counteracting the Nogo receptor enhances optic nerve regeneration if retinal ganglion cells are in an active growth state. J Neurosci 24:1646-1651.
20. Fischer D, Petkova V, Thanos S, Benowitz L I (2004b) Switching mature retinal ganglion cells to a robust growth state in vivo: gene expression and synergy with RhoA inactivation. J Neurosci 24:8726-8740.
21. Gentleman R, Carey V, Bates B, Bolstad B, Dettling M, Dudoit S, Ellis B, Gautier L, Ge Y, Gentry J, Hornik K, Hothorn T, Huber W, Iacus S, Irizarry R, Leisch F, Li C, Maechler M, Rossini A, Sawitzki G, Smith G, Smyth G, Tierney L, Yang J, Zhang J (2004) Bioconductor: open software development for computational biology and bioinformatics. In: Genome Biol pR80.
22. GrandPre T, Li S, Strittmatter S M (2002) Nogo-66 receptor antagonist peptide promotes axonal regeneration. Nature 417:547-551.
23. Hasko G, Sitkovsky M V, Szabo C (2004) Immunomodulatory and neuroprotective effects of inosine. Trends Pharmacol Sci 25:152-157.
24. Hasko G, Kuhel D G, Nemeth Z H, Mabley J G, Stachlewitz R F, Virag L, Lohinai Z, Southan G J, Salzman A L, Szabo C (2000) Inosine inhibits inflammatory cytokine production by a post-transcriptional mechanism and protects against endotoxin-induced shock. J Immunol 164:1013-1019.
25. Haun S E, Segeleon J E, Trapp V L, Clotz M A, Horrocks L A (1996) Inosine mediates the protective effect of adenosine in rat astrocyte cultures subjected to combined glucose-oxygen deprivation. Journal of Neurochemistry 67:2051-2059.
26. Havton L, Kellerth J O (1987) Regeneration by supernumerary axons with synaptic terminals in spinal motoneurons of cats. Nature 325:711-714.
27. Hsu J E, Jones T A (2006) Contralesional neural plasticity and functional changes in the less-affected forelimb after large and small cortical infarcts in rats. Exp Neurol 201:479-494.
28. Irwin N, Li Y M, O'Toole J E, Benowitz L I (2006) Mst3b, a purine-sensitive Ste20-like protein kinase, regulates axon outgrowth. Proc Natl Acad Sci USA 103:18320-18325.
29. Jones T A (1999) Multiple synapse formation in the motor cortex opposite unilateral sensorimotor cortex lesions in adult rats. J Comp Neurol 414:57-66.
30. Jurkowitz M S, Litsky M L, Browning M J, Hohl C M (1998) Adenosine, inosine, and guanosine protect glial cells during glucose deprivation and mitochondrial inhibition: correlation between protection and ATP preservation. J Neurochem 71:535-548.
31. Kawamata T, Dietrich W D, Schallert T, Gotts J E, Cocke R R, Benowitz L I, Finklestein S P (1997) Intracisternal basic fibroblast growth factor enhances functional recovery and up-regulates the expression of a molecular marker of neuronal sprouting following focal cerebral infarction. Proc Natl Acad Sci USA 94:8179-8184.
32. Lagerback P A, Ronnevi L O, Cullheim S, Kellerth J O (1981) An ultrastructural study of the synaptic contacts of alpha-motoneurone axon collaterals. I. Contacts in lamina IX and with identified alpha-motoneurone dendrites in lamina VII. Brain Res 207:247-266.
33. Lee J K, Kim J E, Sivula M, Strittmatter S M (2004) Nogo receptor antagonism promotes stroke recovery by enhancing axonal plasticity. J Neurosci 24:6209-6217.
34. Li S, Strittmatter S M (2003) Delayed systemic Nogo-66 receptor antagonist promotes recovery from spinal cord injury. J Neurosci 23:4219-4227.
35. Liu B P, Cafferty W B, Budel S O, Strittmatter S M (2006a) Extracellular regulators of axonal growth in the adult central nervous system. Philos Trans R Soc Lond B Biol Sci 361:1593-1610.
36. Liu F, You S W, Yao L P, Liu H L, Jiao X Y, Shi M, Zhao Q B, Ju G (2006b) Secondary degeneration reduced by inosine after spinal cord injury in rats. Spinal Cord 44:421-426.
37. Lorber B, Howe M L, Benowitz L I, Irwin N (2008) Mst3b, an Ste20-like kinase, regulates axon regeneration in the mature CNS and PNS. (submitted).
38. Luke L M, Allred R P, Jones T A (2004) Unilateral ischemic sensorimotor cortical damage induces contrale- 39. Lynch G, Gall C, Rose G, Cotman C (1976) Changes in the distribution of the dentate gyrus associational system following unilateral or bilateral entorhinal lesions in the adult rat. Brain Res 110:57-71.
40. Marangos P J, Trams E, Clark-Rosenberg R L, Paul S M, Skolnick P (1981) Anticonvulsant doses of inosine result in brain levels sufficient to inhibit [3H] diazepam binding. Psychopharmacology (Berl) 75:175-178.
41. Markgraf C G, Kraydieh S, Prado R, Watson B D, Dietrich W D, Ginsberg M D (1993) Comparative histopathologic consequences of photothrombotic occlusion of the distal middle cerebral artery in Sprague-Dawley and Wistar rats. Stroke 24:286-292; discussion 292-283.
42. Neafsey E J, Sievert C (1982) A second forelimb motor area exists in rat frontal cortex. Brain Res. 232:151-156.
43. Nudo R J (2006) Mechanisms for recovery of motor function following cortical damage. Curr Opin Neurobiol 16:638-644.
44. Nudo R J (2007) Postinfarct cortical plasticity and behavioral recovery. Stroke 38:840-845.
45. Papadopoulos C M, Tsai S Y, Alsbiei T, O'Brien T E, Schwab M E, Kartje G L (2002) Functional recovery and neuroanatomical plasticity following middle cerebral artery occlusion and IN-1 antibody treatment in the adult rat. Ann Neurol 51:433-441.
46. Papadopoulos C M, Tsai S Y, Cheatwood J L, Bollnow M R, Kolb B E, Schwab M E, Kartje G L (2006) Dendritic plasticity in the adult rat following middle cerebral artery occlusion and Nogo-a neutralization. Cereb Cortex 16:529-536.
47. Paxinos G, Watson C (1998) The Rat Brain in Stereotaxic Coordinates, Fourth Ed. New York: Academic Press.
48. Raisman G (1969) Neuronal plasticity in the septal nuclei of the adult rat. Brain Res 14:25-48.
49. Scott G S, Cuzzocrea S, Genovese T, Koprowski H, Hooper D C (2005) Uric acid protects against secondary damage after spinal cord injury. Proc Natl Acad Sci USA 102:3483-3488.
50. Scott G S, Spitsin S V, Kean R B, Mikheeva T, Koprowski H, Hooper D C (2002) Therapeutic intervention in experimental allergic encephalomyelitis by administration of uric acid precursors. Proc Natl Acad Sci USA 99:16303-16308.
51. Shen H, Chen G J, Harvey B K, Bickford P C, Wang Y (2005) Inosine reduces ischemic brain injury in rats. Stroke 36:654-659.
52. Shen Y, Li R, McGeer E G, McGeer P L (1997) Neuronal expression of mRNAs for complement proteins of the classical pathway in Alzheimer brain. Brain Res 769:391-395.
53. Smith J M, Lunga P, Story D, Harris N, Le Belle J, James M F, Pickard J D, Fawcett J W (2007) Inosine promotes recovery of skilled motor function in a model of focal brain injury. Brain 130:915-925.
54. Smyth G K (2005) Limma: linear models for microarray data. In: Bioinformatics and Computational Biology Solutions using R and Bioconductor (R. Gentleman V C, S. Dudoit, R. Irizarry, W. Huber ed), pp 397-420. New York: Springer.
55. Stevens B, Allen N J, Vazquez L E, Howell G R, Christopherson K S, Nouri N, Micheva K D, Mehalow A K, Huberman A D, Stafford B, Sher A, Litke A M, Lambris J D, Smith S J, John S W, Banes B A (2007) The classical complement cascade mediates CNS synapse elimination. Cell 131:1164-1178.
56. Steward O, Sharp K, Yee K M, Hofstadter M (2008) A reassessment of the effects of a Nogo-66 receptor antagonist on regenerative growth of axons and locomotor recovery after spinal cord injury in mice. Exp Neurol 209:446-468.
57. Weidner N, Ner A, Salimi N, Tuszynski M H (2001) Spontaneous corticospinal axonal plasticity and functional recovery after adult central nervous system injury. Proc Natl Acad Sci USA 98:3513-3518.
58. Weiller C (1998) Imaging recovery from stroke. Exp Brain Res 123:13-17.
59. Whishaw I Q, Pellis S M, Gorny B, Kolb B, Tetzlaff W (1993) Proximal and distal impairments in rat forelimb use in reaching follow unilateral pyramidal tract lesions. Brain Research:59-76.
60. Z'Graggen W J, Fouad K, Raineteau O, Metz G A, Schwab M E, Kartje G L (2000) Compensatory sprouting and impulse rerouting after unilateral pyramidal tract lesion in neonatal rats. J Neurosci 20:6561-6569.
61. Zurn A, Do K (1988) Purine metabolite inosine is an adrenergic neurotrophic substance for cultured chicken sympathetic neurons. Proc Natl Acad Sci USA 85:8301-8305.

Example IV

Intravenous Administration of Inosine Improves Outcome after Spinal Cord Injury

Some degree of functional recovery often occurs after partial injuries to the spinal cord, reflecting in part the formation of new circuits that help restore function to spinal cord segments below the level of injury. One agent that is likely to augment this process and be suitable for clinical use is inosine. Inosine, a natural derivative of adenosine, is transported across the cell membrane, and at sufficient concentrations, inosine activates Mst3b, a protein kinase that plays a central role in the cell-signaling pathway that regulates axon growth. Inosine promotes axon sprouting and improves outcome after traumatic brain injury. Data presented herein further indicates that it also improves outcome after spinal cord injury. Following dorsal hemisections of the spinal cord that sever the corticospinal tract (CST), inosine-treated animals perform far better than controls on tests of sensorimotor integration and general locomotion. These improvements correlate with increased sprouting of serotonergic (raphespinal) projections distal to the injury site and CST axons rostral to this site, though not long-distance CST regeneration.

Figure 21A:
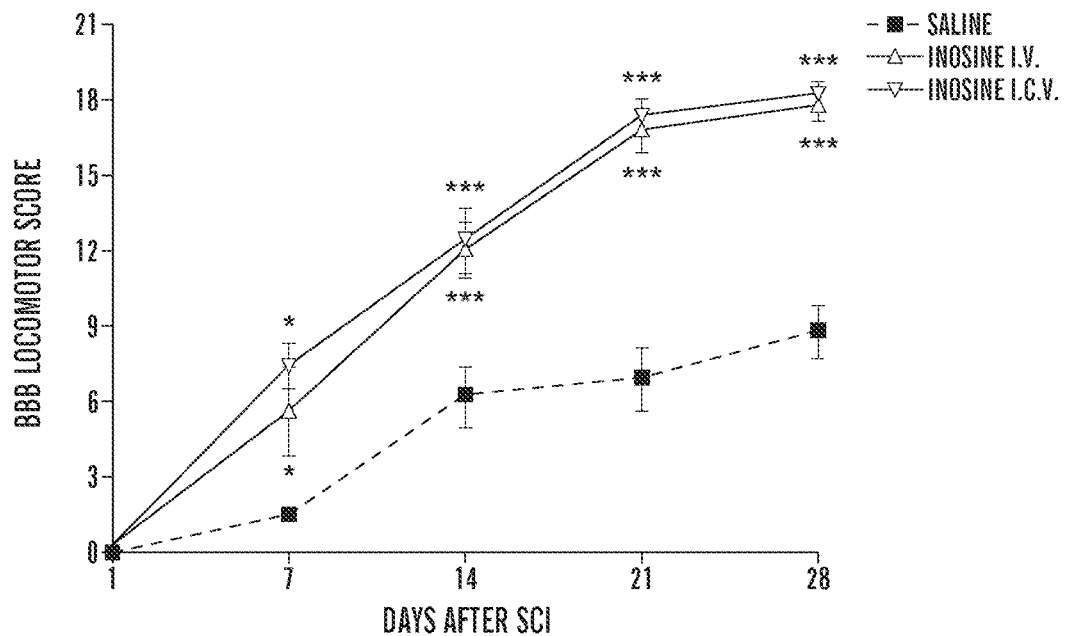
FIG. 21A-FIG. 21B are line graphs of data that show inosine improves behavioral outcome after spinal cord injury. Following transection of the dorsal half of the spinal cord, rats received either intra-cerebroventricular (i.c.v.) or intravenous (i.v.) infusions of inosine or saline for 4 weeks.
Figure 21B:
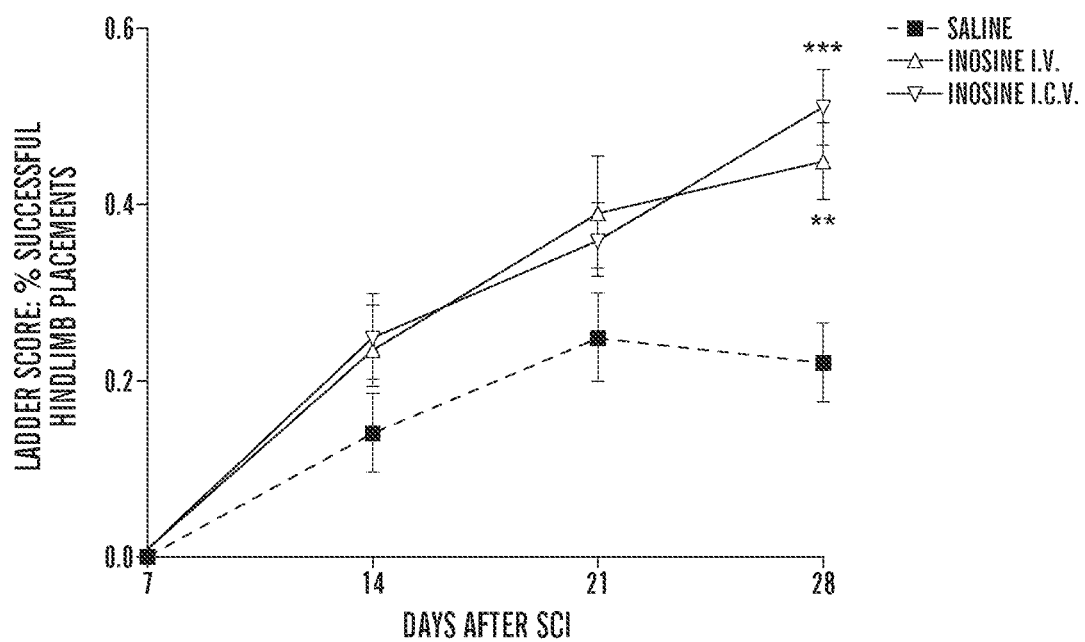

To test the effects of inosine on spinal cord injury, the dorsal half of the spinal cord in rats was transected, severing the descending CST and other pathways. CST loss severely disrupted fine, skilled behaviors. Inosine was then administered either intra-cerebroventricularly (50 mM, 0.25 μl/hour) or intravenously (260 mM, 10 μl/hour) for 4 weeks. In both cases, inosine enhanced performance on the Basso-Beatty-Bresnahan (BBB) test for general locomotor activity (FIG. 21A) and the horizontal ladder walk (FIG. 21B), a measure of sensorimotor integration that involves cortical mediation. Complete transection of the corticospinal tract was verified histologically. The effectiveness of inosine was clinically relevant, since it avoids the risk of intracerebral infection. Anatomically, administration of inosine enhanced the sprouting of raphespinal fibers distal to the injury site and corticospinal tract axons rostral to this site, and had modest effects on long-distance corticospinal tract regeneration.

Interestingly, both forms of administration produced dramatic results. These results indicate that both site specific and systemic administration of inosine, as well as other factors to promote neuronal regeneration (e.g., NgR antagonists), to a mammal with a central nervous system injury, promote the formation of new axon branches and produces therapeutic results.

TABLE 1

EXPERIMENTAL GROUPS

| Expt. | Animals per Group | Rationale | Survival Time | Analyses |
|---|---|---|---|---|
| I | 12 | Functional recovery, anatomical reorganization | 4 weeks | Behavioral testing, anatomical tracing |
| II | 6 | Effect of stroke alone | 4 weeks | anatomical tracing |
| III | 6 | Effect of inosine in the absence of brain injury | 4 weeks | anatomical tracing |
| IV | 12 | Persistence of recovery | 8 weeks | Behavioral testing |
| V | 6 | Short-term reorganization | 2 weeks | anatomical tracing |
| VI | 4-6 | Changes in gene expression | 1 week | Laser-capture microdissection, microarrays |
| VII | 4-8 | Changes in protein levels | 1 week | Immunohistochemistry, quantitative analysis |

TABLE 2

Genes that are upregulated by inosine in CSNs contralateral to cortical injury and in retinal ganglion cells undergoing axon regeneration in vivo

| | | | Fold-induction | |
|---|---|---|---|---|
| Probe | Symbol | Definition | CSMNs[1] | RGCs[2] |
| ILMN_53325 | LOC498335 | (P) Small inducible cytokine B13 precursor (CXCL13) | 11.42 | 3.97 |
| ILMN_70335 | A2m | α-2-macroglobulin | 4.10 | 2.36 |
| ILMN_62559 | Timp1 | tissue inhibitor of metalloproteinase 1 | 3.74 | 13.00 |
| ILMN_51277 | LOC305633 | (P) Antxr2 protein | 3.13 | 4.82 |
| ILMN_60046 | Serping1 | serine (or cysteine) peptidase inhibitor, clade G, member 1 | 2.93 | 4.63 |
| ILMN_48088 | Ifitm3 | (P) interferon induced transmembrane protein 3 | 2.74 | 1.99 |
| ILMN_55502 | C1qg | complement component 1, q subcomponent, y polypeptide | 2.73 | 2.62 |
| ILMN_53575 | Mt1a | Metallothionein | 2.69 | 6.02 |
| ILMN_58058 | Lcp1 | (P) lymphocyte cytosolic protein 1 | 2.68 | 2.07 |
| ILMN_60003 | Cd68 | (P) CD68 antigen | 2.62 | 3.34 |
| ILMN_60037 | Lgals3bp | lectin, galactoside-binding, soluble, 3 binding protein | 2.60 | 3.03 |
| ILMN_68224 | Gfap | (P) glial fibrillary acidic protein | 2.46 | 5.10 |
| ILMN_57422 | Serpinb1a | (P) serine (or cysteine) proteinase inhibitor, clade B, member 1a | 2.41 | 2.93 |
| ILMN_55731 | Bzrp | benzodiazepine receptor, peripheral | 2.38 | 2.43 |
| ILMN_47707 | Aif1 | allograft inflammatory factor 1 | 2.33 | 2.33 |
| ILMN_69642 | Arpc1b | actin related protein 2/3 complex, subunit 1B | 2.31 | 2.48 |
| ILMN_59412 | Emp3 | epithelial membrane protein 3 | 2.20 | 2.16 |
| ILMN_48069 | Crabp2 | cellular retinoic acid binding protein 2 | 2.12 | 8.63 |
| ILMN_67382 | Cd63 | CD63 antigen (Cd63) | 2.10 | 3.03 |
| ILMN_55706 | C1s | complement component 1, s subcomponent | 2.03 | 2.03 |
| ILMN_67686 | Ms4a6b | membrane-spanning 4-domains, subfamily A, member 6B | 2.03 | 2.22 |
| ILMN_61063 | Rhoc | (P) ras homolog gene family, member C | 2.02 | 2.71 |
| ILMN_54242 | Vim | vimentin | 1.96 | 2.69 |
| ILMN_55431 | Rnaset2 | (P) ribonuclease T2 | 1.88 | 1.79 |
| ILMN_62651 | Eif4ebp1 | eukaryotic translation initiation factor 4E binding protein 1 | 1.86 | 2.39 |
| ILMN_58496 | C1qa | complement component 1, q subcomponent, α polypeptide | 1.84 | 1.66 |
| ILMN_53085 | Irf1 | interferon regulatory factor 1 | 1.83 | 1.61 |
| ILMN_62100 | Ftl1 | ferritin light chain 1 | 1.74 | 2.28 |
| ILMN_59774 | Ppp1r14b | protein phosphatase 1, regulatory (inhibitor) subunit 14B | 1.74 | 3.36 |
| ILMN_59161 | Npc2 | Niemann Pick type C2 | 1.73 | 2.38 |

(P) predicted. [1]Fold-change over and above inosine's effect of decreasing stroke-induced changes. [2]Based on comparison between active regeneration state (induced by macrophage-derived factors) and normal control RGCs collected by FACS. From Fischer et al., 2004b (Supplementary data).

TABLE 3

Complement cascade genes in LCM-captured CSMNs contralateral a stroke: induction by inosine treatment.

| Target | Symbol | Definition | Fold-Induction |
|---|---|---|---|
| ILMN_58846 | Adn | (P) adipsin | 5.81 |
| ILMN_55502 | C1qg | complement component 1, q subcomponent, y polypeptide | 3.96 |
| ILMN_63608 | C2 | complement component 2 | 2.93 |
| ILMN_69719 | Bf | B-factor, properdin | 2.73 |
| ILMN_60046 | Serping1 | serine (or cysteine) peptidase inhibitor, clade G, member 1 | 2.20 |
| ILMN_51249 | C3 | (P) hypothetical gene supp. by NM_016994 (LOC497841) | 2.17 |
| ILMN_59751 | C4-2 | (P) complement component 4, gene 2 | 2.15 |
| ILMN_55706 | C1s | complement component 1, s subcomponent | 2.07 |
| ILMN_58496 | C1qa | complement component 1, q subcomponent, α polypeptide | 2.03 |
| ILMN_61448 | C1qb | complement component 1, q subcomponent, β polypeptide | 1.84 |

(P) predicted.

TABLE 4

Changes in gene expression in CSMNs contralateral to SMA infarct: effects of stroke alone and of inosine

| Pattern | Target | Symbol | Definition | Signal Intensity Treatment after Stroke | | | Fold-Induction | |
|---|---|---|---|---|---|---|---|---|
| | | | | Control | Saline | Inosine | Stroke, sal vs. cntrl | Stroke, ino vs. cntrl |
| Decreased by stroke alone, partially attenuated by inosine | ILMN_49819 | Dmp1 | dentin matrix protein 1 (Dmp1). | 701 | 103 | 267 | 0.15 | 0.38 |
| | ILMN_62999 | Ppp1cb | protein phosphatase 1, catalytic subunit, beta isoform (Ppp1cb). | 2223 | 431 | 940 | 0.19 | 0.42 |
| | ILMN_55909 | LOC502317 | (Pred., sim. to) Amyloid beta (A4) precursor-like protein 1 (LOC502317). | 1704 | 336 | 689 | 0.20 | 0.40 |
| | ILMN_56710 | Pnrc1 | proline rich 2 (Pnrc1). | 968 | 196 | 626 | 0.20 | 0.65 |
| | ILMN_51947 | LOC360807 | (Pred.) LOC360807 (LOC360807). | 1370 | 285 | 689 | 0.21 | 0.50 |
| | ILMN_59359 | Plcb1 | (Pred.) phospholipase C, beta 1 (Plcb1). | 875 | 199 | 512 | 0.23 | 0.59 |
| | ILMN_63947 | LOC306428 | (Pred., sim. to) Chain A, T13s Mutant Of Bovine 70 Kilodalton Heat Shock Protein | 1221 | 285 | 507 | 0.23 | 0.42 |
| | ILMN_57553 | Olfm3 | olfactomedin 3 (Olfm3). | 769 | 190 | 473 | 0.25 | 0.62 |
| | ILMN_68952 | Tde2 | tumor differentially expressed 1, like (Tde2). | 1036 | 260 | 545 | 0.25 | 0.53 |
| | ILMN_51968 | LOC498931 | (Pred., sim. to) short coiled-coil protein (LOC498931). | 1031 | 262 | 554 | 0.25 | 0.54 |
| | ILMN_65814 | Mal | myelin and lymphocyte protein (Mal). | 1166 | 307 | 465 | 0.26 | 0.40 |
| | ILMN_68736 | Rab40b | (Pred.) Rab40b, member RAS oncogene family (Rab40b). | 762 | 201 | 476 | 0.26 | 0.63 |
| | ILMN_55685 | LOC498618 | (Pred., sim. to) glyceraldehyde-3-phosphate dehydrogenase (LOC498618). | 6354 | 1681 | 3089 | 0.26 | 0.49 |
| | ILMN_65062 | LOC500501 | (Pred., sim. to) RIKEN cDNA 5830433M19 (LOC500501). | 1211 | 329 | 958 | 0.27 | 0.79 |
| | ILMN_49884 | Ralbp1 | ralA binding protein 1 (Ralbp1). | 2071 | 585 | 1553 | 0.28 | 0.75 |
| | ILMN_61607 | LOC500137 | (Pred., sim. to) NEX-1 (LOC500137). | 786 | 222 | 454 | 0.28 | 0.58 |
| | ILMN_50922 | LOC498489 | (Pred., sim. to) chromosome 14 open reading frame 35 (LOC498489). | 1240 | 351 | 603 | 0.28 | 0.49 |
| | ILMN_51868 | Tspan3 | tetraspanin 3 (Tspan3). | 8219 | 2352 | 3842 | 0.29 | 0.47 |
| | ILMN_57073 | Plp | proteolipid protein (Plp). | 2385 | 704 | 1222 | 0.30 | 0.51 |
| | ILMN_51108 | LOC499428 | (Pred.) LOC499428 (LOC499428). | 1358 | 405 | 678 | 0.30 | 0.50 |
| | ILMN_52257 | Scd2 | stearoyl-Coenzyme A desaturase 2 (Scd2). | 7087 | 2133 | 3009 | 0.30 | 0.42 |
| | ILMN_67961 | LOC287622 | (Pred., sim. to) adaptor molecule SRCASM (LOC287622). | 576 | 175 | 400 | 0.30 | 0.69 |
| | ILMN_54458 | Echdc1 | enoyl Coenzyme A hydratase domain containing 1 (Echdc1). | 795 | 244 | 531 | 0.31 | 0.67 |
| | ILMN_63474 | Gtl6 | (Pred.) gene trap locus 6 (Gtl6). | 589 | 183 | 302 | 0.31 | 0.51 |
| | ILMN_65610 | LOC497663 | (Pred.) hypothetical gene supported by NM_133381 (LOC497663). | 462 | 145 | 416 | 0.31 | 0.90 |
| | ILMN_48587 | Scarb2 | CD36 antigen (collagen type I receptor, thrombospondin receptor)-like 2 (Scarb2). | 804 | 258 | 569 | 0.32 | 0.71 |
| | ILMN_53763 | MGC94053 | similar to RECS1 (MGC94053). | 796 | 255 | 469 | 0.32 | 0.59 |
| | ILMN_65657 | Pafah1b2 | platelet-activating factor acetylhydrolase, isoform 1b, alpha2 subunit (Pafah1b2). | 737 | 237 | 411 | 0.32 | 0.56 |
| | ILMN_67463 | Ggcx | gamma-glutamyl carboxylase (Ggcx). | 566 | 183 | 526 | 0.32 | 0.93 |
| | ILMN_54123 | Scara3 | (Pred.) scavenger receptor class A, member 3 (Scara3). | 603 | 196 | 470 | 0.33 | 0.78 |
| | ILMN_55057 | Fuca2 | fucosidase, alpha-L-2, plasma (Fuca2). | 1177 | 384 | 662 | 0.33 | 0.56 |
| | ILMN_60584 | Mg87 | Mg87 protein (Mg87). | 1567 | 512 | 1251 | 0.33 | 0.80 |
| | ILMN_63299 | Rcn2 | reticulocalbin 2 (Rcn2). | 741 | 248 | 442 | 0.33 | 0.60 |
| | ILMN_67903 | Ca2 | carbonic anhydrase 2 (Ca2). | 2151 | 722 | 1008 | 0.34 | 0.47 |
| | ILMN_54109 | Rnf11 | (Pred.) ring finger protein 11 (Rnf11). | 1667 | 562 | 825 | 0.34 | 0.49 |
| | ILMN_60448 | Bckdhb | (Pred.) branched chain keto acid dehydrogenase E1, beta polypeptide | 458 | 158 | 281 | 0.34 | 0.61 |
| | ILMN_70426 | Rpl31 | ribosomal protein L31 (Rpl31). | 923 | 325 | 831 | 0.35 | 0.90 |
| | ILMN_51972 | LOC501619 | (Pred., sim. to) 40S ribosomal protein S29 (LOC501619). | 704 | 249 | 416 | 0.35 | 0.59 |
| | ILMN_64006 | LOC500436 | (Pred., sim. to) heat shock protein 8 (LOC500436). | 3918 | 1397 | 1871 | 0.36 | 0.48 |
| | ILMN_55270 | Grm3 | (Pred.) glutamate receptor, metabotropic 3 (Grm3). | 769 | 275 | 387 | 0.36 | 0.50 |
| | ILMN_48507 | Sfrs10 | splicing factor, arginine/serine-rich 10 (transformer 2 homolog, Drosophila) | 3836 | 1371 | 2745 | 0.36 | 0.72 |
| | ILMN_61213 | Pja2 | praja 2, RING-H2 motif containing (Pja2). | 4079 | 1467 | 2360 | 0.36 | 0.58 |
| | ILMN_66651 | Plekhb1 | evectin-1 (Plekhb1). | 2729 | 984 | 1687 | 0.36 | 0.62 |
| | ILMN_64007 | LOC366411 | (Pred., sim. to) ribosomal protein S24 (LOC366411). | 572 | 207 | 295 | 0.36 | 0.51 |
| | ILMN_52577 | LOC317508 | (Pred., sim. to) hypothetical protein FLJ14503 (LOC317508). | 845 | 308 | 493 | 0.36 | 0.58 |
| | ILMN_69031 | RGD1309158 | similar to RIKEN cDNA 2700038I16 (RGD1309158). | 1203 | 441 | 630 | 0.37 | 0.52 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_69708 | Ubl3 | (Pred.) ubiquitin-like 3 (Ubl3). | 576 | 212 | 479 | 0.37 | 0.83 |
| | ILMN_61521 | LOC500629 | (Pred., sim. to) alcohol dehydrogenase PAN2 (LOC500629). | 1607 | 592 | 946 | 0.37 | 0.59 |
| | ILMN_57928 | Tnnc2 | (Pred.) troponin C2, fast (Tnnc2). | 1346 | 500 | 650 | 0.37 | 0.48 |
| | ILMN_68903 | Sfxn3 | sideroflexin 3 (Sfxn3). | 460 | 172 | 261 | 0.37 | 0.57 |
| | ILMN_57520 | Lisch7 | liver-specific bHLH-Zip transcription factor 7 (Lisch7). | 698 | 263 | 484 | 0.38 | 0.69 |
| | ILMN_66820 | LOC501538 | (Pred.) LOC501538 (LOC501538). | 1775 | 673 | 1132 | 0.38 | 0.64 |
| | ILMN_67020 | Lxn | latexin (Lxn). | 598 | 227 | 433 | 0.38 | 0.72 |
| | ILMN_53046 | Ube2e3 | (Pred.) ubiquitin-conjugating enzyme E2E 3, UBC4/5 homolog (yeast) | 713 | 271 | 434 | 0.38 | 0.61 |
| | ILMN_56986 | Scg3 | secretogranin III (Scg3). | 1268 | 483 | 870 | 0.38 | 0.69 |
| | ILMN_58032 | LOC298490 | (Pred., sim. to) RIKEN cDNA 6330579B17 gene (LOC298490). | 2279 | 869 | 1407 | 0.38 | 0.62 |
| | ILMN_54140 | Gabarapl2 | GABA(A) receptor-associated protein like 2 (Gabarapl2). | 1762 | 674 | 1324 | 0.38 | 0.75 |
| | ILMN_61216 | Khdrbs3 | etoile, Sam68-like protein SLM-2 (Khdrbs3). | 3604 | 1378 | 2045 | 0.38 | 0.57 |
| | ILMN_67724 | Dcamkl1 | double cortin and calcium/calmodulin-dependent protein kinase-like 1 | 7497 | 2868 | 4398 | 0.38 | 0.59 |
| | ILMN_65702 | LOC501181 | (Pred., sim. to) EF hand domain containing 1 (LOC501181). | 543 | 208 | 268 | 0.38 | 0.49 |
| | ILMN_65667 | LOC294046 | (Pred., sim. to) heat shock protein 8 (LOC294046). | 3845 | 1474 | 2096 | 0.38 | 0.55 |
| | ILMN_53955 | Cnot7 | (Pred.) CCR4-NOT transcription complex, subunit 7 (Cnot7). | 711 | 272 | 427 | 0.38 | 0.60 |
| | ILMN_50467 | Rpn2 | ribophorin II (Rpn2). | 1173 | 452 | 835 | 0.39 | 0.71 |
| | ILMN_65510 | Hnrpf | heterogeneous nuclear ribonucleoprotein F (Hnrpf). | 2226 | 858 | 1922 | 0.39 | 0.86 |
| | ILMN_54288 | LOC501145 | (Pred., sim. to) KIAA1034-like DNA binding protein (LOC501145). | 897 | 351 | 626 | 0.39 | 0.70 |
| | ILMN_61840 | Slc6a15 | solute carrier family 6 (neurotransmitter transporter), member 15 (Slc6a15). | 2523 | 993 | 1093 | 0.39 | 0.43 |
| | ILMN_50221 | Snx2 | (Pred.) sorting nexin 2 (Snx2). | 2541 | 1000 | 1681 | 0.39 | 0.66 |
| | ILMN_55914 | Nr2f1 | (Pred.) nuclear receptor subfamily 2, group F, member 1 (Nr2f1). | 1013 | 399 | 526 | 0.39 | 0.52 |
| | ILMN_65309 | LOC499328 | (Pred., sim. to) riboflavin kinase (LOC499328). | 1695 | 672 | 899 | 0.40 | 0.53 |
| | ILMN_70369 | LOC366188 | (Pred., sim. to) RIKEN cDNA 3110001N18 (LOC366188). | 1291 | 512 | 1100 | 0.40 | 0.85 |
| | ILMN_56170 | Acsl3 | acyl-CoA synthetase long-chain family member 3 (Acsl3). | 785 | 312 | 389 | 0.40 | 0.50 |
| | ILMN_66036 | LOC299179 | (Pred., sim. to) RIKEN cDNA 1810020G14 (LOC299179). | 510 | 203 | 385 | 0.40 | 0.76 |
| | ILMN_60033 | Tspan2 | tetraspan 2 (Tspan2). | 2505 | 1001 | 1363 | 0.40 | 0.54 |
| | ILMN_49569 | Kcnc2 | potassium voltage gated channel, Shaw-related subfamily, member 2 (Kcnc2), transcript variant a. | 6397 | 2570 | 4642 | 0.40 | 0.73 |
| | ILMN_56183 | Scn1a | sodium channel, voltage-gated, type 1, alpha polypeptide (Scn1a). | 588 | 237 | 517 | 0.40 | 0.88 |
| | ILMN_50573 | RAMP4 | ribosome associated membrane protein 4 (RAMP4). | 727 | 293 | 544 | 0.40 | 0.75 |
| | ILMN_66272 | LOC317232 | (Pred., sim. To) melanoma antigen, family E, 1 (LOC317232). | 7410 | 2994 | 5211 | 0.40 | 0.70 |
| | ILMN_67275 | LOC498696 | (Pred., sim. To) heterogeneous nuclear ribonucleoprotein A0 (LOC498696). | 999 | 405 | 514 | 0.41 | 0.51 |
| | ILMN_59040 | Kifap3 | (Pred.) kinesin-associated protein 3 (Kifap3). | 420 | 171 | 270 | 0.41 | 0.64 |
| | ILMN_53256 | Hat1 | histone aminotransferase 1 (Hat1). | 522 | 213 | 362 | 0.41 | 0.69 |
| | ILMN_63297 | LOC366673 | (Pred., sim. To) vesicle transport through interaction with t-SNAREs 1B homolog (LOC366673). | 498 | 204 | 298 | 0.41 | 0.60 |
| | ILMN_57630 | Sc4mol | sterol-C4-methyl oxidase-like (Sc4mol). | 518 | 213 | 271 | 0.41 | 0.52 |
| | ILMN_58550 | Rab11a | RAB11a, member RAS oncogene family (Rab11a). | 1859 | 769 | 1039 | 0.41 | 0.56 |
| | ILMN_67273 | Ywhaq | tyrosine 3-monooxygenase/tryptophan 5-monooxygenase activation protein, theta polypeptide | 4326 | 1793 | 2844 | 0.41 | 0.66 |
| | ILMN_70270 | Zfp216 | (Pred.) zinc finger protein 216 (Zfp216). | 1342 | 558 | 888 | 0.42 | 0.66 |
| | ILMN_66350 | LOC305122 | (Pred., sim. To) mKIAA1107 protein (LOC305122). | 1335 | 556 | 771 | 0.42 | 0.58 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_48323 | LOC499423 | (Pred., sim. To) pyruvate kinase (EC 2.7.1.40) isozyme M2 - (LOC499423). | 1952 | 813 | 1043 | 0.42 | 0.53 |
| | ILMN_69224 | LOC289036 | adiponectin receptor 1 (LOC289036). | 2129 | 891 | 1532 | 0.42 | 0.72 |
| | ILMN_53076 | Arpc3 | (Pred.) actin related protein 2/3 complex, subunit 3 (Arpc3). | 618 | 261 | 423 | 0.42 | 0.68 |
| | ILMN_65587 | Psma7 | (Pred.) proteasome (prosome, macropain) subunit, alpha type 7 (Psma7). | 3316 | 1402 | 2058 | 0.42 | 0.62 |
| | ILMN_47889 | Uxs1 | UDP-glucuronate decarboxylase 1 (Uxs1). | 4348 | 1845 | 2868 | 0.42 | 0.66 |
| | ILMN_67885 | LOC501601 | (Pred., sim. To) riboflavin kinase (LOC501601). | 1454 | 618 | 791 | 0.43 | 0.54 |
| | ILMN_51717 | LOC497777 | (Pred.) hypothetical gene supported by NM_172066 (LOC497777). | 991 | 422 | 577 | 0.43 | 0.58 |
| | ILMN_65170 | LOC287212 | (Pred., sim. To) hypothetical protein FLJ31951 (LOC287212). | 2709 | 1157 | 1634 | 0.43 | 0.60 |
| | ILMN_59964 | LOC497728 | (Pred.) hypothetical gene supported by NM_024137 (LOC497728). | 2450 | 1050 | 1366 | 0.43 | 0.56 |
| | ILMN_58290 | Gdap2 | (Pred.) ganglioside-induced differentiation-associated-protein 2 | 553 | 238 | 319 | 0.43 | 0.58 |
| | ILMN_55879 | Klhl2 | (Pred.) kelch-like 2, Mayven (*Drosophila*) (Klhl2). | 665 | 286 | 516 | 0.43 | 0.78 |
| | ILMN_55667 | Map2k4 | (Pred.) mitogen activated protein kinase kinase 4 (Map2k4). | 13987 | 6049 | 9089 | 0.43 | 0.65 |
| | ILMN_50967 | Ube2m | (Pred.) ubiquitin-conjugating enzyme E2M (UBC12 homolog, yeast) | 561 | 243 | 332 | 0.43 | 0.59 |
| | ILMN_62620 | Rab18 | (Pred.) RAB18, member RAS oncogene family (Rab18). | 2938 | 1273 | 2230 | 0.43 | 0.76 |
| | ILMN_60653 | Ndfip1 | (Pred.) Nedd4 family interacting protein 1 (Ndfip1). | 455 | 197 | 362 | 0.43 | 0.80 |
| | ILMN_59956 | D123 | D123 gene product (D123). | 801 | 348 | 607 | 0.43 | 0.76 |
| | ILMN_68511 | Gsn | gelsolin (Gsn). | 3355 | 1460 | 2157 | 0.44 | 0.64 |
| | ILMN_57554 | Vmp1 | vacuole membrane protein 1 (Vmp1). | 2278 | 993 | 1305 | 0.44 | 0.57 |
| | ILMN_58816 | Dars | aspartyl-tRNA synthetase (Dars). | 456 | 199 | 349 | 0.44 | 0.76 |
| | ILMN_68337 | Lkap | limkain b1 (Lkap). | 1177 | 514 | 758 | 0.44 | 0.64 |
| | ILMN_62095 | Bpnt1 | bisphosphate 3'-nucleotidase 1 (Bpnt1). | 406 | 178 | 283 | 0.44 | 0.70 |
| | ILMN_48447 | Wee1 | (Pred.) wee 1 homolog (*S. pombe*) (Wee1). | 442 | 194 | 367 | 0.44 | 0.83 |
| | ILMN_65993 | MGC93921 | similar to calcyclin binding protein (MGC93921). | 1229 | 540 | 845 | 0.44 | 0.69 |
| | ILMN_66323 | Bbp | (Pred.) beta-amyloid binding protein precursor | 1972 | 872 | 1150 | 0.44 | 0.58 |
| | ILMN_69931 | LOC296126 | (Pred., sim. To) U5 snRNP-specific protein, 200 kDa (LOC296126). | 517 | 230 | 332 | 0.44 | 0.64 |
| | ILMN_60511 | Rbm18 | (Pred.) RNA binding motif protein 18 (Rbm18). | 484 | 215 | 301 | 0.44 | 0.62 |
| | ILMN_58092 | LOC290549 | heat shock protein (LOC290549). | 3476 | 1547 | 1870 | 0.44 | 0.54 |
| | ILMN_52827 | Nedd9 | (Pred.) neural precursor cell expressed, developmentally down-regulated gene 9 | 750 | 336 | 550 | 0.45 | 0.73 |
| | ILMN_55995 | Slc16a1 | solute carrier family 16 (monocarboxylic acid transporters), member 1 | 1468 | 658 | 827 | 0.45 | 0.56 |
| | ILMN_66300 | Spnb4 | (Pred.) spectrin beta 4 (Spnb4). | 1587 | 711 | 1147 | 0.45 | 0.72 |
| | ILMN_67572 | Kif3b | (Pred.) kinesin family member 3B (Kif3b). | 810 | 365 | 642 | 0.45 | 0.79 |
| | ILMN_48688 | Sec6l1 | (Pred.) SEC6-like 1 (*S. cerevisiae*) (Sec6l1). | 700 | 321 | 587 | 0.46 | 0.84 |
| | ILMN_67016 | Optn | optineurin (Optn). | 521 | 239 | 360 | 0.46 | 0.69 |
| | ILMN_65668 | Rchy1 | ring finger and CHY zinc finger domain containing 1 (Rchy1). | 539 | 248 | 416 | 0.46 | 0.77 |
| | ILMN_58730 | LOC499088 | (Pred., sim. To) MGC15476 protein (LOC499088). | 1844 | 848 | 1089 | 0.46 | 0.59 |
| | ILMN_48320 | Ap3s1 | (Pred.) adaptor-related protein complex 3, sigma 1 subunit (Ap3s1). | 520 | 239 | 285 | 0.46 | 0.55 |
| | ILMN_54747 | LOC498407 | (Pred., sim. To) purine rich element binding protein B (LOC498407). | 1960 | 908 | 1261 | 0.46 | 0.64 |
| | ILMN_60123 | Pgk1 | phosphoglycerate kinase 1 (Pgk1). | 9075 | 4218 | 5869 | 0.46 | 0.65 |
| | ILMN_56593 | Zfp68 | (Pred.) zinc finger protein 68 (Zfp68). | 1223 | 571 | 727 | 0.47 | 0.59 |
| | ILMN_49366 | LOC501195 | (Pred., sim. To) D1Ertd622e protein (LOC501195). | 1908 | 895 | 1460 | 0.47 | 0.77 |
| | ILMN_66823 | Slc25a11 | solute carrier family 25 (mitochondrial carrier; oxoglutarate carrier), member 11 (Slc25a11). | 404 | 190 | 263 | 0.47 | 0.65 |
| | ILMN_49300 | Ube4a | ubiquitin conjugation factor E4 A (Ube4a). | 2591 | 1219 | 1509 | 0.47 | 0.58 |
| | ILMN_48004 | LOC366193 | (Pred., sim. To) 40S ribosomal protein S3a (V-fos transformation effector protein) | 3577 | 1689 | 2396 | 0.47 | 0.67 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | | Treatment after Stroke | | Stroke, sal | Stroke, ino |
| Pattern | Target | Symbol | Definition | Control | Saline | Inosine | vs. cntrl | vs. cntrl |
| | ILMN_67036 | Psmc5 | peptidase (prosome, macropain) 26S subunit, ATPase 5 (Psmc5). | 2988 | 1411 | 1620 | 0.47 | 0.54 |
| | ILMN_64945 | Rtn4 | reticulon 4 (Rtn4). | 11343 | 5357 | 6518 | 0.47 | 0.57 |
| | ILMN_59789 | Bcas2 | (Pred.) breast carcinoma amplified sequence 2 (Bcas2). | 1207 | 579 | 1103 | 0.48 | 0.91 |
| | ILMN_69949 | LOC315463 | (Pred., sim. To) hypothetical protein BC011833 (LOC315463). | 1317 | 633 | 709 | 0.48 | 0.54 |
| | ILMN_52968 | Atp6v1h | (Pred.) vacuolar ATPase subunit H (Atp6v1h). | 852 | 413 | 525 | 0.49 | 0.62 |
| | ILMN_50686 | Cdc37l | (Pred.) cell division cycle 37 homolog (S. cerevisiae)-like (Cdc37l). | 750 | 365 | 625 | 0.49 | 0.83 |
| | ILMN_59483 | LOC291762 | (Pred., sim. To) cyclin D binding myb-like transcription factor 1 (LOC291762). | 1288 | 627 | 673 | 0.49 | 0.52 |
| | ILMN_53694 | Cnbp1 | cellular nucleic acid binding protein 1 (Cnbp1). | 5929 | 2891 | 4491 | 0.49 | 0.76 |
| | ILMN_62918 | Grinl1a | glutamate receptor, ionotropic, N-methyl D-aspartate-like 1A (Grinl1a). | 1008 | 492 | 667 | 0.49 | 0.66 |
| | ILMN_57967 | Hbld2 | HesB protein (Hbld2). | 2042 | 997 | 1095 | 0.49 | 0.54 |
| | ILMN_67222 | MGC72992 | similar to programmed cell death 10 (MGC72992). | 565 | 276 | 359 | 0.49 | 0.63 |
| | ILMN_68584 | Flot2 | flotillin 2 (Flot2). | 951 | 466 | 667 | 0.49 | 0.70 |
| | ILMN_66809 | Ppp1r11 | protein phosphatase 1, regulatory (inhibitor) subunit 11 (Ppp1r11). | 960 | 472 | 865 | 0.49 | 0.90 |
| | ILMN_56556 | Cetn3 | (Pred.) centrin 3 (Cetn3). | 1038 | 510 | 649 | 0.49 | 0.63 |
| | ILMN_53292 | LOC499978 | (Pred., sim. To) uinine ine, zeta (uinine reductase)-like 1 | 1342 | 666 | 970 | 0.50 | 0.72 |
| | ILMN_60417 | LOC309016 | (Pred., sim. to) WD repeat domain 11 (LOC309016). | 810 | 403 | 554 | 0.50 | 0.68 |
| | ILMN_60252 | Kbtbd9 | (Pred.) kelch repeat and BTB (POZ) domain containing 9 (Kbtbd9). | 1868 | 929 | 1263 | 0.50 | 0.68 |
| | ILMN_68892 | Dhcr24 | (Pred.) 24-dehydrocholesterol reductase (Dhcr24). | 1952 | 974 | 1032 | 0.50 | 0.53 |
| | ILMN_58897 | Emb | embigin (Emb). | 555 | 278 | 425 | 0.50 | 0.77 |
| | ILMN_56078 | Tpt1 | tumor protein, translationally-controlled 1 (Tpt1). | 12652 | 6346 | 11229 | 0.50 | 0.89 |
| | ILMN_67578 | Zfp422 | (Pred.) zinc finger protein 422 (Zfp422). | 565 | 284 | 557 | 0.50 | 0.99 |
| | ILMN_51588 | Ik | IK cytokine (Ik). | 504 | 253 | 417 | 0.50 | 0.83 |
| | ILMN_61367 | Dlgap1 | discs, large (Drosophila) homolog-associated protein 1 (Dlgap1). | 1828 | 922 | 1249 | 0.50 | 0.68 |
| | ILMN_52985 | MGC94339 | similar to BC002216 protein (MGC94339). | 777 | 393 | 547 | 0.50 | 0.70 |
| | ILMN_51716 | LOC499767 | (Pred.) LOC499767 (LOC499767). | 2678 | 1353 | 1723 | 0.51 | 0.64 |
| | ILMN_65450 | Psmb5 | (Pred.) proteasome (prosome, macropain) subunit, beta type 5 | 4149 | 2100 | 2709 | 0.51 | 0.65 |
| | ILMN_56896 | RGD1308082 | similar to px19-like protein (RGD1308082). | 691 | 350 | 428 | 0.51 | 0.62 |
| | ILMN_62325 | Ddx1 | (Pred.) DEAD (Asp-Glu-Ala-Asp) box polypeptide 1 (Ddx1). | 6188 | 3145 | 3553 | 0.51 | 0.57 |
| | ILMN_64781 | Magi3 | membrane-associated guanylate kinase-related (MAGI-3) (Magi3). | 599 | 305 | 472 | 0.51 | 0.79 |
| | ILMN_55905 | Tceal1 | transcription elongation factor A (SII)-like 1 (Tceal1). | 505 | 257 | 286 | 0.51 | 0.57 |
| | ILMN_60239 | Ndufa8 | (Pred.) NADH dehydrogenase (ubiquinone) 1 alpha subcomplex, 8 | 1008 | 514 | 572 | 0.51 | 0.57 |
| | ILMN_57697 | RGD1308373 | (Pred., sim. to) DKFZP566K1924 protein (RGD1308373). | 4406 | 2247 | 2921 | 0.51 | 0.66 |
| | ILMN_64237 | Bcl10 | B-cell CLL/lymphoma 10 (Bcl10). | 863 | 442 | 723 | 0.51 | 0.84 |
| | ILMN_49739 | Arfrp1 | ADP-ribosylation factor related protein 1 (Arfrp1). | 1091 | 565 | 1014 | 0.52 | 0.93 |
| | ILMN_63077 | LOC302559 | (Pred., sim. to) DNA segment, Chr X, Immunex 38, expressed | 1152 | 597 | 1031 | 0.52 | 0.89 |
| | ILMN_53195 | LOC309362 | (Pred., sim. to) Dynamin binding protein (Scaffold protein Tuba) | 487 | 252 | 498 | 0.52 | 1.02 |
| | ILMN_60542 | LOC360618 | (Pred., sim. to) ORM1-like 3 (LOC360618). | 1473 | 767 | 1021 | 0.52 | 0.69 |
| | ILMN_59546 | LOC315840 | (Pred., sim. to) Myosin VI (LOC315840). | 4305 | 2242 | 3649 | 0.52 | 0.85 |
| | ILMN_57719 | Gucy1b3 | guanylate cyclase 1, soluble, beta 3 (Gucy1b3). | 7000 | 3684 | 3956 | 0.53 | 0.57 |
| | ILMN_58180 | Rhob | rhoB gene (Rhob). | 532 | 280 | 276 | 0.53 | 0.52 |
| | ILMN_63884 | Cdc91l1 | CDC91 cell division cycle 91-like 1 (S. cerevisiae) (Cdc91l1). | 645 | 342 | 529 | 0.53 | 0.82 |
| | ILMN_52232 | LOC498727 | (Pred., sim. to) nucleolar protein 7, 27 kDa (LOC498727). | 583 | 309 | 322 | 0.53 | 0.55 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_48208 | LOC501052 | (Pred., sim. to) Fus1 protein (LOC501052). | 506 | 268 | 314 | 0.53 | 0.62 |
| | ILMN_58455 | P44s10 | proteasome regulatory particle subunit p44S10 (P44s10). | 2506 | 1334 | 1680 | 0.53 | 0.67 |
| | ILMN_51069 | Map4k3 | (Pred.) mitogen-activated protein kinase kinase kinase kinase 3 (Map4k3). | 3780 | 2015 | 2593 | 0.53 | 0.69 |
| | ILMN_48467 | LOC362736 | (Pred., sim. to) HECT domain containing 1 (LOC362736). | 3118 | 1668 | 2340 | 0.54 | 0.75 |
| | ILMN_68376 | LOC362750 | (Pred.) atlastin-like (LOC362750). | 1134 | 607 | 720 | 0.54 | 0.63 |
| | ILMN_49640 | Ddit4 | DNA-damage-inducible transcript 4 (Ddit4). | 634 | 340 | 542 | 0.54 | 0.86 |
| | ILMN_58789 | Nup155 | nucleoporin 155 (Nup155). | 644 | 345 | 502 | 0.54 | 0.78 |
| | ILMN_65426 | Tra1 | (Pred.) tumor rejection antigen gp96 (Tra1). | 1208 | 652 | 651 | 0.54 | 0.54 |
| | ILMN_54252 | Pdcd5 | (Pred.) programmed cell death 5 (Pdcd5). | 5673 | 3062 | 5021 | 0.54 | 0.89 |
| | ILMN_55647 | LOC297821 | (Pred., sim. to) F23N19.9 (LOC297821). | 1759 | 952 | 1145 | 0.54 | 0.65 |
| | ILMN_56754 | Cct7 | (Pred.) chaperonin subunit 7 (eta) (Cct7). | 1529 | 830 | 1250 | 0.54 | 0.82 |
| | ILMN_48524 | Tax1bp1 | Tax1 (human T-cell leukemia virus type I) binding protein 1 (Tax1bp1). | 672 | 366 | 494 | 0.54 | 0.74 |
| | ILMN_57787 | RGD1305875 | (Pred., sim. To) endothelial-derived gene 1 (RGD1305875). | 635 | 347 | 483 | 0.55 | 0.76 |
| | ILMN_67131 | Nup98 | (Pred.) nucleoporin 98 (Nup98). | 716 | 391 | 471 | 0.55 | 0.66 |
| | ILMN_48796 | Txndc7 | (Pred.) thioredoxin domain containing 7 (Txndc7). | 2017 | 1102 | 1595 | 0.55 | 0.79 |
| | ILMN_55010 | Cdk9 | cyclin-dependent kinase 9 (Cdk9). | 2545 | 1392 | 1547 | 0.55 | 0.61 |
| | ILMN_61227 | Uqcrfs1 | ubiquinol-cytochrome c reductase, Rieske iron-sulfur polypeptide 1 | 7902 | 4323 | 5252 | 0.55 | 0.66 |
| | ILMN_62579 | Lancl2 | (Pred.) LanC (bacterial lantibiotic synthetase component C)-like 2 | 1186 | 650 | 776 | 0.55 | 0.65 |
| | ILMN_66945 | S100a16 | (Pred.) S100 calcium binding protein A16 (S100a16). | 800 | 439 | 753 | 0.55 | 0.94 |
| | ILMN_66984 | LOC498099 | (Pred., sim. To) glyceraldehyde-3-phosphate dehydrogenase | 8398 | 4616 | 6289 | 0.55 | 0.75 |
| | ILMN_62554 | Cdh13 | cadherin 13 (Cdh13). | 612 | 339 | 444 | 0.56 | 0.73 |
| | ILMN_68605 | App | amyloid beta (A4) precursor protein (App). | 1833 | 1020 | 1051 | 0.56 | 0.57 |
| | ILMN_65663 | Mrpl48 | (Pred.) mitochondrial ribosomal protein L48 (Mrpl48). | 962 | 536 | 550 | 0.56 | 0.57 |
| | ILMN_55597 | Gnb2l1 | guanine nucleotide binding protein (G protein), beta polypeptide 2 like 1 | 453 | 252 | 409 | 0.56 | 0.90 |
| | ILMN_51053 | Scye1 | (Pred.) small inducible cytokine subfamily E, member 1 (Scye1). | 1546 | 862 | 943 | 0.56 | 0.61 |
| | ILMN_64286 | Pdcl3 | (Pred.) phosducin-like 3 (Pdcl3). | 475 | 266 | 550 | 0.56 | 1.16 |
| | ILMN_49251 | Usp47 | (Pred.) ubiquitin specific protease 47 (Usp47). | 6090 | 3419 | 4229 | 0.56 | 0.69 |
| | ILMN_59191 | LOC311241 | (Pred., sim. To) RIKEN cDNA 0610038L10 gene (LOC311241). | 511 | 288 | 327 | 0.56 | 0.64 |
| | ILMN_59184 | MGC93920 | similar to RIKEN cDNA 1700048E23 (MGC93920). | 718 | 406 | 441 | 0.56 | 0.61 |
| | ILMN_60795 | Dpm1 | (Pred.) dolichol-phosphate (beta-D) mannosyltransferase 1 (Dpm1). | 2244 | 1269 | 1700 | 0.57 | 0.76 |
| | ILMN_51495 | Hod | homeobox only domain (Hod). | 4112 | 2328 | 3499 | 0.57 | 0.85 |
| | ILMN_53225 | Phf3 | (Pred.) PHD finger protein 3 (Phf3). | 892 | 505 | 591 | 0.57 | 0.66 |
| | ILMN_59253 | Glud1 | glutamate dehydrogenase 1 (Glud1). | 3902 | 2213 | 3271 | 0.57 | 0.84 |
| | ILMN_47714 | Hint3 | (Pred.) histidine triad nucleotide binding protein 3 (Hint3). | 1073 | 610 | 814 | 0.57 | 0.76 |
| | ILMN_65139 | Ndufb5 | (Pred.) NADH dehydrogenase (ubiquinone) 1 beta subcomplex, 5 | 10439 | 5947 | 6117 | 0.57 | 0.59 |
| | ILMN_61655 | Eif4b | eukaryotic translation initiation factor 4B (Eif4b). | 940 | 537 | 687 | 0.57 | 0.73 |
| | ILMN_66039 | LOC500865 | (Pred., sim. To) RIKEN cDNA 5730410E15 gene (LOC500865). | 1510 | 863 | 1051 | 0.57 | 0.70 |
| | ILMN_49520 | Mrpl42 | (Pred.) mitochondrial ribosomal protein L42 (Mrpl42). | 499 | 286 | 472 | 0.57 | 0.95 |
| | ILMN_49184 | LOC296488 | (Pred., sim. To) RIKEN cDNA 2810409H07 (LOC296488). | 4465 | 2567 | 3345 | 0.57 | 0.75 |
| | ILMN_66460 | LOC292328 | (Pred., sim. To) RIKEN cDNA 1110012L19 (LOC292328). | 539 | 310 | 342 | 0.58 | 0.63 |
| | ILMN_60859 | Vapb | vesicle-associated membrane protein, associated protein B and C (Vapb). | 1003 | 579 | 623 | 0.58 | 0.62 |
| | ILMN_70390 | Sec13l1 | SEC13-like 1 (Sec13l1). | 573 | 331 | 422 | 0.58 | 0.74 |
| | ILMN_66555 | Stx7 | syntaxin 7 (Stx7). | 4277 | 2502 | 3032 | 0.58 | 0.71 |
| | ILMN_61228 | Stmn1 | stathmin 1 (Stmn1). | 1800 | 1064 | 1380 | 0.59 | 0.77 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_67429 | LOC360677 | (Pred., sim. To) BC003940 protein (LOC360677). | 473 | 280 | 401 | 0.59 | 0.85 |
| | ILMN_48372 | LOC501326 | (Pred., sim. To) glutamate receptor, ionotropic, N-methyl D-aspartate-like 1A | 960 | 569 | 662 | 0.59 | 0.69 |
| | ILMN_63494 | LOC361115 | (Pred., sim. to) tumor protein, translationally-controlled 1 (LOC361115). | 5203 | 3086 | 4514 | 0.59 | 0.87 |
| | ILMN_60672 | Thtpa | thiamine triphosphatase (Thtpa). | 1771 | 1052 | 1168 | 0.59 | 0.66 |
| Increased by stroke, partially attenuated by inosine | ILMN_49501 | LOC499620 | (Pred.) LOC499620 (LOC499620). | 323 | 4926 | 1511 | 15.25 | 4.68 |
| | ILMN_54263 | LOC499823 | (Pred., sim. to) LRRGT00001 (LOC499823). | 509 | 7277 | 2587 | 14.30 | 5.08 |
| | ILMN_56549 | LOC499029 | (Pred.) LOC499029 (LOC499029). | 219 | 2960 | 1056 | 13.53 | 4.82 |
| | ILMN_61913 | LOC498907 | (Pred., sim. to) LRRGT00004 (LOC498907). | 219 | 2711 | 719 | 12.40 | 3.29 |
| | ILMN_49036 | LOC500380 | (Pred., sim. to) LRRGT00008 (LOC500380). | 630 | 7312 | 1334 | 11.61 | 2.12 |
| | ILMN_49446 | LOC500960 | (Pred., sim. to) Da1-12 (LOC500960). | 319 | 3465 | 1022 | 10.87 | 3.21 |
| | ILMN_53850 | LOC501120 | (Pred.) LOC501120 (LOC501120). | 238 | 2432 | 724 | 10.21 | 3.04 |
| | ILMN_67352 | LOC501965 | (Pred., sim. to) mKIAA0112 protein (LOC501965). | 221 | 2224 | 846 | 10.06 | 3.83 |
| | ILMN_65267 | LOC498469 | (Pred.) LOC498469 (LOC498469). | 246 | 2311 | 812 | 9.39 | 3.30 |
| | ILMN_67899 | Olr1595 | olfactory receptor 1595 (Olr1595). | 131 | 1166 | 334 | 8.90 | 2.55 |
| | ILMN_66101 | LOC360303 | (Pred.) hypothetical LOC360303 (LOC360303). | 726 | 6222 | 1598 | 8.57 | 2.20 |
| | ILMN_69211 | Rgs9 | regulator of G-protein signaling 9 (Rgs9). | 1670 | 14215 | 1975 | 8.51 | 1.18 |
| | ILMN_64785 | LOC499103 | (Pred., sim. to) RIKEN cDNA A830041P22 gene (LOC499103). | 155 | 1280 | 409 | 8.24 | 2.63 |
| | ILMN_68324 | LOC306365 | (Pred., sim. to) spermatogenic cell-specific gene 2 (LOC306365). | 211 | 1681 | 794 | 7.96 | 3.76 |
| | ILMN_68513 | LOC498989 | (Pred., sim. to) Ab2-143 (LOC498989). | 2673 | 21049 | 6923 | 7.87 | 2.59 |
| | ILMN_58050 | LOC498076 | (Pred., sim. to) RIKEN cDNA 2410116l05 (LOC498076). | 2175 | 16502 | 3421 | 7.59 | 1.57 |
| | ILMN_67324 | LOC502902 | (Pred., sim. to) Clecsf12 protein (LOC502902). | 219 | 1662 | 674 | 7.57 | 3.07 |
| | ILMN_57479 | LOC501389 | (Pred., sim. to) novel protein (LOC501389). | 130 | 913 | 345 | 7.02 | 2.65 |
| | ILMN_52548 | LOC501169 | (Pred., sim. to) LRRGT00004 (LOC501169). | 154 | 1067 | 359 | 6.92 | 2.33 |
| | ILMN_48542 | LOC363306 | (Pred., sim. to) RIKEN cDNA 4930555G01 (LOC363306). | 239 | 1625 | 333 | 6.81 | 1.39 |
| | ILMN_54642 | LOC363265 | (Pred., sim. to) alpha-3 type IV collagen (LOC363265). | 153 | 1036 | 425 | 6.75 | 2.77 |
| | ILMN_66057 | LOC498197 | (Pred., sim. to) envelope glycoprotein (LOC498197). | 300 | 2016 | 647 | 6.73 | 2.16 |
| | ILMN_62672 | Herc6 | (Pred.) potential ubiquitin ligase (Herc6). | 249 | 1631 | 366 | 6.56 | 1.47 |
| | ILMN_57665 | LOC317070 | (Pred., sim. to) nidogen 2 protein (LOC317070). | 308 | 1986 | 984 | 6.45 | 3.20 |
| | ILMN_55508 | Olr856 | olfactory receptor 856 (Olr856). | 171 | 1026 | 326 | 6.01 | 1.91 |
| | ILMN_56535 | LOC315915 | (Pred., sim. to) hypothetical protein E230019M04 (LOC315915). | 195 | 1161 | 366 | 5.96 | 1.88 |
| | ILMN_60447 | LOC500988 | (Pred., sim. to) RCK (LOC500988). | 260 | 1537 | 300 | 5.92 | 1.15 |
| | ILMN_65190 | Rps29 | ribosomal protein S29 (Rps29). | 533 | 2862 | 1465 | 5.37 | 2.75 |
| | ILMN_65990 | Ppp1r14c | protein phosphatase 1, regulatory (inhibitor) subunit 14c (Ppp1r14c). | 538 | 2749 | 1155 | 5.11 | 2.15 |
| | ILMN_63600 | Mrpl16 | mitochondrial ribosomal protein L16 (Mrpl16). | 491 | 2483 | 603 | 5.06 | 1.23 |
| | ILMN_67056 | LOC503278 | (Pred., sim. to) testin (LOC503278). | 792 | 3879 | 711 | 4.90 | 0.90 |
| | ILMN_62341 | Dscr3 | (Pred.) Down syndrome critical region gene 3 (Dscr3). | 199 | 964 | 470 | 4.84 | 2.36 |
| | ILMN_52244 | Plp2_mapped | proteolipid protein 2 (mapped) (Plp2_mapped). | 399 | 1861 | 1247 | 4.67 | 3.13 |
| | ILMN_64124 | LOC364468 | (Pred., sim. to) TGF beta-inducible nuclear protein 1 (L-name related LNR42) (LOC364468). | 254 | 1126 | 459 | 4.43 | 1.81 |
| | ILMN_66724 | Ap1g2 | (Pred.) adaptor protein complex AP-1, gamma 2 subunit (Ap1g2). | 653 | 2680 | 1437 | 4.11 | 2.20 |
| | ILMN_68938 | Psmb8 | proteosome (prosome, macropain) subunit, beta type 8 (Psmb8). | 575 | 2344 | 1847 | 4.08 | 3.21 |
| | ILMN_56796 | LOC361786 | (Pred.) hypothetical LOC361786 (LOC361786). | 502 | 2036 | 661 | 4.06 | 1.32 |
| | ILMN_47767 | LOC498644 | (Pred., sim. to) Ac1-163 (LOC498644). | 786 | 3164 | 1622 | 4.03 | 2.06 |
| | ILMN_62509 | LOC303378 | (Pred., sim. to) schlafen 8 (LOC303378). | 184 | 737 | 562 | 4.00 | 3.05 |

TABLE 4-continued

Changes in gene expression in CSMNs contralateral to SMA infarct: effects of stroke alone and of inosine

| | | | | Signal Intensity | | | Fold-Induction | |
| | | | | Treatment after Stroke | | | Stroke, sal | Stroke, ino |
| Pattern | Target | Symbol | Definition | Control | Saline | Inosine | vs. cntrl | vs. cntrl |
| --- | --- | --- | --- | --- | --- | --- | --- | --- |
| | ILMN_51217 | Fmo4 | flavin containing monooxygenase 4 (Fmo4), transcript variant 2. | 236 | 905 | 345 | 3.84 | 1.46 |
| | ILMN_70095 | LOC497732 | (Pred.) hypothetical gene supported by NM_053806 (LOC497732). | 4902 | 18307 | 9201 | 3.73 | 1.88 |
| | ILMN_48708 | LOC298076 | (Pred., sim. to) hypothetical protein (LOC298076). | 351 | 1141 | 455 | 3.25 | 1.30 |
| | ILMN_69380 | Hapln2 | hyaluronan and proteoglycan link protein 2 (Hapln2). | 1652 | 5374 | 2652 | 3.25 | 1.61 |
| | ILMN_55173 | LOC499560 | (Pred., sim. to) LRRG00135 (LOC499560). | 325 | 1055 | 587 | 3.25 | 1.80 |
| | ILMN_49351 | LOC298381 | (Pred., sim. to) hypothetical protein D4Ertd765e (LOC298381). | 642 | 2074 | 991 | 3.23 | 1.54 |
| | ILMN_63938 | Ptplb | (Pred.) protein tyrosine phosphatase-like (proline instead of catalytic arginine), member b | 242 | 780 | 197 | 3.22 | 0.82 |
| | ILMN_50582 | Zmynd10 | zinc finger, MYND domain-containing 10 (Zmynd10). | 598 | 1919 | 1111 | 3.21 | 1.86 |
| | ILMN_48438 | Bat1a | HLA-B-associated transcript 1A (Bat1a). | 670 | 2125 | 1203 | 3.17 | 1.79 |
| | ILMN_54356 | Lrpb7 | (Pred.) leucine rich protein, B7 gene (Lrpb7). | 1722 | 5445 | 3768 | 3.16 | 2.19 |
| | ILMN_59298 | Acvr2b | (Pred.) activin receptor IIB (Acvr2b). | 360 | 1133 | 434 | 3.14 | 1.21 |
| | ILMN_62463 | Coro6 | coronin, actin binding protein 6 (Coro6). | 587 | 1802 | 991 | 3.07 | 1.69 |
| | ILMN_48874 | LOC362802 | (Pred., sim. to) RIKEN cDNA 1110038G14 (LOC362802). | 372 | 1143 | 753 | 3.07 | 2.02 |
| | ILMN_51302 | RGD1303232 | Phytn_dehydro and Pyr_redox domain containing protein RGD1303232 (RGD1303232). | 384 | 1161 | 835 | 3.02 | 2.17 |
| | ILMN_61189 | RGD1305132 | (Pred., sim. to) RIKEN cDNA A630065K24 (RGD1305132). | 395 | 1174 | 616 | 2.97 | 1.56 |
| | ILMN_49771 | LOC500297 | (Pred., sim. to) env precursor (LOC500297). | 1275 | 3677 | 1700 | 2.88 | 1.33 |
| | ILMN_50216 | Ifi30 | (Pred.) interferon gamma inducible protein 30 (Ifi30). | 289 | 823 | 678 | 2.85 | 2.35 |
| | ILMN_50979 | Scand1 | (Pred.) SCAN domain-containing 1 (Scand1). | 1695 | 4822 | 3790 | 2.84 | 2.24 |
| | ILMN_69698 | Brunol6 | (Pred.) bruno-like 6, RNA binding protein (Drosophila) | 284 | 789 | 305 | 2.78 | 1.07 |
| | ILMN_58341 | Rps17 | ribosomal protein S17 (Rps17). | 213 | 584 | 243 | 2.74 | 1.14 |
| | ILMN_69469 | Ocil | osteoclast inhibitory lectin (Ocil). | 198 | 540 | 284 | 2.73 | 1.44 |
| | ILMN_69153 | LOC311120 | (Pred., sim. to) ribosomal protein L15 (LOC311120). | 219 | 597 | 417 | 2.72 | 1.90 |
| | ILMN_58451 | Nt5 | 5 nucleotidase (Nt5). | 331 | 898 | 449 | 2.71 | 1.36 |
| | ILMN_65478 | Rab2l | RAB2, member RAS oncogene family-like (Rab2l). | 1651 | 4427 | 3661 | 2.68 | 2.22 |
| | ILMN_51640 | LOC361163 | (Pred., sim. to) LRRGT00078 (LOC361163). | 308 | 824 | 328 | 2.68 | 1.07 |
| | ILMN_50159 | Ptpn5 | protein tyrosine phosphatase, non-receptor type 5 (Ptpn5). | 991 | 2613 | 1782 | 2.64 | 1.80 |
| | ILMN_62775 | Gml | (Pred.) GPI anchored molecule like protein (Gml). | 313 | 825 | 594 | 2.63 | 1.90 |
| | ILMN_50085 | LOC295228 | (Pred., sim. to) RIKEN cDNA 2610029K21 (LOC295228). | 331 | 864 | 372 | 2.61 | 1.12 |
| | ILMN_54498 | Xrcc1 | X-ray repair complementing defective repair in Chinese hamster cells 1 (Xrcc1). | 1062 | 2732 | 2155 | 2.57 | 2.03 |
| | ILMN_67065 | LOC313760 | (Pred., sim. to) KIAA1751 protein (LOC313760). | 273 | 689 | 322 | 2.52 | 1.18 |
| | ILMN_63104 | LOC361571 | (Pred., sim. to) RIKEN cDNA 2410004H02 (LOC361571). | 695 | 1746 | 1345 | 2.51 | 1.93 |
| | ILMN_63186 | LOC292898 | (Pred., sim. to) RIKEN cDNA 1110061L23 (LOC292898). | 396 | 986 | 675 | 2.49 | 1.71 |
| | ILMN_67395 | Arrdc1 | (Pred.) arrestin domain containing 1 (Arrdc1). | 486 | 1209 | 1012 | 2.49 | 2.08 |
| | ILMN_58918 | LOC365891 | (Pred., sim. to) ribosomal protein L21 (LOC365891). | 548 | 1328 | 748 | 2.43 | 1.37 |
| | ILMN_64873 | Obfc1 | (Pred.) oligonucleotide/oligosaccharide-binding fold containing 1 | 363 | 879 | 571 | 2.42 | 1.57 |
| | ILMN_55668 | LOC497956 | (Pred., sim. to) human scavenger receptor class F, member 1 SCARF1 | 297 | 718 | 334 | 2.41 | 1.12 |
| | ILMN_64994 | LOC498171 | (Pred., sim. to) PRKR interacting protein 1 (IL11 inducible) (LOC498171). | 227 | 546 | 179 | 2.40 | 0.79 |
| | ILMN_54780 | Spag4 | sperm associated antigen 4 (Spag4). | 551 | 1323 | 903 | 2.40 | 1.64 |
| | ILMN_50874 | Zfp98 | (Pred.) zinc finger protein 98 (Zfp98). | 492 | 1166 | 663 | 2.37 | 1.35 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_57776 | LOC287419 | (Pred., sim. to) Ran-interacting protein MOG1 (LOC287419). | 1393 | 3273 | 2464 | 2.35 | 1.77 |
| | ILMN_63117 | LOC500039 | (Pred., sim. to) Adenylate kinase 2 (LOC500039). | 1268 | 2966 | 2009 | 2.34 | 1.59 |
| | ILMN_57726 | Pom210 | nuclear pore membrane glycoprotein 210 (Pom210). | 414 | 955 | 628 | 2.30 | 1.52 |
| | ILMN_60621 | Mbd6 | (Pred.) methyl-CpG binding domain protein 6 (Mbd6). | 668 | 1524 | 1286 | 2.28 | 1.93 |
| | ILMN_66715 | LOC304396 | (Pred., sim. to) hypothetical protein DKFZp434K1815 (LOC304396). | 345 | 780 | 591 | 2.26 | 1.71 |
| | ILMN_52976 | LOC362819 | (Pred., sim. to) RIKEN cDNA 1110005A23 (LOC362819). | 3321 | 7434 | 6968 | 2.24 | 2.10 |
| | ILMN_62453 | Cml2 | Camello-like 2 (Cml2). | 402 | 898 | 653 | 2.23 | 1.62 |
| | ILMN_49489 | Plec1 | plectin 1 (Plec1). | 2413 | 5372 | 4381 | 2.23 | 1.82 |
| | ILMN_62639 | LOC286990 | epidermal Langerhans cell protein LCP1 (LOC286990). | 1027 | 2283 | 968 | 2.22 | 0.94 |
| | ILMN_49573 | Tp53 | tumor protein p53 (Tp53). | 243 | 536 | 410 | 2.20 | 1.68 |
| | ILMN_65421 | LOC500504 | (Pred.) LOC500504 (LOC500504). | 1734 | 3810 | 3307 | 2.20 | 1.91 |
| | ILMN_60479 | LOC302528 | (Pred., sim. to) 60S ribosomal protein L37a (LOC302528). | 592 | 1302 | 1079 | 2.20 | 1.82 |
| | ILMN_48777 | Exosc8 | (Pred.) exosome component 8 (Exosc8). | 636 | 1392 | 1006 | 2.19 | 1.58 |
| | ILMN_47745 | LOC362983 | (Pred., sim. to) RIKEN cDNA A630054L15; hypothetical protein MGC38041 | 440 | 955 | 699 | 2.17 | 1.59 |
| | ILMN_67592 | Commd4 | (Pred.) COMM domain containing 4 (Commd4). | 2692 | 5811 | 5716 | 2.16 | 2.12 |
| | ILMN_66046 | MGC94099 | similar to Git2 protein (MGC94099). | 2053 | 4397 | 3127 | 2.14 | 1.52 |
| | ILMN_57351 | Dpp7 | dipeptidylpeptidase 7 (Dpp7). | 2197 | 4705 | 3825 | 2.14 | 1.74 |
| | ILMN_52050 | Ddx49 | (Pred.) DEAD (Asp-Glu-Ala-Asp) box polypeptide 49 | 395 | 843 | 470 | 2.14 | 1.19 |
| | ILMN_62671 | LOC301126 | (Pred., sim. to) Safb2 protein (LOC301126). | 2829 | 6047 | 5559 | 2.14 | 1.96 |
| | ILMN_56525 | Gadd45g | (Pred.) growth arrest and DNA-damage-inducible 45 gamma (Gadd45g). | 535 | 1135 | 717 | 2.12 | 1.34 |
| | ILMN_67962 | LOC303744 | (Pred., sim. to) hypothetical protein BC013995 (LOC303744). | 544 | 1155 | 673 | 2.12 | 1.24 |
| | ILMN_61572 | Psmb6 | proteasome (prosome, macropain) subunit, beta type 6 (Psmb6). | 2743 | 5822 | 3704 | 2.12 | 1.35 |
| | ILMN_49463 | LOC498525 | (Pred., sim. to) Bm403207 (LOC498525). | 584 | 1232 | 755 | 2.11 | 1.29 |
| | ILMN_62981 | LOC307834 | (Pred., sim. to) 4930566A11Rik protein (LOC307834). | 1055 | 2185 | 1690 | 2.07 | 1.60 |
| | ILMN_51797 | LOC499185 | (Pred., sim. to) mitochondrial ribosomal protein S11 (LOC499185). | 2024 | 4182 | 2884 | 2.07 | 1.42 |
| | ILMN_66091 | Ogt | O-linked N-acetylglucosamine (GlcNAc) transferase | 237 | 489 | 279 | 2.06 | 1.17 |
| | ILMN_59466 | Actl6 | (Pred.) actin-like 6 (Actl6). | 2724 | 5609 | 3978 | 2.06 | 1.46 |
| | ILMN_52845 | Egfl7 | EGF-like domain 7 (Egfl7). | 500 | 1028 | 759 | 2.06 | 1.52 |
| | ILMN_51557 | Helz | (Pred.) helicase with zinc finger domain (Helz). | 593 | 1218 | 712 | 2.05 | 1.20 |
| | ILMN_48506 | Rac2 | RAS-related C3 botulinum substrate 2 (Rac2). | 526 | 1080 | 1577 | 2.05 | 3.00 |
| | ILMN_56701 | RT1-S3 | (Pred.) RT1 class Ib, locus S3 (RT1-S3). | 500 | 1025 | 472 | 2.05 | 0.94 |
| | ILMN_50464 | LOC305467 | (Pred., sim. to) novel protein (LOC305467). | 1091 | 2231 | 1876 | 2.05 | 1.72 |
| | ILMN_66426 | Fbxl6 | F-box and leucine-rich repeat protein 6 (Fbxl6). | 1207 | 2453 | 1593 | 2.03 | 1.32 |
| | ILMN_52155 | Ddx39 | nuclear RNA helicase, DECD variant of DEAD box family (Ddx39). | 1158 | 2336 | 1581 | 2.02 | 1.36 |
| | ILMN_55049 | Prkag1 | protein kinase, AMP-activated, gamma 1 non-catalytic subunit (Prkag1). | 565 | 1139 | 775 | 2.01 | 1.37 |
| | ILMN_62902 | KIFC2 | kinesin family member C2 (KIFC2). | 3840 | 7684 | 7520 | 2.00 | 1.96 |
| | ILMN_58403 | RGD1311136 | (Pred.) membralin (RGD1311136). | 343 | 685 | 515 | 2.00 | 1.50 |
| | ILMN_52019 | Rad52 | (Pred.) RAD52 homolog (S. cerevisiae) (Rad52). | 728 | 1440 | 1093 | 1.98 | 1.50 |
| | ILMN_67932 | RGD1306721 | (Pred., sim. to) helicase-like protein NHL isoform 2 (RGD1306721). | 1357 | 2673 | 2351 | 1.97 | 1.73 |
| | ILMN_52017 | Nspc1 | (Pred.) nervous system polycomb 1 (Nspc1). | 405 | 795 | 600 | 1.97 | 1.48 |
| | ILMN_62148 | LOC366848 | (Pred., sim. to) NG28 (LOC366848). | 407 | 796 | 739 | 1.96 | 1.82 |
| | ILMN_67909 | Junb | Jun-B oncogene (Junb). | 742 | 1449 | 1186 | 1.95 | 1.60 |
| | ILMN_62719 | LOC296870 | (Pred., sim. to) ribosomal protein L34 (LOC296870). | 2187 | 4242 | 4059 | 1.94 | 1.86 |
| | ILMN_63766 | Pkn1 | protein kinase N1 (Pkn1). | 1404 | 2721 | 2365 | 1.94 | 1.69 |

TABLE 4-continued

Changes in gene expression in CSMNs contralateral to SMA infarct: effects of stroke alone and of inosine

| Pattern | Target | Symbol | Definition | Signal Intensity | | | Fold-Induction | |
|---|---|---|---|---|---|---|---|---|
| | | | | Treatment after Stroke | | | Stroke, sal vs. cntrl | Stroke, ino vs. cntrl |
| | | | | Control | Saline | Inosine | | |
| | ILMN_56510 | LOC303790 | (Pred., sim. to) RIKEN cDNA 4122402O22 (LOC303790). | 1587 | 3071 | 2300 | 1.93 | 1.45 |
| | ILMN_50833 | Rfx1 | (Pred.) regulatory factor X, 1 (influences HLA class II expression) | 3305 | 6372 | 4995 | 1.93 | 1.51 |
| | ILMN_69140 | Aurkc | (Pred.) aurora kinase C (Aurkc). | 821 | 1580 | 1172 | 1.92 | 1.43 |
| | ILMN_59080 | Rbl2 | retinoblastoma-like 2 (Rbl2). | 818 | 1573 | 1060 | 1.92 | 1.30 |
| | ILMN_55276 | Chd4 | (Pred.) chromodomain helicase DNA binding protein 4 (Chd4). | 5906 | 11336 | 7413 | 1.92 | 1.26 |
| | ILMN_54711 | LOC500226 | (Pred., sim. to) D3Mm3e (LOC500226). | 3768 | 7229 | 7922 | 1.92 | 2.10 |
| | ILMN_62527 | LOC291847 | (Pred., sim. to) hypothetical protein 4933409I22 (LOC291847). | 422 | 807 | 558 | 1.91 | 1.32 |
| | ILMN_57870 | Lap3 | (Pred.) leucine aminopeptidase 3 (Lap3). | 914 | 1741 | 918 | 1.91 | 1.01 |
| | ILMN_54303 | LOC498614 | (Pred., sim. to) transcription elongation factor B (SIII), polypeptide 1 | 2251 | 4286 | 2373 | 1.90 | 1.05 |
| | ILMN_58258 | LOC317579 | (Pred., sim. to) KIAA0266 gene product (LOC317579). | 483 | 913 | 733 | 1.89 | 1.52 |
| | ILMN_62537 | Rhot2 | MIRO2 protein (Rhot2). | 663 | 1250 | 1112 | 1.89 | 1.68 |
| | ILMN_66205 | LOC497739 | (Pred.) hypothetical gene supported by NM_021579 (LOC497739). | 2947 | 5499 | 4864 | 1.87 | 1.65 |
| | ILMN_48330 | Comt | catechol-O-methyltransferase (Comt). | 367 | 683 | 400 | 1.86 | 1.09 |
| | ILMN_66828 | Pnck | pregnancy upregulated non-ubiquitously expressed CaM kinase (Pnck). | 5435 | 10061 | 8946 | 1.85 | 1.65 |
| | ILMN_57817 | Soc | socius (Soc). | 989 | 1829 | 1341 | 1.85 | 1.36 |
| | ILMN_65374 | Oplah | 5-oxoprolinase (ATP-hydrolysing) (Oplah). | 1189 | 2199 | 2440 | 1.85 | 2.05 |
| | ILMN_68450 | Slc35b4 | (Pred.) solute carrier family 35, member B4 (Slc35b4). | 304 | 554 | 430 | 1.82 | 1.41 |
| | ILMN_60781 | RGD1309326 | (Pred., sim. to) RIKEN cDNA 2410002F23 (RGD1309326). | 1636 | 2972 | 2333 | 1.82 | 1.43 |
| | ILMN_53013 | Map2k6 | mitogen-activated protein kinase kinase 6 (Map2k6). | 3340 | 6045 | 3981 | 1.81 | 1.19 |
| | ILMN_62401 | LOC301122 | (Pred., sim. to) putative zinc finger protein (LOC301122). | 759 | 1370 | 925 | 1.80 | 1.22 |
| | ILMN_56966 | Dhrsx | (Pred.) dehydrogenase/reductase (SDR family) X chromosome (Dhrsx). | 5798 | 10423 | 8022 | 1.80 | 1.38 |
| | ILMN_64738 | LOC303702 | (Pred., sim. to) RIKEN cDNA D230014K01 (LOC303702). | 523 | 940 | 899 | 1.80 | 1.72 |
| | ILMN_57902 | Tm6p1 | fasting-inducible integral membrane protein TM6P1 (Tm6p1). | 771 | 1383 | 1532 | 1.79 | 1.99 |
| | ILMN_50502 | Plcd1 | phospholipase C, delta 1 (Plcd1). | 796 | 1425 | 1514 | 1.79 | 1.90 |
| | ILMN_53105 | Slc9a1 | solute carrier family 9, member 1 (Slc9a1). | 1585 | 2821 | 2100 | 1.78 | 1.32 |
| | ILMN_56164 | Pfc | (Pred.) properdin factor, complement (Pfc). | 682 | 1211 | 1375 | 1.78 | 2.02 |
| | ILMN_51834 | Srebf1 | (Pred.) sterol regulatory element binding factor 1 (Srebf1). | 726 | 1290 | 1069 | 1.78 | 1.47 |
| | ILMN_53114 | Unc93b | (Pred.) unc-93 homolog B (C. elegans) (Unc93b). | 285 | 507 | 600 | 1.78 | 2.10 |
| | ILMN_54591 | Trim39 | tripartite motif protein 39 (Trim39). | 1003 | 1776 | 1351 | 1.77 | 1.35 |
| | ILMN_60367 | LOC305076 | (Pred., sim. to) hypothetical protein MGC29875; similar to YIL091C | 527 | 928 | 824 | 1.76 | 1.56 |
| | ILMN_62932 | LOC362015 | (Pred., sim. to) adenosine monophosphate deaminase 2 (isoform L) (LOC362015). | 939 | 1648 | 1285 | 1.75 | 1.37 |
| | ILMN_57761 | Cdk5rap2 | (Pred.) CDK5 activator-binding protein (Cdk5rap2). | 820 | 1435 | 1377 | 1.75 | 1.68 |
| | ILMN_62725 | Cd151 | CD151 antigen (Cd151). | 779 | 1362 | 1171 | 1.75 | 1.50 |
| | ILMN_50957 | Cml1 | camello-like 1 (Cml1). | 255 | 443 | 275 | 1.74 | 1.08 |
| | ILMN_58921 | LOC295941 | (Pred., sim. to) ribosomal protein L21 (LOC295941). | 3723 | 6457 | 3970 | 1.73 | 1.07 |
| | ILMN_55987 | Ptprr | protein tyrosine phosphatase, receptor type, R (Ptprr). | 648 | 1119 | 676 | 1.73 | 1.04 |
| | ILMN_59207 | Polrmt | (Pred.) polymerase (RNA) mitochondrial (DNA directed) | 804 | 1386 | 1219 | 1.72 | 1.52 |
| | ILMN_67281 | LOC498957 | (Pred., sim. to) cDNA sequence BC025816 (LOC498957). | 845 | 1455 | 1081 | 1.72 | 1.28 |
| | ILMN_48288 | LOC300149 | (Pred., sim. to) hypothetical protein D15Ertd785e (LOC300149). | 2084 | 3568 | 2789 | 1.71 | 1.34 |
| | ILMN_63846 | LOC304116 | (Pred., sim. to) 60S ribosomal protein L7a (LOC304116). | 395 | 674 | 393 | 1.71 | 0.99 |
| | ILMN_53204 | LOC362304 | (Pred., sim. to) ORC5-related protein (LOC362304). | 3781 | 6455 | 5067 | 1.71 | 1.34 |
| | ILMN_54994 | Ing4 | (Pred.) inhibitor of growth family, member 4 (Ing4). | 1161 | 1980 | 1169 | 1.70 | 1.01 |
| | ILMN_59638 | Fxr2h | (Pred.) fragile X mental retardation gene 2, autosomal homolog (Fxr2h). | 388 | 660 | 638 | 1.70 | 1.64 |

TABLE 4-continued

Changes in gene expression in CSMNs contralateral to SMA infarct: effects of stroke alone and of inosine

| Pattern | Target | Symbol | Definition | Signal Intensity | | | Fold-Induction | |
|---|---|---|---|---|---|---|---|---|
| | | | | | Treatment after Stroke | | Stroke, sal | Stroke, ino |
| | | | | Control | Saline | Inosine | vs. cntrl | vs. cntrl |
| Decreased by stroke alone, not attenuated by inosine | ILMN_57701 | Esd | (Pred.) Esterase D/formylglutathione hydrolase (Esd). | 3253 | 1670 | 1416 | 0.51 | 0.44 |
| | ILMN_62809 | Btf3 | basic transcription factor 3 (Btf3). | 1824 | 926 | 787 | 0.51 | 0.43 |
| | ILMN_57304 | Sgpp1 | (Pred.) sphingosine-1-phosphate phosphatase 1 (Sgpp1). | 725 | 335 | 316 | 0.46 | 0.44 |
| | ILMN_64100 | LOC362857 | (Pred., sim. to) hypothetical protein MGC17943 (LOC362857). | 2500 | 1133 | 1081 | 0.45 | 0.43 |
| | ILMN_61547 | LOC361080 | (Pred., sim. to) Peptidyl-prolyl cis-trans isomerase A (PPlase) (Rotamase) | 736 | 259 | 295 | 0.35 | 0.40 |
| Increased by stroke alone, increased further by inosine | ILMN_53325 | LOC498335 | (Pred., sim. to) Small inducible cytokine B13 precursor (CXCL13) | 131 | 1421 | 3310 | 10.84 | 25.26 |
| | ILMN_51249 | LOC497841 | (Pred.) hypothetical gene supported by NM_016994 (LOC497841). | 247 | 1917 | 2841 | 7.77 | 11.52 |
| | ILMN_59933 | RT1-Da | (Pred.) RT1 class II, locus Da (RT1-Da). | 276 | 1992 | 3072 | 7.21 | 11.11 |
| | ILMN_65212 | Cyba | cytochrome b-245, alpha polypeptide (Cyba). | 647 | 1517 | 2617 | 2.35 | 4.04 |
| | ILMN_53575 | Mt1a | Metallothionein (Mt1a). | 889 | 2264 | 3267 | 2.55 | 3.68 |
| | ILMN_60003 | Cd68 | (Pred.) CD68 antigen (Cd68). | 546 | 1775 | 2117 | 3.25 | 3.88 |
| | ILMN_50991 | Asb2 | (Pred.) ankyrin repeat and SOCS box-containing protein 2 (Asb2). | 188 | 563 | 615 | 2.99 | 3.27 |
| | ILMN_63608 | C2 | complement component 2 (C2). | 1318 | 4041 | 4113 | 3.07 | 3.12 |
| | ILMN_54011 | Tle2 | (Pred.) transducin-like enhancer of split 2, homolog of Drosophila E(spl) | 758 | 2543 | 2295 | 3.36 | 3.03 |
| | ILMN_51700 | Irf3 | interferon regulatory factor 3 (Irf3). | 4354 | 16208 | 12720 | 3.72 | 2.92 |
| | ILMN_55431 | Rnaset2 | (Pred.) ribonuclease T2 (Rnaset2). | 3133 | 5775 | 7227 | 1.84 | 2.31 |
| | ILMN_61346 | LOC500804 | (Pred., sim. to) Ferritin light chain (Ferritin L subunit) (LOC500804). | 2342 | 5052 | 5507 | 2.16 | 2.35 |
| | ILMN_65350 | Dtx2 | (Pred.) deltex 2 homolog (Drosophila) (Dtx2). | 801 | 1527 | 1792 | 1.91 | 2.24 |
| | ILMN_49099 | LOC499244 | (Pred., sim. to) ferritin light chain (LOC499244). | 6623 | 13841 | 14824 | 2.09 | 2.24 |
| | ILMN_62100 | Ftl1 | ferritin light chain 1 (Ftl1). | 5237 | 11137 | 11718 | 2.13 | 2.24 |
| | ILMN_59774 | Ppp1r14b | protein phosphatase 1, regulatory (inhibitor) subunit 14B (Ppp1r14b). | 916 | 2012 | 2071 | 2.20 | 2.26 |
| Not changed by stroke alone, significantly upregulated by inosine | ILMN_58846 | Adn | (Pred.) adipsin (Adn). | 505 | 755 | 2287 | 1.49 | 4.53 |
| | ILMN_47969 | ADRP | adipose differentiation-related protein (ADRP). | 777 | 1360 | 3202 | 1.75 | 4.12 |
| | ILMN_66176 | Arhgdib | Rho, GDP dissociation inhibitor (GDI) beta (Arhgdib). | 749 | 1138 | 3057 | 1.52 | 4.08 |
| | ILMN_65961 | LOC498279 | (Pred., sim. to) NADH dehydrogenase (ubiquinone) Fe—S protein 2 | 2186 | 3801 | 8892 | 1.74 | 4.07 |
| | ILMN_70335 | A2m | alpha-2-macroglobulin (A2m). | 477 | 452 | 1924 | 0.95 | 4.03 |
| | ILMN_54332 | Igfbp2 | insulin-like growth factor binding protein 2 (Igfbp2). | 957 | 1201 | 3801 | 1.26 | 3.97 |
| | ILMN_60870 | Smoc2 | (Pred.) SPARC related modular calcium binding 2 (Smoc2). | 297 | 796 | 1123 | 2.68 | 3.79 |
| | ILMN_48641 | LOC360644 | (Pred.) hypothetical LOC360644 (LOC360644). | 164 | 267 | 602 | 1.63 | 3.68 |
| | ILMN_55502 | C1qg | complement component 1, q subcomponent, gamma polypeptide (C1qg). | 683 | 1644 | 2499 | 2.41 | 3.66 |
| | ILMN_62559 | Timp1 | tissue inhibitor of metalloproteinase 1 (Timp1). | 643 | 556 | 2293 | 0.86 | 3.57 |
| | ILMN_61314 | Ptpn6 | protein tyrosine phosphatase, non-receptor type 6 (Ptpn6). | 272 | 598 | 957 | 2.20 | 3.52 |
| | ILMN_62703 | Bcl2a1 | B-cell leukemia/lymphoma 2 related protein A1 (Bcl2a1). | 184 | 203 | 613 | 1.11 | 3.34 |
| | ILMN_60046 | Serping1 | serine (or cysteine) peptidase inhibitor, clade G, member 1 (Serping1). | 392 | 509 | 1251 | 1.30 | 3.19 |
| | ILMN_60037 | Lgals3bp | lectin, galactoside-binding, soluble, 3 binding protein (Lgals3bp). | 210 | 323 | 629 | 1.54 | 3.00 |
| | ILMN_57609 | Plek | (Pred.) pleckstrin (Plek). | 647 | 785 | 1937 | 1.21 | 2.99 |
| | ILMN_51277 | LOC305633 | (Pred., sim. to) Antxr2 protein (LOC305633). | 684 | 594 | 2047 | 0.87 | 2.99 |
| | ILMN_59751 | C4-2 | (Pred.) complement component 4, gene 2 (C4-2). | 818 | 2351 | 2409 | 2.87 | 2.95 |
| | ILMN_161110 | | similar to myo-inositol 1-phosphate synthase A1 (cDNA clone MGC:93930) | 1118 | 2258 | 3241 | 2.02 | 2.90 |
| | ILMN_68224 | Gfap | (Pred.) glial fibrillary acidic protein (Gfap). | 8016 | 12839 | 23099 | 1.60 | 2.88 |
| | ILMN_62382 | Card9 | caspase recruitment domain family, member 9 (Card9). | 306 | 730 | 865 | 2.38 | 2.83 |
| | ILMN_52949 | Tcirg1 | (Pred.) T-cell, immune regulator 1, ATPase, H+ transporting, lysosomal V0 protein a isoform 3 | 773 | 1377 | 2173 | 1.78 | 2.81 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | | Treatment after Stroke | | Stroke, sal | Stroke, ino |
| Pattern | Target | Symbol | Definition | Control | Saline | Inosine | vs. cntrl | vs. cntrl |
| | ILMN_61448 | C1qb | complement component 1, q subcomponent, beta polypeptide (C1qb). | 663 | 1371 | 1832 | 2.07 | 2.76 |
| | ILMN_58058 | Lcp1 | (Pred.) lymphocyte cytosolic protein 1 (Lcp1). | 473 | 520 | 1306 | 1.10 | 2.76 |
| | ILMN_58236 | LOC498185 | (Pred., sim. to) sodium/calcium exchanger protein (LOC498185). | 291 | 517 | 804 | 1.77 | 2.76 |
| | ILMN_48088 | Ifitm3 | (Pred.) interferon induced transmembrane protein 3 (Ifitm3). | 927 | 896 | 2516 | 0.97 | 2.71 |
| | ILMN_49934 | Nfkbia | (Pred.) nuclear factor of kappa light chain gene enhancer in B-cells inhibitor, alpha | 1209 | 2449 | 3250 | 2.03 | 2.69 |
| | ILMN_57422 | Serpinb1a | (Pred.) serine (or cysteine) proteinase inhibitor, Glade B, member 1a | 219 | 305 | 589 | 1.39 | 2.68 |
| | ILMN_58882 | Rhoj | ras homolog gene family, member J (Rhoj). | 220 | 330 | 588 | 1.50 | 2.67 |
| | ILMN_47707 | Aif1 | allograft inflammatory factor 1 (Aif1). | 1611 | 2417 | 4301 | 1.50 | 2.67 |
| | ILMN_65999 | Man2b1 | mannosidase 2, alpha B1 (Man2b1). | 636 | 1558 | 1676 | 2.45 | 2.64 |
| | ILMN_61895 | LOC360627 | (Pred., sim. to) 65 kDa FK506-binding protein (LOC360627). | 406 | 637 | 1064 | 1.57 | 2.62 |
| | ILMN_48069 | Crabp2 | cellular retinoic acid binding protein 2 (Crabp2). | 384 | 728 | 1006 | 1.90 | 2.62 |
| | ILMN_69642 | Arpc1b | actin related protein 2/3 complex, subunit 1B (Arpc1b). | 291 | 416 | 758 | 1.43 | 2.61 |
| | ILMN_65617 | LOC498276 | (Pred., sim. to) Fc gamma (IgG) receptor II (low affinity) alpha precursor | 1176 | 1889 | 3014 | 1.61 | 2.56 |
| | ILMN_68161 | LOC294337 | (Pred., sim. To) collagen alpha1 type VI-precursor (LOC294337). | 1024 | 2421 | 2622 | 2.36 | 2.56 |
| | ILMN_55414 | Fcgr3a | Fc fragment of IgG, low affinity IIIa, receptor (Fcgr3a). | 234 | 193 | 596 | 0.83 | 2.55 |
| | ILMN_61391 | Slc15a3 | peptide/histidine transporter PHT2 (Slc15a3). | 335 | 304 | 842 | 0.91 | 2.51 |
| | ILMN_55504 | Sparc | secreted acidic cysteine rich glycoprotein (Sparc). | 817 | 954 | 2041 | 1.17 | 2.50 |
| | ILMN_61139 | Icam1 | intercellular adhesion molecule 1 (Icam1). | 309 | 429 | 761 | 1.39 | 2.46 |
| | ILMN_51710 | Lyl1 | lymphoblastic leukemia derived sequence 1 (Lyl1). | 247 | 286 | 604 | 1.16 | 2.44 |
| | ILMN_67686 | Ms4a6b | membrane-spanning 4-domains, subfamily A, member 6B (Ms4a6b). | 241 | 418 | 588 | 1.74 | 2.44 |
| | ILMN_49562 | Laptm5 | lysosomal-associated protein transmembrane 5 (Laptm5). | 867 | 1575 | 2101 | 1.82 | 2.42 |
| | ILMN_52167 | Pdlim7 | PDZ and LIM domain 7 (Pdlim7). | 396 | 794 | 957 | 2.00 | 2.42 |
| | ILMN_69719 | Bf | B-factor, properdin (Bf). | 670 | 840 | 1589 | 1.25 | 2.37 |
| | ILMN_66756 | LOC293566 | (Pred., sim. To) carboxypeptidase X 2 (M14 family); metallocarboxypeptidase 2 | 230 | 261 | 541 | 1.13 | 2.35 |
| | ILMN_67382 | Cd63 | CD63 antigen (Cd63). | 728 | 982 | 1687 | 1.35 | 2.32 |
| | ILMN_52596 | Col1a2 | procollagen, type I, alpha 2 (Col1a2). | 894 | 1511 | 2071 | 1.69 | 2.32 |
| | ILMN_56539 | Slc13a3 | solute carrier family 13 (sodium-dependent dicarboxylate transporter)-3 | 387 | 542 | 888 | 1.40 | 2.29 |
| | ILMN_62982 | Tead3 | (Pred.) TEA domain family member 3 (Tead3). | 316 | 743 | 721 | 2.35 | 2.28 |
| | ILMN_66407 | Irf5 | (Pred.) interferon regulatory factor 5 (Irf5). | 294 | 467 | 662 | 1.59 | 2.25 |
| | ILMN_55731 | Bzrp | benzodiazepine receptor, peripheral (Bzrp). | 388 | 320 | 865 | 0.82 | 2.23 |
| | ILMN_61063 | Rhoc | (Pred.) ras homolog gene family, member C (Rhoc). | 990 | 1319 | 2204 | 1.33 | 2.23 |
| | ILMN_52522 | Phyhd1 | (Pred.) phytanoyl-CoA dioxygenase domain containing 1 (Phyhd1). | 501 | 875 | 1098 | 1.75 | 2.19 |
| | ILMN_55706 | C1s | complement component 1, s subcomponent (C1s). | 306 | 380 | 668 | 1.25 | 2.19 |
| | ILMN_61732 | Svil | (Pred.) supervillin (Svil). | 404 | 501 | 879 | 1.24 | 2.18 |
| | ILMN_63407 | Jak3 | Janus kinase 3 (Jak3). | 555 | 582 | 1204 | 1.05 | 2.17 |
| | ILMN_66976 | Col6a3 | (Pred.) procollagen, type VI, alpha 3 | 490 | 435 | 1052 | 0.89 | 2.15 |
| | ILMN_59412 | Emp3 | epithelial membrane protein 3 (Emp3). | 346 | 309 | 733 | 0.89 | 2.12 |
| | ILMN_59943 | Dnase2 | deoxyribonuclease II (Dnase2). | 374 | 547 | 778 | 1.46 | 2.08 |
| | ILMN_69305 | Ucp2 | uncoupling protein 2 (Ucp2). | 806 | 841 | 1632 | 1.04 | 2.02 |
| | ILMN_56191 | Mus81 | (Pred.) MUS81 endonuclease homolog (yeast) (Mus81). | 409 | 539 | 817 | 1.32 | 2.00 |
| | ILMN_49754 | Lrrk1 | (Pred.) leucine-rich repeat kinase 1 (Lrrk1). | 457 | 542 | 903 | 1.19 | 1.98 |
| | ILMN_62940 | LOC303731 | (Pred., sim. To) Chromobox protein homolog 8 (Polycomb 3 homolog) (Pc3) | 313 | 455 | 619 | 1.45 | 1.98 |
| | ILMN_48881 | LOC501102 | (Pred.) LOC501102 (LOC501102). | 339 | 451 | 669 | 1.33 | 1.98 |
| | ILMN_62729 | Chc1l | chromosome condensation 1-like (Chc1l). | 359 | 261 | 696 | 0.73 | 1.94 |
| | ILMN_66296 | MGC72598 | Unknown (protein for MGC:72598) (MGC72598). | 617 | 683 | 1183 | 1.11 | 1.92 |

TABLE 4-continued

Changes in gene expression in CSMNs contralateral to SMA infarct: effects of stroke alone and of inosine

| | | | | Signal Intensity | | | Fold-Induction | |
|---|---|---|---|---|---|---|---|---|
| | | | | Treatment after Stroke | | | Stroke, sal | Stroke, ino |
| Pattern | Target | Symbol | Definition | Control | Saline | Inosine | vs. cntrl | vs. cntrl |
| | ILMN_56245 | Ier3 | immediate early response 3 (Ier3). | 525 | 715 | 1007 | 1.36 | 1.92 |
| | ILMN_66840 | Lr8 | LR8 protein (Lr8). | 1194 | 1639 | 2275 | 1.37 | 1.90 |
| | ILMN_52177 | LOC361594 | (Pred., sim. To) hypothetical protein FLJ12484 (LOC361594). | 462 | 524 | 880 | 1.13 | 1.90 |
| | ILMN_69907 | Fcgrt | Fc receptor, IgG, alpha chain transporter (Fcgrt). | 637 | 695 | 1201 | 1.09 | 1.88 |
| | ILMN_55192 | Lamb2 | laminin, beta 2 (Lamb2). | 1388 | 1853 | 2612 | 1.34 | 1.88 |
| | ILMN_48533 | 1200013a08rik | limitrin (1200013a08rik). | 342 | 309 | 641 | 0.90 | 1.87 |
| | ILMN_59161 | Npc2 | Niemann Pick type C2 (Npc2). | 3884 | 4529 | 7067 | 1.17 | 1.82 |
| | ILMN_53627 | LOC499015 | (Pred., sim. To) serine active site containing 1 (LOC499015). | 475 | 280 | 849 | 0.59 | 1.79 |
| | ILMN_67564 | MGC105797 | similar to ubiquitously-expressed transcript isoform 1 (MGC105797). | 432 | 461 | 760 | 1.07 | 1.76 |
| | ILMN_53085 | Irf1 | interferon regulatory factor 1 (Irf1). | 595 | 530 | 1048 | 0.89 | 1.76 |
| | ILMN_58188 | Gp38 | glycoprotein 38 (Gp38). | 3165 | 2430 | 5501 | 0.77 | 1.74 |
| | ILMN_58496 | C1qa | complement component 1, q subcomponent, alpha polypeptide (C1qa). | 919 | 721 | 1561 | 0.79 | 1.70 |
| | ILMN_54242 | Vim | vimentin (Vim). | 812 | 499 | 1352 | 0.61 | 1.66 |
| | ILMN_57850 | LOC500795 | (Pred.) LOC500795 (LOC500795). | 685 | 475 | 1141 | 0.69 | 1.66 |
| | ILMN_52399 | LOC290851 | (Pred., sim. to) RIKEN cDNA 2210415M20 (LOC290851). | 1054 | 597 | 1691 | 0.57 | 1.60 |
| | ILMN_50631 | LOC315776 | (Pred., sim. to) talin 2 (LOC315776). | 484 | 298 | 718 | 0.62 | 1.48 |
| Not changed by stroke alone, significantly downregulated by inosine | ILMN_56273 | Bnip3 | BCL2/adenovirus E1B 19 kDa-interacting protein 3 (Bnip3). | 1627 | 1770 | 326 | 1.09 | 0.20 |
| | ILMN_52213 | LOC501140 | (Pred., sim. to) BCL2/adenovirus E1B 19 kDa-interacting protein 3 | 433 | 497 | 106 | 1.15 | 0.25 |
| | ILMN_64241 | Cd47 | CD47 antigen (Rh-related antigen, integrin-associated signal transducer) | 3212 | 2617 | 831 | 0.81 | 0.26 |
| | ILMN_48911 | Cacna2d1 | calcium channel, voltage-dependent, alpha2/delta subunit 1 (Cacna2d1). | 6289 | 3478 | 1708 | 0.55 | 0.27 |
| | ILMN_54952 | Stch | stress 70 protein chaperone, microsome-associated, 60 kD human homolog | 930 | 514 | 304 | 0.55 | 0.33 |
| | ILMN_56430 | 39332 | septin 7 (Sept7). | 651 | 317 | 226 | 0.49 | 0.35 |
| | ILMN_48422 | Rraga | Ras-related GTP-binding protein ragA (Rraga). | 1887 | 633 | 693 | 0.34 | 0.37 |
| | ILMN_63975 | Arhgef9 | Cdc42 guanine nucleotide exchange factor (GEF) 9 (Arhgef9). | 2689 | 2014 | 994 | 0.75 | 0.37 |
| | ILMN_56075 | Nup35 | nucleoporin 35 (Nup35). | 900 | 511 | 357 | 0.57 | 0.40 |
| | ILMN_52890 | Ccpg1 | (Pred.) cell cycle progression 1 (Ccpg1). | 562 | 338 | 228 | 0.60 | 0.41 |
| | ILMN_61248 | Gars | (Pred.) glycyl-tRNA synthetase (Gars). | 3082 | 1448 | 1274 | 0.47 | 0.41 |
| | ILMN_59830 | Sugt1 | (Pred.) SGT1, suppressor of G2 allele of SKP1 (*S. cerevisiae*) | 981 | 467 | 424 | 0.48 | 0.43 |
| | ILMN_50828 | LOC497712 | (Pred.) hypothetical gene supported by NM_001001511 (LOC497712). | 727 | 408 | 314 | 0.56 | 0.43 |
| | ILMN_50850 | Tsn | translin (Tsn). | 506 | 394 | 220 | 0.78 | 0.43 |
| | ILMN_65816 | Gda | guanine deaminase (Gda). | 2499 | 3640 | 1087 | 1.46 | 0.44 |
| | ILMN_63816 | Lsm8 | (Pred.) LSM8 homolog, U6 small nuclear RNA associated | 772 | 337 | 343 | 0.44 | 0.44 |
| | ILMN_51854 | LOC498726 | (Pred., sim. to) hypothetical protein C630023L15 (LOC498726). | 1020 | 1116 | 465 | 1.09 | 0.46 |
| | ILMN_59008 | LOC311236 | (Pred., sim. to) NAG14 protein (LOC311236). | 2166 | 1416 | 1008 | 0.65 | 0.47 |
| | ILMN_53875 | Znf148 | zinc finger protein 148 (Znf148). | 2434 | 2117 | 1149 | 0.87 | 0.47 |
| | ILMN_47975 | Rab9 | RAB9, member RAS oncogene family (Rab9). | 573 | 351 | 278 | 0.61 | 0.49 |
| | ILMN_65519 | LOC287596 | (Pred., sim. to) RIKEN cDNA 1200011M11 (LOC287596). | 670 | 480 | 330 | 0.72 | 0.49 |
| | ILMN_52256 | Nell1 | NEL-like 1 (chicken) (Nell1). | 4302 | 2802 | 2125 | 0.65 | 0.49 |
| | ILMN_68750 | Glg1 | golgi apparatus protein 1 (Glg1). | 454 | 431 | 226 | 0.95 | 0.50 |
| | ILMN_65606 | Rnf7 | (Pred.) ring finger protein 7 (Rnf7). | 892 | 715 | 460 | 0.80 | 0.52 |
| | ILMN_52424 | Rnf138 | ring finger protein 138 (Rnf138). | 1202 | 988 | 636 | 0.82 | 0.53 |
| | ILMN_61494 | Ak3 | adenylate kinase 3 (Ak3). | 853 | 628 | 452 | 0.74 | 0.53 |
| | ILMN_62536 | Ntrk2 | neurotrophic tyrosine kinase, receptor, type 2 (Ntrk2). | 2448 | 2256 | 1376 | 0.92 | 0.56 |
| | ILMN_54363 | LOC500721 | (Pred.) LOC500721 (LOC500721). | 463 | 473 | 263 | 1.02 | 0.57 |
| | ILMN_60231 | LOC309014 | (Pred., sim. to) HTPAP protein (LOC309014). | 401 | 503 | 232 | 1.25 | 0.58 |
| | ILMN_50309 | LOC302671 | (Pred., sim. to) Adapter-related protein complex 1 sigma 1B subunit | 1509 | 1779 | 919 | 1.18 | 0.61 |
| | ILMN_54925 | Dscam | (Pred.) Down syndrome cell adhesion molecule (Dscam). | 357 | 528 | 227 | 1.48 | 0.64 |

TABLE 4-continued

Changes in gene expression in CSMNs contralateral to SMA infarct: effects of stroke alone and of inosine

| Pattern | Target | Symbol | Definition | Signal Intensity Treatment after Stroke | | | Fold-Induction | |
|---|---|---|---|---|---|---|---|---|
| | | | | Control | Saline | Inosine | Stroke, sal vs. cntrl | Stroke, ino vs. cntrl |
| | ILMN_58100 | Tm7sf2 | (Pred.) transmembrane 7 superfamily member 2 (Tm7sf2). | 646 | 887 | 419 | 1.37 | 0.65 |
| | ILMN_68585 | P2rxl1 | purinergic receptor P2X-like 1, orphan receptor (P2rxl1). | 324 | 1161 | 246 | 3.58 | 0.76 |

TABLE 5

RNA integrity Detection score

| Treatment | N | Mean | S.D. | p value* |
|---|---|---|---|---|
| Control | 6 | 0.881 | 0.039 | (—) |
| Stroke/saline | 3 | 0.823 | 0.033 | n.s. |
| Stroke/inosine | 5 | 0.861 | 0.017 | n.s. |

*compared to normal controls

The invention claimed is:

1. A method for stimulating axonal outgrowth of mammalian central nervous system (CNS) neurons damaged by stroke comprising contacting the CNS neurons with an effective amount of NEP1-40 and inosine, to thereby stimulate axonal outgrowth.

2. The method of claim 1, further comprising contacting the CNS neurons with a cAMP modulator that increases the concentration of intracellular cAMP.

3. The method of claim 2, wherein the cAMP modulator is selected from the group consisting of: cAMP analogues, activators of G protein coupled receptors that activate cAMP, adenylate cyclase activators, calcium ionophores, and phosphodiesterase inhibitors.

4. A method for treating stroke in a patient in need thereof comprising administering an effective amount of NEP1-40 and inosine to the patient, to thereby contact and stimulate axonal outgrowth of central nervous system (CNS) neurons damaged by stroke, to thereby treat the stroke.

5. The method of claim 4, wherein the NEP1-40 and inosine are administered following an injury to the CNS, to thereby re-establish neural connectivity and/or function of the CNS neurons after the CNS injury.

6. The method of claim 4, wherein the NEP1-40 and inosine are administered by a route selected from the group consisting of pulmonary, internal topical, interdermal, intravenous, subcutaneous, intranasal, epidermal, ophthalmic, oral, intraventricular, and intrathecal.

* * * * *